US 12,246,175 B2

(12) United States Patent
Herron et al.

(10) Patent No.: US 12,246,175 B2
(45) Date of Patent: Mar. 11, 2025

(54) METHODS FOR POSITIONING SIGNAL DELIVERY DEVICES TO TREAT SLEEP APNEA, AND ASSOCIATED DEVICES AND TREATMENTS

(71) Applicant: Invicta Medical, Inc., Santa Clara, CA (US)

(72) Inventors: David Herron, Los Angeles, CA (US); Guillaume Raux, El Paso, TX (US); Timothy A. Fayram, Gilroy, CA (US); Richard W. O'Connor, Atherton, CA (US)

(73) Assignee: Invicta Medical, Inc., Santa Clara, CA (US)

( * ) Notice: Subject to any disclaimer, the term of this patent is extended or adjusted under 35 U.S.C. 154(b) by 0 days.

(21) Appl. No.: 18/607,289

(22) Filed: Mar. 15, 2024

(65) Prior Publication Data

US 2024/0307684 A1 Sep. 19, 2024

Related U.S. Application Data

(60) Provisional application No. 63/622,867, filed on Jan. 19, 2024, provisional application No. 63/452,918, filed on Mar. 17, 2023.

(51) Int. Cl.
*A61N 1/36* (2006.01)
*A61N 1/05* (2006.01)

(52) U.S. Cl.
CPC ....... *A61N 1/36003* (2013.01); *A61N 1/0551* (2013.01); *A61N 1/36192* (2013.01); *A61N 1/36139* (2013.01)

(58) Field of Classification Search
None
See application file for complete search history.

(56) References Cited

U.S. PATENT DOCUMENTS

| | | | |
|---|---|---|---|
| 4,365,636 A | 12/1982 | Barker | |
| 4,830,008 A | 5/1989 | Meer | |

(Continued)

FOREIGN PATENT DOCUMENTS

| | | |
|---|---|---|
| CA | 3166004 | 8/2021 |
| CN | 201361029 | 12/2009 |

(Continued)

OTHER PUBLICATIONS

U.S. Appl. No. 18/331,109, filed Jun. 7, 2023, Raux et al.

(Continued)

*Primary Examiner* — Ankit D Tejani
(74) *Attorney, Agent, or Firm* — Perkins Coie LLP

(57) ABSTRACT

The present technology is generally directed to methods for addressing a patient's sleep apnea. At least some of the methods can include one or more of percutaneously inserting an implantable signal delivery device at an insertion point on the patient's neck, moving the signal delivery device in a medial-to-lateral direction toward an ansa cervicalis nerve of the patient, and implanting the signal delivery device at a target location at least proximate to the ansa cervicalis nerve. The signal delivery device can include at least one electrode positioned to deliver a modulation signal to tissue at least proximate to the target location, such as a portion of the ansa cervicalis nerve. In some embodiments, delivery of the modulation signal can induce caudal traction in the patient and thereby address the patient's sleep apnea.

17 Claims, 24 Drawing Sheets

(56) References Cited

U.S. PATENT DOCUMENTS

| | | |
|---|---|---|
| 5,146,918 A | 9/1992 | Kallok et al. |
| 5,193,539 A | 3/1993 | Schulman |
| 5,193,540 A | 3/1993 | Schulman |
| 5,265,624 A | 11/1993 | Bowman |
| 5,540,732 A | 7/1996 | Testerman |
| 5,546,952 A | 8/1996 | Erickson |
| 6,132,384 A | 10/2000 | Christopherson et al. |
| 6,212,435 B1 | 4/2001 | Lattner |
| 6,240,316 B1 | 5/2001 | Richmond et al. |
| 6,251,126 B1 | 6/2001 | Ottenhoff et al. |
| 6,269,269 B1 | 7/2001 | Ottenhoff et al. |
| 6,345,202 B2 | 2/2002 | Richmond et al. |
| 6,582,441 B1 | 6/2003 | He et al. |
| 6,587,725 B1 | 7/2003 | Durand et al. |
| 6,636,767 B1 | 10/2003 | Knudson |
| 7,189,204 B2 | 3/2007 | Ni et al. |
| 7,252,640 B2 | 8/2007 | Ni et al. |
| 7,367,935 B2 | 5/2008 | Mechlenburg et al. |
| 7,371,220 B1 | 5/2008 | Koh et al. |
| 7,620,451 B2 | 11/2009 | Demarais et al. |
| 7,634,315 B2 | 12/2009 | Mashiach et al. |
| 7,660,632 B2 | 2/2010 | Kirby et al. |
| 7,672,728 B2 | 3/2010 | Libbus et al. |
| 7,680,538 B2 | 3/2010 | Durand et al. |
| 7,684,858 B2 | 3/2010 | He et al. |
| 7,761,167 B2 | 7/2010 | Bennett et al. |
| 7,822,480 B2 | 10/2010 | Park et al. |
| 7,882,842 B2 | 2/2011 | Bhat et al. |
| 7,920,915 B2 | 4/2011 | Mann |
| 8,024,044 B2 | 9/2011 | Kirby et al. |
| 8,249,723 B2 | 8/2012 | McCreery |
| 8,340,785 B2 | 12/2012 | Bonde et al. |
| 8,359,108 B2 | 1/2013 | McCreery |
| 8,498,712 B2 | 7/2013 | Bolea |
| 8,574,164 B2 | 11/2013 | Mashiach |
| 8,577,464 B2 | 11/2013 | Mashiach |
| 8,577,465 B2 | 11/2013 | Mashiach |
| 8,577,478 B2 | 11/2013 | Mashiach et al. |
| 8,585,617 B2 | 11/2013 | Mashiach et al. |
| 8,588,941 B2 | 11/2013 | Mashiach |
| 8,644,957 B2 | 2/2014 | Mashiach |
| 8,655,451 B2 | 2/2014 | Klosterman |
| 8,684,925 B2 | 4/2014 | Manicka et al. |
| 8,688,219 B2 | 4/2014 | Ransom |
| 8,774,943 B2 | 7/2014 | McCreery et al. |
| 8,812,130 B2 | 8/2014 | Stahmann et al. |
| 8,909,351 B2 | 12/2014 | Dinsmoor et al. |
| 8,938,299 B2 | 1/2015 | Christopherson et al. |
| 8,983,572 B2 | 3/2015 | Ni |
| 8,983,611 B2 | 3/2015 | Mokelke et al. |
| 9,031,653 B2 | 5/2015 | Mashiach |
| 9,042,995 B2 | 5/2015 | Dinsmoor |
| 9,061,162 B2 | 6/2015 | Mashiach et al. |
| 9,136,728 B2 | 9/2015 | Dinsmoor |
| 9,155,899 B2 | 10/2015 | Mashiach et al. |
| 9,186,511 B2 | 11/2015 | Bolea |
| 9,205,255 B2 | 12/2015 | Strother |
| 9,227,053 B2 | 1/2016 | Bonde et al. |
| 9,248,302 B2 | 2/2016 | Mashiach et al. |
| 9,308,381 B2 | 4/2016 | Mashiach et al. |
| 9,402,563 B2 | 8/2016 | Thakur et al. |
| 9,409,013 B2 | 8/2016 | Mashiach |
| 9,415,215 B2 | 8/2016 | Mashiach |
| 9,415,223 B2 | 8/2016 | Carbunaru et al. |
| 9,463,318 B2 | 10/2016 | Mashiach et al. |
| 9,486,628 B2 | 11/2016 | Christopherson et al. |
| 9,504,828 B2 | 11/2016 | Mashiach et al. |
| 9,586,048 B2 | 3/2017 | Ternes et al. |
| 9,808,620 B2 | 4/2017 | Kent |
| 9,643,022 B2 | 5/2017 | Mashiach et al. |
| 9,687,664 B2 | 6/2017 | Poon et al. |
| 9,839,786 B2 | 12/2017 | Rondoni et al. |
| 9,849,289 B2 | 12/2017 | Mashiach et al. |
| 9,855,431 B2 | 1/2018 | Ternes |
| 9,888,864 B2 | 2/2018 | Rondoni et al. |
| 9,889,299 B2 | 2/2018 | Ni et al. |
| 9,895,541 B2 | 2/2018 | Meadows et al. |
| 9,907,967 B2 | 3/2018 | Mashiach et al. |
| 9,943,391 B2 | 4/2018 | Chu |
| 9,950,166 B2 | 4/2018 | Mashiach et al. |
| 10,004,913 B2 | 6/2018 | Poon et al. |
| 10,052,097 B2 | 8/2018 | Mashiach et al. |
| 10,195,426 B2 | 2/2019 | Kent |
| 10,195,427 B2 | 2/2019 | Kent |
| 10,195,428 B2 | 2/2019 | Scheiner |
| 10,238,872 B2 | 3/2019 | Pivonka et al. |
| 10,314,501 B2 | 6/2019 | Zitnik et al. |
| 10,335,596 B2 | 7/2019 | Yakovlev et al. |
| 10,512,782 B2 | 12/2019 | Mashiach et al. |
| 10,583,297 B2 | 3/2020 | Ni |
| 10,594,166 B2 | 3/2020 | Ho et al. |
| 10,716,940 B2 | 7/2020 | Mashiach et al. |
| 10,744,339 B2 | 8/2020 | Makansi |
| 10,751,537 B2 | 8/2020 | Mashiach et al. |
| 10,806,926 B2 | 10/2020 | Christopherson et al. |
| 10,828,502 B2 | 11/2020 | Poon et al. |
| 10,898,709 B2 | 1/2021 | Wagner et al. |
| 10,932,682 B2 | 3/2021 | Christopherson et al. |
| 10,967,183 B2 | 4/2021 | Yakovlev et al. |
| 10,994,139 B2 | 5/2021 | Fayram et al. |
| 11,090,491 B2 | 8/2021 | Mashiach et al. |
| 11,160,980 B2 | 11/2021 | Mashiach et al. |
| 11,253,712 B2 | 2/2022 | Mashiach |
| 11,266,837 B2 | 3/2022 | Scheiner et al. |
| 11,273,305 B2 | 3/2022 | Scheiner et al. |
| 11,291,842 B2 | 4/2022 | Caparso et al. |
| 11,298,549 B2 | 4/2022 | Mashiach et al. |
| 11,324,950 B2 | 5/2022 | Dieken et al. |
| 2001/0023362 A1 | 9/2001 | Kobayashi |
| 2003/0195571 A1 | 10/2003 | Burnes et al. |
| 2004/0073272 A1 | 4/2004 | Knudson |
| 2005/0043644 A1 | 2/2005 | Stahmann et al. |
| 2005/0085874 A1 | 4/2005 | Davis |
| 2005/0137646 A1 | 6/2005 | Wallace |
| 2005/0261600 A1 | 11/2005 | Aylsworth |
| 2006/0155206 A1 | 7/2006 | Lynn |
| 2006/0247729 A1 | 11/2006 | Tehrani |
| 2007/0173893 A1 | 7/2007 | Pitts |
| 2008/0033304 A1 | 2/2008 | Dalal |
| 2008/0103545 A1 | 5/2008 | Bolea |
| 2009/0030469 A1 | 1/2009 | Meiry |
| 2009/0118610 A1 | 5/2009 | Karmarkar et al. |
| 2010/0094376 A1 | 4/2010 | Penner |
| 2010/0094379 A1 | 4/2010 | Meadows |
| 2010/0094398 A1 | 4/2010 | Malewicz |
| 2010/0152546 A1 | 6/2010 | Behan et al. |
| 2010/0241195 A1 | 9/2010 | Meadows |
| 2011/0093032 A1 | 4/2011 | Boggs, II |
| 2011/0093036 A1 | 4/2011 | Mashiach |
| 2011/0112601 A1 | 5/2011 | Meadows et al. |
| 2011/0132378 A1 | 6/2011 | Levendowski |
| 2011/0152965 A1 | 6/2011 | Mashiach |
| 2011/0172733 A1 | 7/2011 | Lima et al. |
| 2011/0172743 A1 | 7/2011 | Davis et al. |
| 2011/0213438 A1 | 9/2011 | Lima et al. |
| 2011/0230702 A1 | 9/2011 | Honour |
| 2011/0264164 A1 | 10/2011 | Christopherson |
| 2012/0029362 A1 | 2/2012 | Patangay et al. |
| 2012/0089153 A1 | 4/2012 | Christopherson |
| 2012/0192874 A1 | 8/2012 | Bolea |
| 2012/0197340 A1 | 8/2012 | Tesfayesus |
| 2013/0072999 A1 | 3/2013 | Mashiach |
| 2013/0085537 A1 | 4/2013 | Mashiach |
| 2013/0085544 A1 | 4/2013 | Mashiach |
| 2013/0085560 A1 | 4/2013 | Mashiach |
| 2013/0261693 A1 | 10/2013 | Gross |
| 2014/0046221 A1 | 2/2014 | Mashiach |
| 2014/0135868 A1 | 5/2014 | Bashyam |
| 2014/0228905 A1 | 8/2014 | Bolea |
| 2015/0029030 A1 | 1/2015 | Aoyama |
| 2015/0038865 A1 | 2/2015 | Shigeto |
| 2015/0039046 A1 | 2/2015 | Gross |
| 2015/0073232 A1 | 3/2015 | Ahmed |
| 2015/0142120 A1 | 5/2015 | Papay |

(56) References Cited

U.S. PATENT DOCUMENTS

| | | |
|---|---|---|
| 2015/0182753 A1 | 7/2015 | Harris |
| 2015/0224307 A1 | 8/2015 | Cyberonics |
| 2015/0273177 A1 | 10/2015 | Lizuka |
| 2015/0374991 A1 | 12/2015 | Morris et al. |
| 2016/0089540 A1 | 3/2016 | Bolea |
| 2016/0331952 A1 | 11/2016 | Faltys |
| 2017/0014068 A1 | 1/2017 | Gotoh et al. |
| 2017/0087360 A1 | 3/2017 | Scheiner |
| 2017/0095667 A1 | 4/2017 | Yakovelev et al. |
| 2017/0135604 A1 | 5/2017 | Kent |
| 2017/0135629 A1 | 5/2017 | Kent |
| 2017/0143257 A1 | 5/2017 | Kent |
| 2017/0143259 A1 | 5/2017 | Kent |
| 2017/0143280 A1 | 5/2017 | Kent |
| 2017/0143960 A1 | 5/2017 | Kent |
| 2017/0151432 A1 | 6/2017 | Christopherson |
| 2017/0224987 A1 | 8/2017 | Kent |
| 2017/0368341 A1 | 12/2017 | Bolea |
| 2018/0015282 A1 | 1/2018 | Waner |
| 2018/0085593 A1 | 3/2018 | Fayram et al. |
| 2018/0220921 A1 | 8/2018 | Rondoni et al. |
| 2018/0221660 A1 | 8/2018 | Suri et al. |
| 2019/0001139 A1 | 1/2019 | Mishra et al. |
| 2019/0022383 A1 | 1/2019 | Hadlock |
| 2019/0057700 A1 | 2/2019 | Kent |
| 2019/0060642 A1 | 2/2019 | Boggs et al. |
| 2019/0099285 A1 | 4/2019 | Bachelder |
| 2019/0117967 A1 | 4/2019 | Scheiner |
| 2019/0374776 A1 | 12/2019 | Mishra et al. |
| 2020/0001077 A1 | 1/2020 | Kent |
| 2020/0016401 A1 | 1/2020 | Papay et al. |
| 2020/0038033 A1 | 2/2020 | Clark et al. |
| 2020/0054867 A1 | 2/2020 | Schwartz et al. |
| 2020/0054889 A1 | 2/2020 | Makansi |
| 2020/0069947 A1 | 3/2020 | Kent |
| 2020/0139138 A1 | 5/2020 | Sit |
| 2020/0281763 A1 | 9/2020 | Scheiner |
| 2020/0316373 A1 | 10/2020 | Bolea |
| 2020/0338358 A1 | 10/2020 | Makansi |
| 2020/0346010 A1 | 11/2020 | Papay et al. |
| 2020/0346016 A1 | 11/2020 | Caparso et al. |
| 2020/0376261 A1 | 12/2020 | Stevens et al. |
| 2021/0106824 A1 | 4/2021 | Caparso et al. |
| 2021/0321939 A1 | 10/2021 | Kent |
| 2021/0052888 A1 | 12/2021 | Kent |
| 2022/0032052 A1 | 2/2022 | Kent et al. |
| 2022/0126103 A1 | 4/2022 | Pivonka et al. |
| 2022/0134101 A1 | 5/2022 | Scheiner et al. |
| 2022/0134102 A1 | 5/2022 | Kent |
| 2022/0161031 A1 | 5/2022 | O'Connor et al. |
| 2022/0218988 A1 | 7/2022 | Caparso et al. |
| 2022/0339441 A1 | 10/2022 | Elliott |
| 2022/0346666 A1 | 11/2022 | Elliott |
| 2022/0370797 A1 | 11/2022 | O'Connor |
| 2022/0379114 A1* | 12/2022 | Kent .................. A61N 1/36139 |
| 2022/0409897 A1 | 12/2022 | O'Connor |
| 2023/0026728 A1 | 1/2023 | Elliott |
| 2023/0172479 A1 | 6/2023 | Verzal |
| 2023/0240715 A1 | 8/2023 | Paspa et al. |
| 2023/0302280 A1 | 9/2023 | O'Connor |
| 2023/0321440 A1 | 10/2023 | O'Connor |
| 2023/0414945 A1 | 12/2023 | Ward |
| 2024/0307697 A1 | 9/2024 | Mullins et al. |

FOREIGN PATENT DOCUMENTS

| | | |
|---|---|---|
| KR | 20060087852 | 8/2006 |
| KR | 10-2019-0049502 | 5/2019 |
| WO | WO-9720522 | 6/1997 |
| WO | WO-2010006218 | 1/2010 |
| WO | WO-2012027648 | 3/2012 |
| WO | WO-2013172935 | 11/2013 |
| WO | WO-2017070372 | 4/2017 |
| WO | WO-2019140404 | 7/2019 |
| WO | WO-2020181120 | 9/2020 |
| WO | WO-2021050829 | 3/2021 |
| WO | WO-2021163228 | 8/2021 |
| WO | WO-2021242633 | 12/2021 |
| WO | WO-2022058024 | 3/2022 |
| WO | WO-2022129234 | 6/2022 |
| WO | WO-2022129236 | 6/2022 |
| WO | WO-2022129247 | 6/2022 |
| WO | 2023247333 | 12/2023 |

OTHER PUBLICATIONS

Atkinson, Martin, "Anatomy for Dental Students," OUP Oxford Fourth Edition, Mar. 14, 2013, p. 298.

Kent et al., "Ultrasound Localization and Percutaneous Electrical Stimulation of the Hypoglossal Nerve and Ansa Cervivalis," Otolaryngology Head and Neck Surgery, 2020, 7 pages.

Weaker, Frank, "Structures of the Head and Neck," F.A. Davis, Sep. 24, 2013, p. 77.

Website: CawBing: Snore Stopper Adjustable Snore Reduction Straps Anti Apnea Snore Support Belt Jaw Sleep Band Snoring Chin Strap, https://www.walmart.com/ip/Snore-Stopper-Adjustable-Snore-Reduction-Straps-Anti-Apnea-Snore-Support-Belt-Jaw-Sleep-Band-Snoring-Chin-Strap/788742945, accessed Jun. 2022, 5 pages.

Website: Halo Chinstrap by Breathwear Inc., https://www.cpap.com/productpage/breathewear-halo-chinstrap, accessed Jun. 2022, 3 pages.

Benbassat et al., "The specific branches leading to the genioglossus muscle: three dimensional localisation using skin reference points," Surgical and Radiologic Anatomy, 2019, 9 pages.

Delaey et al., "Specific branches of hypoglossal nerve to genioglossus muscle as a potential target of selective neurostimulation in obstructive sleep apnea: anatomical and morphometric study," Surg Radiol Anata, 2017, 9 pages.

Gharb et al., "Microsurgical Anatomy of the Terminal Hypoglossal Nerve Relevant for Neurostimulation in Obstructive Sleep Apnea," Neuromodulation: Technology at the Neural Interface, 2015, 8 pages.

Heiser et al., "Surgical anatomy of the hypoglossal nerve: A new classification system for selective upper airway stimulation," Wiley Periodicals, Inc., wileyonlinelibrary.com/journal/hed, 2017, 10 pages.

Li et al., "Dynamic Drug-Induced Sleep Computed Tomography in Adults with Obstructive Sleep Apnea," Scientific Reports—www.nature.com/scientificreports, Oct. 2016, 8 pages.

Mu et al., "Human Tongue Neuroanatomy: Nerve Supply and Motor Endplates," National Institute of Health, 2012, 27 pages.

Pearse et al., "Review: Sleep-Disordered Breathing in Heart Failure," Imperial College London and Royal Brompton Hospital, London, United Kingdom, https://onlinelibrary.wiley.com/doi/full/10.1002/ejhf.492, published Feb. 11, 2016, 26 pages.

Vroegop et al., "Sleep endoscopy with simulation bite for prediction of oral appliance treatment outcome," Obstructive Sleep Apnea, European Sleep Research Society, 2012, 8 pages.

Wirth et al., "Hypogloassal nerve stimulation therapy does not alter tongue protrusion strength and fatigability in obstructive sleep apnea," Journal of Clinical Sleep Medicine, vol. 16, No. 2., Feb. 2020, 8 pages.

International Search Report and Written Opinion for International Patent Application No. PCT/US2024/020273, Applicant: Invicta Medical, Inc., mailed Aug. 27, 2024, 12 pages.

* cited by examiner

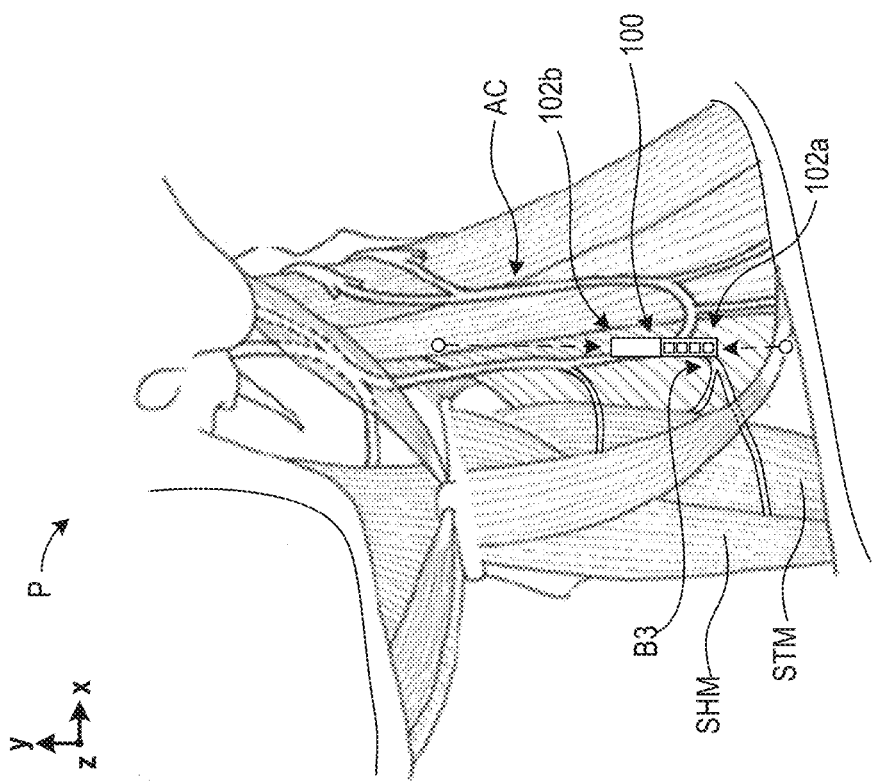
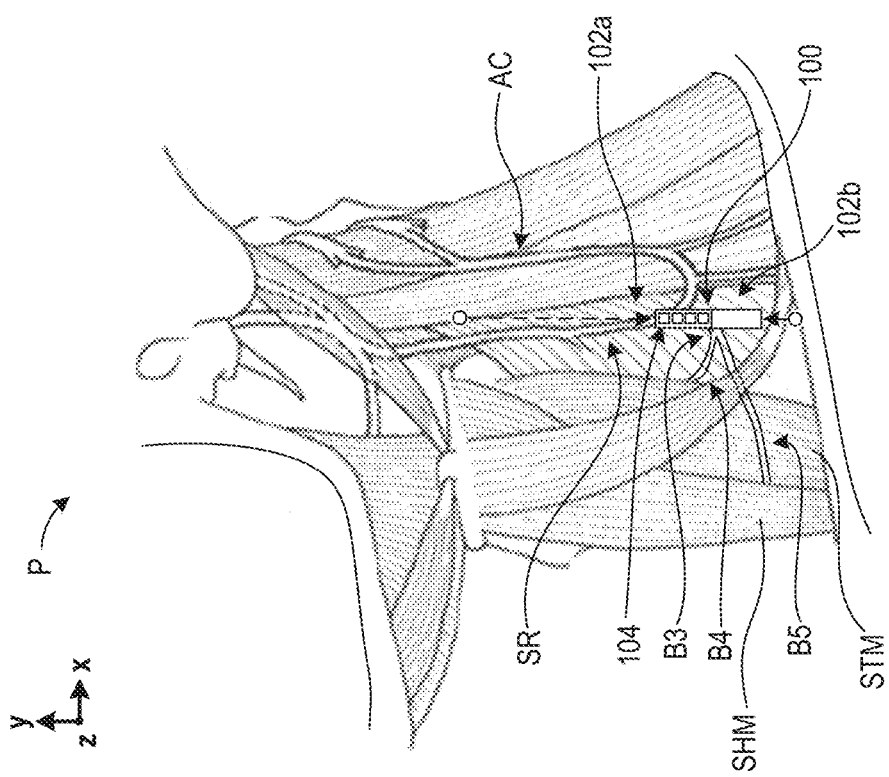

| # | Improved Flow? | Main Collapse Site | VOTE Scores ||||| Caudal Traction? | Stimulation Amplitude | Delivery Approach | Peak Flow Amplitude Increase Stim ON vs Off |
|---|---|---|---|---|---|---|---|---|---|---|---|
| | | | Velum (Retropalatal) | Oropharynx | Tongue Base (Retrolingual) | Epiglottis (Retroepiglottic) | | | | |
| 1 | Y | Velum | LA | A/P | A/P | A/P | Y | 4 mA | Med-to-Lat | >100% increase |
| 2 | Y | Tongue Base | Concentric (w/ jaw thrust) | - | A/P, LA (not complete for LA) | - | Y | 3 mA | Lat-to-Med | 80-100% increase |
| 3 | Y | Tongue Base | A/P | - | A/P | A/P | Y | 1.5-2 mA | Lat-to-Med | >>100% increase |
| 4 | Y | Tongue Base & Epiglottis | A/P | A/P, LA | A/P | A/P, Concentric | Y | 0.5-1.5 mA | Med-to-Med | >>100% increase |
| 5 | Minor | - | Concentric | LA | - | - | Y | 3 mA | Med-to-Lat Lat-to-Med | 40%, for one breath at a time |
| 6 | Y | Velum | A/P | - | - | - | Y | 5 mA | Lat-to-Med | >>100% increase |
| 7 | Y | Velum | A/P (Hor soft palate) | - | A/P | A/P (omega-shaped epiglottis) | Y | 4 mA | Lat-to-Med | >>100% increase |

*FIG. 10B*

METHODS FOR POSITIONING SIGNAL DELIVERY DEVICES TO TREAT SLEEP APNEA, AND ASSOCIATED DEVICES AND TREATMENTS

CROSS-REFERENCE TO RELATED APPLICATION(S)

The present application claims priority to U.S. Provisional No. 63/452,918, filed Mar. 17, 2023 and U.S. Provisional No. 63/622,867, filed Jan. 19, 2024. Both of the above-identified applications are incorporated by reference herein in their entireties.

TECHNICAL FIELD

The present technology is directed to methods for positioning signal delivery devices to treat sleep apnea, and associated devices and treatments.

BACKGROUND

Obstructive sleep apnea (OSA) is a medical condition in which a patient's upper airway is occluded (partially or fully) during sleep, causing sleep arousal. Repeated occlusions of the upper airway may cause sleep fragmentation, which in turn may result in sleep deprivation, daytime tiredness, and/or malaise. More serious instances of OSA may increase the patient's risk for stroke, cardiac arrhythmias, high blood pressure, and/or other disorders.

OSA may be characterized by the tendency for soft tissues of the upper airway to collapse during sleep, thereby occluding the upper airway. OSA is typically caused by the collapse of the patient's soft palate, oropharynx, tongue, epiglottis, or combination thereof, into the upper airway, which in turn may obstruct normal breathing and/or cause arousal from sleep.

Some treatments have been available for OSA including, for example, surgery, constant positive airway pressure (CPAP) machines, and electrically stimulating muscles or related nerves associated with the upper airway to move the tongue (or other upper airway tissue). Surgical techniques have included procedures to remove portions of a patient's tongue and/or soft palate, and other procedures that seek to prevent the tongue from collapsing into the back of the pharynx. These surgical techniques are very invasive. CPAP machines seek to maintain upper airway patency by applying positive air pressure at the patient's nose and mouth. However, these machines are uncomfortable, cumbersome, and may have low compliance rates.

Some electrical modulation techniques seek to prevent the tongue from collapsing into the back of the pharynx by causing the tongue to protrude forward (e.g., in an anterior direction) and/or flatten during sleep. However, existing techniques for electrically stimulating the nerves of the patient's oral cavity suffer from being too invasive and/or not sufficiently efficacious. Thus, there is a need for an improved minimally invasive treatment for OSA and other sleep disorders.

BRIEF DESCRIPTION OF THE DRAWINGS

FIGS. 5A and 5B are side sectional views of a portion of a patient's neck and lower jaw and depicting respective signal delivery device implantation positions in accordance with embodiments of the present technology.

FIG. 10B is a table including data obtained by positioning and activating a signal delivery device in accordance with embodiments of the present technology.

DETAILED DESCRIPTION

Figure 1A:
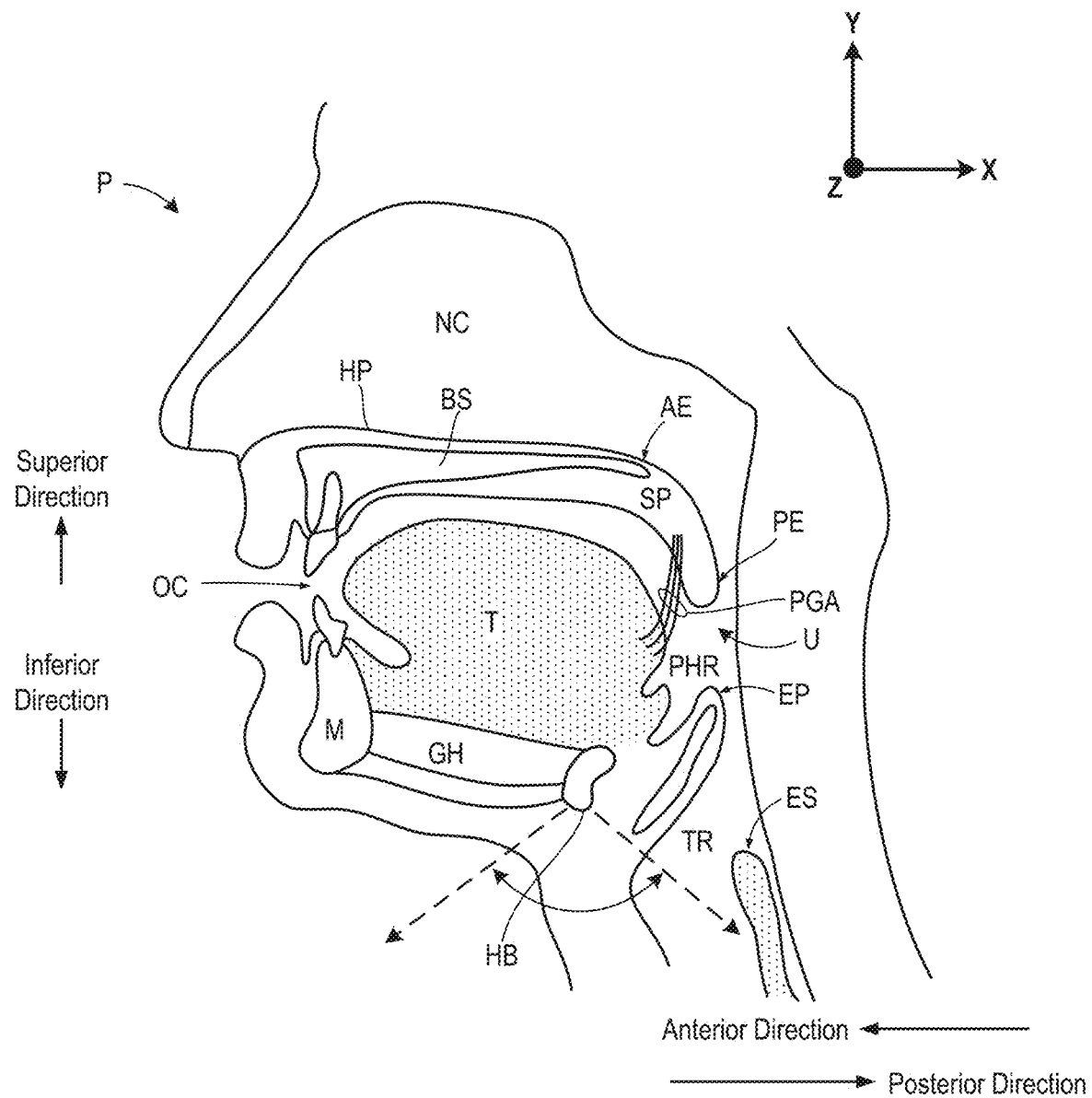
FIG. 1A is a side sectional view depicting a patient's upper airway.

The present technology is discussed under the following headings for ease of readability:
Heading 1: "Introduction"
Heading 2: "Overall Patient Physiology" (with a focus on FIGS. 1A-1D)
Heading 3: "Representative Insertion Paths and Target Tissues" (with a focus on FIGS. 2A-9B)
Heading 4: "Representative Experimental Data" (with a focus on FIGS. 10A-10C)
Heading 5: "Additional Devices, Systems, and Methods" (with a focus on FIGS. 11 and 12)
Heading 6: "Examples"

Although embodiments of the present technology are described under the selected headings indicated above, other embodiments of the technology can include elements discussed under multiple headings. Accordingly, even though an embodiment may be discussed under a particular heading, that embodiment is not limited to only the elements discussed under that heading.

1. Introduction

Electrical stimulation therapy for obstructive sleep apnea (OSA) typically includes delivering a modulation signal that modulates nerves and/or muscles to cause (i) the tongue and/or other soft tissue to move and/or (ii) change the tissue tone (e.g., tighten or stiffen the tissue without muscular contraction or extension that induces movement). The electrical stimulation can accordingly remove an obstruction of the upper airway, and/or prevent the tongue or other soft tissue from collapsing or obstructing the airway. As used herein, the terms "modulate" and "stimulate" are used interchangeably to mean having an effect on an effect on a nerve, a muscle and/or other tissue that in turn has an effect on one or more motor functions (e.g., a breathing-related motor function).

Representative methods and apparatuses for reducing the occurrence and/or severity of a breathing disorder, such as OSA, OSA with complete concentric collapse ("CCC"), central sleep apnea, and/or the like, are disclosed herein. In some embodiments, a signal delivery device is implanted at least proximate to or contacting one or more target tissues of the patient's upper airway, such as one or more nerves that innervate a muscle in the patient's airway and/or oral cavity. The signal delivery device can be implanted in the patient via a minimally invasive percutaneous injection. The signal delivery device can receive power wirelessly from an external device and use that power to generate and/or deliver accurately targeted modulation signals (e.g., electrical signals, stimulation pulses, etc.) to the target tissues, thereby improving the patient's upper airway patency and/or improve the tone of the tissue of the intraoral cavity to treat sleep apnea. The external device can include one or more mouthpiece portions, collar portions, chinstrap portions, pillow portions, mattress overlay portions, and/or one or more other suitable wearable structures.

Representative target tissues include nerves such as the ansa cervicalis nerve and/or the hypoglossal nerve, which are located adjacent and/or around the oral cavity or in the neck. Stimulating the ansa cervicalis nerve can induce caudal traction (e.g., of the trachea), lower or depress the hyoid bone, and/or stabilize or stiffen the tongue and/or soft tissues of the upper airway. This, in turn, can reduce or prevent tissue collapse and/or other airflow obstructions in the patient's airway, thereby improving airflow through the upper airway and mitigating or even alleviating the breathing obstruction. For example, because the tongue is attached to the hyoid bone, lowering the hyoid bone can (i) draw the tongue downwardly/inferiorly and prevent, or at least partially prevent, the tongue and/or associated tissues from obstructing the patient's airway, and/or (ii) improve airflow through the upper airway. Stimulating the hypoglossal nerve can cause the patient's tongue to move anteriorly/forward and/or improve tissue tone to prevent the tongue and/or other soft tissues in the airway from collapsing onto the back of the patient's pharynx and/or into the upper airway. Such movement of potentially obstructive tissue in the upper airway/pharynx is expected to improve the patient's sleep by mitigating or alleviating the obstruction. Further target tissues can include one or more muscles innervated by the hypoglossal nerve or the ansa cervicalis nerve (e.g., one or more of the patient's infrahyoid strap muscles, including the sternohyoid muscles and/or the sternothyroid muscles), the glossopharyngeal nerve, the pharyngeal branches of the glossopharyngeal nerve, the pharyngeal plexus, the C2 or C3 spinal nerve, a lateral part of the epidural space at the C1, C2, and C3 vertebral bodies, the pharyngeal branches of the glossopharyngeal nerve, and/or other suitable and/or therapeutically effective targets. Accordingly, the devices and associated methods disclosed herein can improve the patient's sleep by moving and/or stabilizing potentially obstructing tissue in the upper airway/pharynx. More specifically, applying the modulation signal to one or more portions of the ansa cervicalis nerve and/or directly to one or more of the patient's infrahyoid strap muscles can (i) cause the patient's hyoid bone to move inferiorly (e.g., caudal traction), (ii) increase a stiffness of the patient's pharyngeal wall, and/or (iii) otherwise at least partially or fully prevent soft tissue collapse that would otherwise have an obstructive effect on the patient's upper airway.

Many embodiments of the technology described below may take the form of computer- or machine- or controller-executable instructions, including routines executed by a programmable computer or controller. Those skilled in the relevant art will appreciate that the technology can be practiced on computer/controller systems other than those shown and described below. The technology can be embodied in a special-purpose computer, controller or data processor that is specifically programmed, configured or constructed to perform one or more of the computer-executable instructions described below. Accordingly, the terms "computer" and "controller" as generally used herein refer to any suitable data processor and can include Internet appliances and hand-held devices (including palm-top computers, wearable computers, tablets, cellular or mobile phones, multi-processor systems, processor-based or programmable consumer electronics, network computers, minicomputers and the like). Information handled by these computers can be presented at any suitable display medium, including a liquid crystal display (LCD). In some embodiments, manufacturers or other suitable entities can provide instructions to practitioners for executing the methods disclosed herein. Manufacturers can also program devices of the disclosed systems to carry out at least some of these methods.

The present technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on any suitable computer-readable media, including one or more ASICs, (e.g., with addressable memory), as well as distributed electronically over networks. Data structures and transmissions of data particular to aspects of the technology are also encompassed within the scope of the embodiments of the technology.

2. Overall Patient Physiology

Representative embodiments described herein include signal delivery devices having electrodes that can be positioned to deliver one or more electrical currents to one or more specific target locations, e.g., specific nerves and/or specific positions along a nerve. Such locations include locations along the patient's ansa cervicalis nerve, hypoglossal nerve, and/or vagus nerve. Additional locations include nerves that innervate muscles of the airway (e.g., palatal, oropharyngeal, laryngeal, omohyoid, sternohyoid, sternothyroid, thyrohyoid, nasal, lingual, pharyngeal, infrahyoid, diaphragmatic, and/or intercostal muscles). The target location can be identified with respect to any of, or any combination of, intrinsic or extrinsic muscles, associated nerve branches and/or portions thereof, and/or other physiological features.

FIG. 1A illustrates a patient P relative to a coordinate system in which the x-axis denotes the anterior-posterior directions, the y-axis denotes the superior-inferior and/or cranial-caudal directions, and the z-axis denotes the medial-lateral directions. The patient P has a hard palate HP which overlies the tongue T and forms the roof of the oral cavity OC (e.g., the mouth). The hard palate HP includes bone support BS, and thus does not typically deform during breathing. The soft palate SP, which is made of soft tissue such as membranes, fibrous material, fatty tissue, and muscle tissue, extends rearward (e.g., in a posterior direction) from the hard palate HP toward the back of the pharynx PHR. More specifically, an anterior end AE of the soft palate SP is anchored to a posterior end of the hard palate HP, and a posterior end PE of the soft palate SP is unattached. Because the soft palate SP does not contain bone or hard cartilage, the soft palate SP is flexible and may collapse onto the back of the pharynx PHR and/or flap back and forth (e.g., especially during sleep).

The pharynx PHR, which passes air from the oral cavity OC and the nasal cavity NC into the trachea TR, is the part of the throat situated inferior to (below) the nasal cavity NC, posterior to (behind) the oral cavity OC, and superior to (above) the esophagus ES. The pharynx PHR is separated from the oral cavity OC by the palatoglossal arch PGA, which runs downward on either side to the base of the tongue T. Although not shown for simplicity, the pharynx PHR includes the nasopharynx, the velopharynx, the oropharynx, and the laryngopharynx. The nasopharynx lies between the base of the cranium and the soft palate SP. The velopharynx is the section of the nasopharynx bounded ventrally by the soft palate. The oropharynx lies behind the oral cavity OC and extends from the soft palate SP to the pharyngoepiglottic fold. The oropharynx opens anteriorly into the oral cavity OC. The anterior portion of the oropharynx includes the base of the tongue T. A flap of connective tissue called the epiglottis EP closes over the glottis (not shown for simplicity) when food is swallowed, to prevent aspiration. The laryngopharynx is the portion of the pharynx that divides anteriorly into the larynx and posteriorly into the esophagus, and is bounded by the pharyngoepiglottic fold superiorly and the upper esophageal sphincter inferiorly. Below the tongue T is the lower jaw or mandible M, and the geniohyoid muscle GH, which is one of the muscles, in addition to the infrahyoid strap muscles, that controls the movement of the hyoid bone HB. Stimulating one or more of the patient's infrahyoid strap muscles (and/or a nerve innervating one or more of the patient's infrahyoid strap muscles) can lower the hyoid bone HB, including in an anterior or posterior direction such as shown using dashed-line arrows in FIG. 1B, and produce a corresponding movement of at least the base of the patient's tongue T. As described in greater detail below, lowering the base of the patient's tongue T can open the patient's airway, and/or reduce or prevent tissue collapse that at least partially obstructs the patient's airway, to increase airflow through the oral cavity OC and address OSA and/or other breathing obstructions.

Figure 1B:
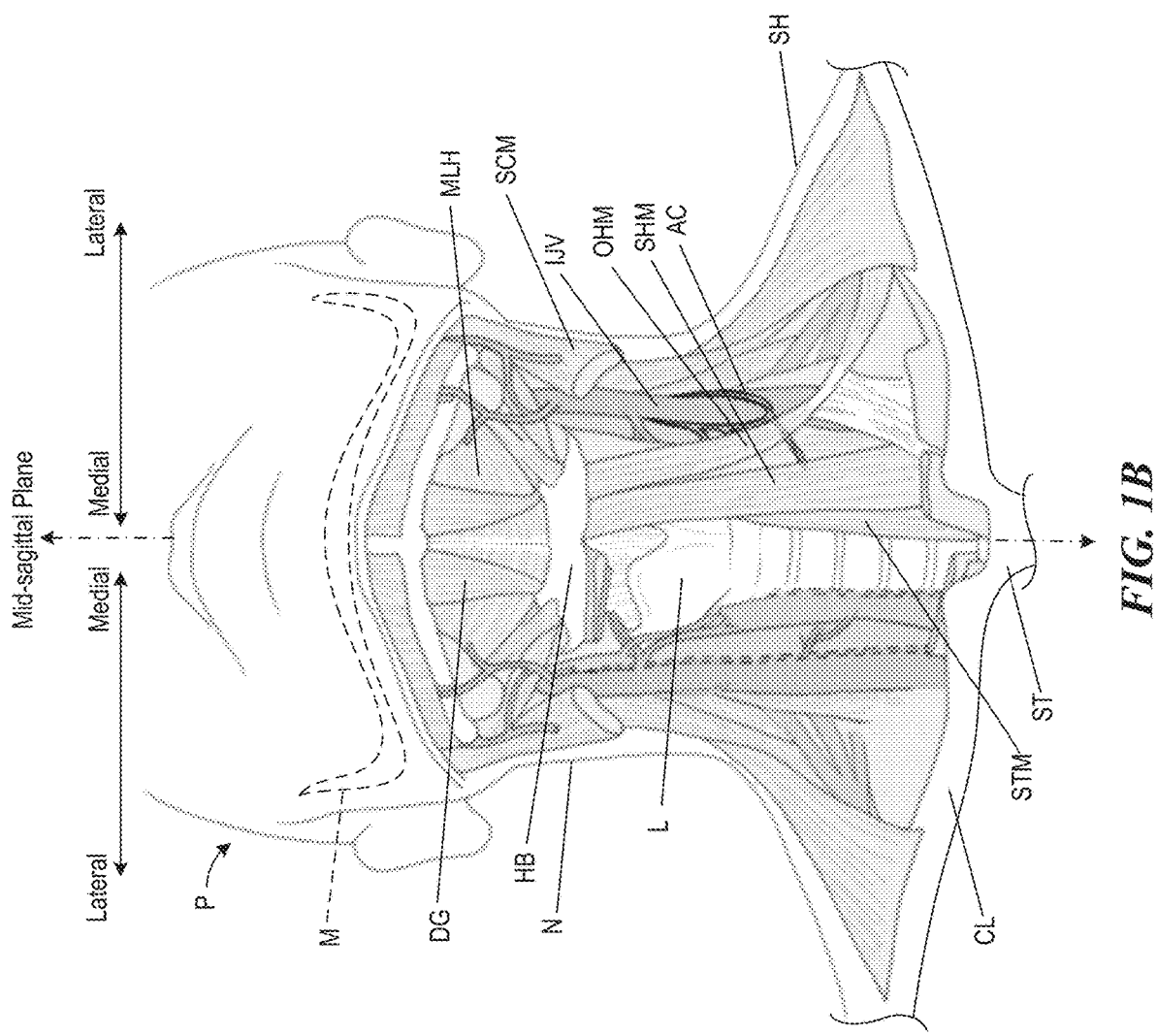
FIG. 1B is a partially schematic illustration of representative neural structures and musculature of the patient's low jaw and neck.

FIG. 1B is a partially schematic illustration of representative neural structures and musculature of the patient's lower jaw and neck. The omohyoid muscle OHM extends between the hyoid bone HB and the scapula. The sternohyoid muscle SHM extends between the hyoid bone HB and the sternum ST, and the sternothyroid muscle STM extends between the sternum ST and the patient's thyroid cartilage TH. The ansa cervicalis AC, and related branches emanating from the ansa cervicalis AC, enervate the omohyoid muscle OHM, the sternohyoid muscle SHM, and the sternothyroid muscle STM. The ansa cervicalis AC can also extend at least partially parallel to and/or around the patient's internal jugular vein IJV. FIG. 1B also illustrates the patient's mandible M, mylohyoid muscle MLH, and digastric muscle DG (more specifically, the anterior belly of the digastric muscle DG), as well as the sternothyroid muscle STM, sternocleidomastoideole SCM, and the sternohyoid muscle SHM. The sternohyoid muscles SHM and the sternothyroid muscles STM extend over (e.g., anterior to) the patient's larynx L. The muscles described above are contained within the patient's oral cavity OC, neck N, and/or shoulder SH. As described in greater detail below, by positioning and activating minimally invasive electrodes at least proximate to one or more the foregoing neural structures and/or associated musculature, embodiments of the present technology can control, reduce, and/or eliminate the effects of OSA.

Figure 1C:
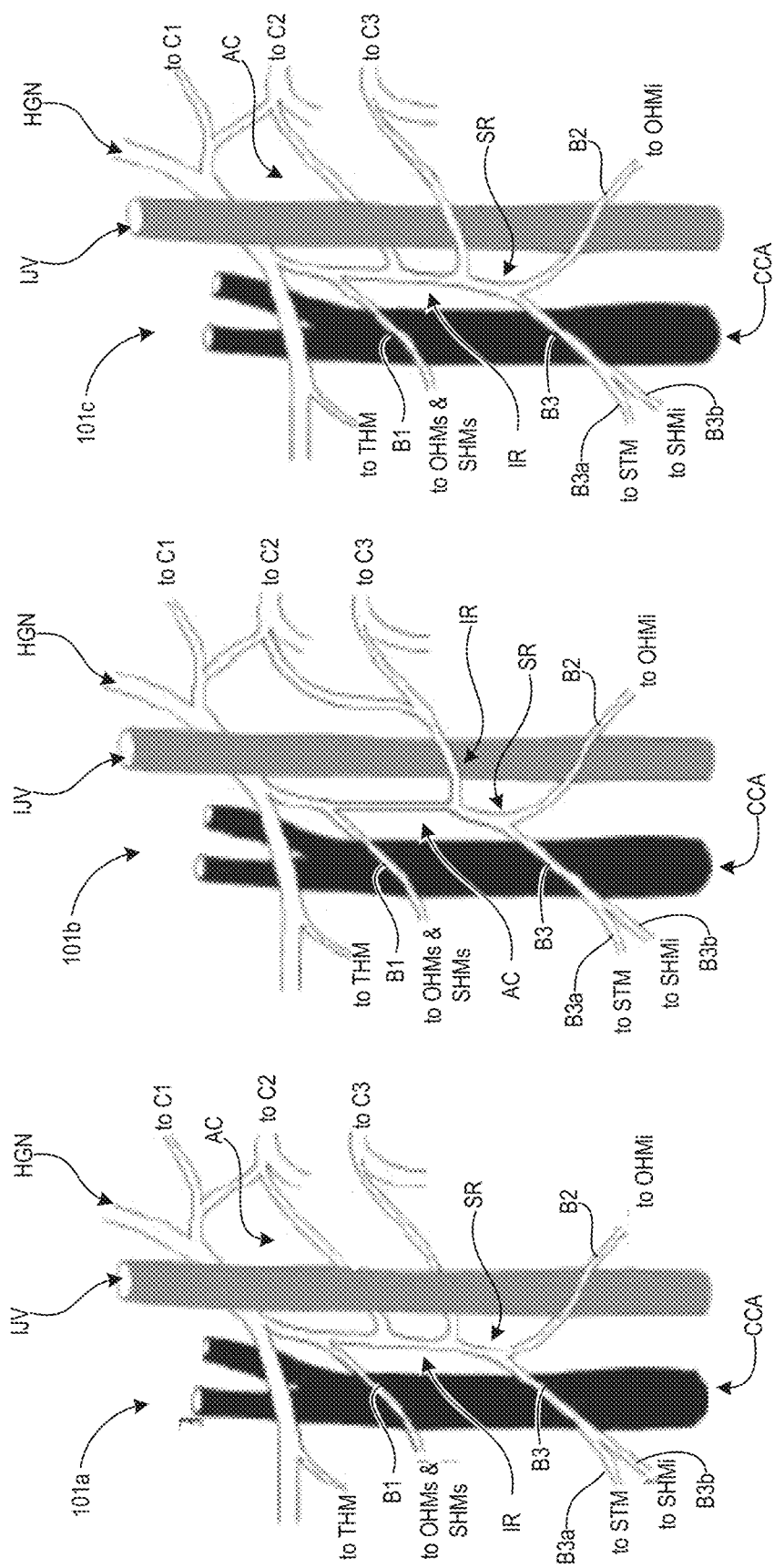
FIG. 1C is a partially schematic illustration of an ansa cervicalis nerve.

FIG. 1C is a partially schematic illustration of several arrangements of an ansa cervicalis nerve AC. Specifically, FIG. 1C illustrates a medial arrangement 101a of the ansa cervicalis nerve AC, a lateral arrangement 101b of the ansa cervicalis nerve AC, and a mixed type 101c of the ansa cervicalis nerve AC. In each of these arrangements, the ansa cervicalis nerve AC includes a superior root SR, an inferior root IR, a first branch B1 innervating a superior belly of the omohyoid muscle OHMs and a superior belly of the sternohyoid muscle SHMs, a second branch B2 innervating an inferior belly of the omohyoid muscle OHMi, and a third branch B3 to both the sternohyoid muscle SHM and the sternothyroid muscle STM. More specifically, the third branch B3 can bifurcate/split into a first sub-branch B3a innervating the sternothyroid muscle STM and a second sub-branch B3b innervating an inferior belly of the sternohyoid muscle SHMi. The hypoglossal nerve HGN, cranial nerves C1-C3, internal jugular vein IJV, and common carotid artery CCA are shown for context. In the medial arrangement 101a (left), the inferior root IR extends posterior to (e.g., behind) the internal jugular vein IJV. In the lateral arrangement 101b (middle), the inferior root IR is positioned anterior to (e.g., in front of) the internal jugular vein IJV. In the mixed arrangement 101c (right), the inferior root IR is positioned at least partially around the internal jugular vein IJV, with an upper/superior portion of the inferior root IR extending posterior to the internal jugular vein IJV and a lower/inferior portion of the inferior root IR extending anterior to the internal jugular vein IJV. In each of these arrangements 101a-c, the position and/or location of the third branch B3 and the corresponding sub-branches B3a and B3b is expected to be at least generally similar or the same. As such, the third branch B3 and/or the sub-branches thereof B3a, B3b are particular target locations of the present technology at least because these branches are expected to be easier to identify and/or because the third branch B3 innervates multiple infrahyoid strap muscles (e.g., the sternothyroid muscle STM and the inferior belly of the sternohyoid muscle SHMi). However, those of ordinary skill in the art will understand that, in practice, the systems and methods of the present technology can still be used to address OSA in such patients by targeting other portions of the ansa cervicalis nerve AC.

Figure 1D:
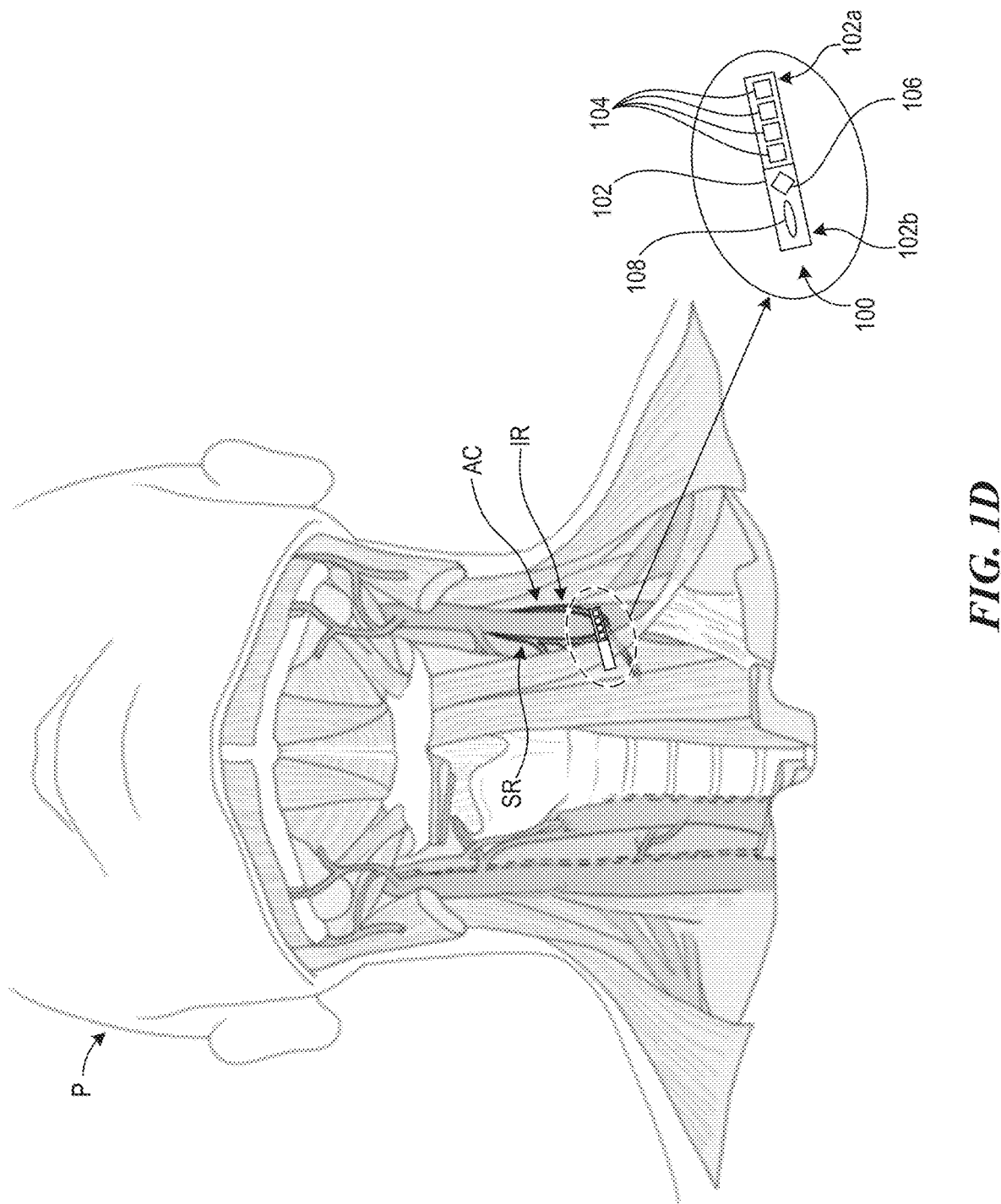
FIG. 1D is a front sectional view depicting a portion of a patient's neck and lower jaw and a signal delivery device positioned in accordance with embodiments of the present technology.

FIG. 1D is a partially schematic illustration of representative neural structures and musculature of the patient's lower jaw and neck and a signal delivery device 100 positioned in accordance with embodiments of the present technology. The signal delivery device 100 (shown schematically) can include a housing 102, one or more electrodes 104, a signal generator 106, and an antenna 108. The housing 102 can include a first end portion 102a and a second end portion 102b opposite the first end portion 102a. Individual ones of the electrodes 104 can be positioned on and/or at least partially around the housing 102, e.g., the first end portion 102a of the housing 102. In some embodiment, the electrodes 104 can be masked (e.g., circumferentially masked), segmented (e.g., circumferentially segmented and individually addressable), directional, at least partially covered, and/or otherwise configured to direct the electrical field in specific direction(s). The signal generator 106 and the antenna 108 can be positioned at least partially or fully within the housing 102, e.g., at or near the second end portion 102b of the housing 102. The signal delivery device 100 can be secured in position at least proximate to or within the one or more target neural and/or muscle structures using one or more anchors, suture threads, and/or other suitable devices.

In operation, the antenna 108 can be configured to wirelessly receive power signals (e.g., radiofrequency "RF", inductive, etc.) from one or more devices external to the patient P, such as one or more wearable devices. An RF power signal, or at least a portion of the RF power signal, can have a frequency in a range of from about 300 MHz to about 6 GHz, e.g., from about 400 MHz to about 2.5 GHZ, from about 600 MHz to about 2.45 GHz, from about 900 MHz to about 1.2 GHZ, or any other intermediate frequency or frequency range. An inductive power signal, or at least a portion of the inductive power signal, can have a frequency in a range of from about 100 kHz to about 14 MHz, including, e.g., about 135.7 kHz, about 6.5 MHz, about 13.5 MHz, and/or another suitable frequency and/or range of frequencies. In these and/or other embodiments, the wireless power signal, or at least a portion of the wireless power signal, can have a frequency or frequency range in the industrial, scientific, and medical band ("ISM band") of frequencies.

The power received at the antenna 108 can be transmitted to the signal generator 106, which can use the power to generate one or more electrical pulses or signals. In at least some embodiments, the power (e.g., AC power) received at the antenna 108 is rectified to DC (via, e.g., an AC-DC converter), which is then transmitted to a DC-DC converter, charge pump, and/or transformer. In some embodiments, the power is converted to pulses having a frequency in a range from about 10 Hz to about 500 Hz, such as from about 30 Hz to about 300 Hz. In other embodiments, the pulses can be delivered at a higher frequency (e.g., 10 kHz or more), and/or in the form of bursts. The amplitude of the signal can be from about 1 mV to about 5 V (and in particular embodiments, 1 V to 2 V) in a voltage-controlled system, or from about 0.5 mA to about 12 mA in a current-controlled system. The pulse width can be between about 10 us and about 1000 μs, such as at least 10 μs, 50 μs, 100 μs, 150 μs, 250 μs, 500 μs, or another suitable pulse width. In the illustrated embodiment, all the signal generation functions are performed by the signal generator 106, and in other embodiments, some signal generation functions may be performed by external elements. The signal generation functions and signal delivery functions may be performed by a single signal delivery device, or multiple devices.

The signals generated by the signal generator 106 can be transmitted to one or more of the electrodes 104, which can in turn deliver the signals to the target neural and/or muscle structures. The electrical field(s) resulting from the currents transmitted by the electrodes 104 produces the desired effect (e.g., excitation and/or inhibition) at the target nerve. In at least some embodiments, the signal delivery device 100 need not include any on-board power storage elements (e.g., power capacitors and/or batteries), or any power storage elements having a storage capacity greater than 0.5 seconds, so as to reduce system volume. In other embodiments, the signal delivery device 100 can include one or more small charge storage devices (e.g., low voltage, high capacitance capacitors, solid state batteries, and/or the like) that are compatible with the overall compact shape of the signal delivery device 100, and have a total charge storage capacity of no more than 1 second, 5 seconds, 10 seconds, 15 second, 20 seconds, 25 seconds, 30 seconds, 1 minute, 2 minutes, 5 minutes, any time period therebetween, or another suitable time period, depending on the embodiment. In further embodiments, the signal delivery device 100 includes one or more power storage elements configured to storage a charge for extended periods of time. Such signal delivery devices 100 can be configured for use with wearable devices that omit power transmission devices. In at least some embodiments, the modulation signal delivered to the patient can be delivered via a dipole formed by two of the electrodes 104. In other embodiments, the signal delivery device 100 can be a monopole, with at least a portion of the housing 102 (e.g., the first end portion 102a of the housing 102) forming a ground or return electrode and/or with the ground electrode positioned elsewhere (e.g., subcutaneously at another location, external to the patient, etc.). In these and other embodiments, the modulation signal can include a monophasic waveform, a biphasic and/or charge balanced waveform, and/or another suitable waveform.

The signal delivery device 100 can include additional onboard components and/or functionality. In some embodiments, the signal delivery device 100 includes one or more sensors. The sensors can include motion sensors configured to detect vibration induced by apnea/snoring/hypopnea, movement, and/or the patient's body orientation. The sensors can also include respiratory rate sensors, respiratory amplitude sensors, heart rate sensors, SpO2 sensors, and/or one or more other sensors configured to detect information associated with the patient's breathing and/or sleep state. Data generated by the sensors can be processed onboard the signal delivery device 100 and/or communicated to an external control unit, e.g., to provide closed loop control of the signal delivery device 100 and/or generation of the modulation signal based, at least in part, on the sensed data.

Although a single signal delivery device 100 is shown in FIG. 1D, in some embodiments one or more additional signal delivery devices can be positioned to deliver a modulation signal to (i) other portions of the ansa cervicalis AC, (ii) one or more of the branches of the ansa cervicalis, and/or (iii) one or more of the patient's infrahyoid strap muscles. Additional details regarding signal delivery device positioning are described below with reference to FIGS. 2A-9B.

3. Representative Insertion Paths and Target Tissues

Several modulation targets and implantation techniques are described and/or illustrated with reference to FIGS. 2A-9B. For the purpose of clarity, these modulation targets and implantation techniques are shown with reference to a left or right side of the patient P's anatomy, for example, a first or left ansa cervicalis nerve of the patient P and/or a first or left one of the infrahyoid strap muscles. It will be appreciated, however, that at least some or all of the modulation targets and/or implantation techniques described and/or illustrated with reference to FIGS. 2A-9B are equally suitable for application to the other side of the patient's anatomy, for example, the second or right ansa cervicalis nerve of the patient P and/or the second or right one of the infrahyoid strap muscles. Additionally, at least some of the modulation targets and/or implantation techniques can be used for bilateral signal delivery, for example, to apply a first modulation signal to a first modulation target on a first side of the patient P at a first time, and to apply a second modulation signal to a second modulation target on a side of the patient P at the same or different time. The second modulation signal can be the same or different than the first modulation signal. In some embodiments, the first and second modulation targets can be corresponding left and right portions of the patient's anatomy, such as first and second portions of the left and right ansa cervicalis nerves. In other embodiments, the first and second modulation targets can be different, such as the left ansa cervicalis nerve and an infrahyoid strap muscle on a right side of the patient.

Current surgical device placement methods for treating OSA target the hypoglossal nerve, but roughly 35-45% of patients receive little to no positive impact from the therapy/signal delivered to this target. Moreover, many patients who are considered responders to hypoglossal nerve modulation still have a residual apnea-hypopnea index ("AHI"). Such patients experience only a 50-70% reduction in their AHI, even after optimizing modulation settings, indicating that these patients still experience apneas and/or hypopneas during and/or after the hypoglossal nerve modulation therapy. These patients also may experience unwanted arousals, tongue abrasion, snoring, and/or other side effects of hypoglossal nerve modulation therapy that are expected to reduce patient compliance with the therapy—for example, current methods have less than 80% user compliance.

Furthermore, current OSA treatment methods stimulate the base of the posterior portion of the tongue but do not stiffen the rest of the airway. While a large number of OSA patients' airways exhibit retrolingual collapse (e.g., collapse at the tongue base), almost all patients with OSA have retropalatal (e.g., velopharyngeal and/or oropharyngeal) tissue collapse. Hypoglossal nerve modulation may not be effective at increasing airway patency at the retropalatal levels in all patients. Ansa cervicalis AC modulation is expected to improve (e.g., reduce) airway collapsibility in the retropalatal region without impacting the ability of hypoglossal nerve modulation to reduce or prevent retrolingual collapse. Accordingly, ansa cervicalis AC modulation, alone or in combination with hypoglossal nerve modulation, is expected to provide a therapeutic solution for a wider range of collapse sites in the upper airway, resulting in (1) more effective therapy for patients whose collapse pattern (e.g., retropalatal) would not be completely targeted by hypoglossal nerve modulation alone, and (2) a broadened potential population for whom neuromodulation can be an effective therapy by targeting an additional collapse site. Although ansa cervicalis modulation is, on its own, expected to improve or even correct breathing obstructions, the combination of ansa cervicalis AC and hypoglossal nerve modulation is expected to provide a multiplicative effect and/or otherwise enhance a magnitude of the therapy (e.g., a greater level of collapsibility can be treated) compared to only ansa cervicalis AC modulation therapy or only hypoglossal nerve modulation therapy. This could allow for treatment of higher body mass index (BMI) patients, and/or for treatment of patients with a more collapsible airway, such as those with a higher therapeutic CPAP value.

Stimulating the ansa cervicalis AC and/or one or more of the patient's infrahyoid strap muscles is expected to move the hyoid bone inferiorly by contracting the infrahyoid strap muscles, resulting in caudal traction. Caudal traction has been documented as a mechanism to stiffen one or more tissues (e.g., the glottis, vocal cords, etc.) defining the patient's upper airway and/or otherwise increase upper airway stability to at least partially address the symptoms of OSA. For example, lowering the hyoid bone can cause the tongue, or at least a posterior portion of the tongue, to change its position relative to the patient's airway without, or generally without, inducing a contraction of the tongue muscles. For example, lowering the hyoid bone can stretch the tongue inferiorly and thereby open (or further open) the patient's airway (or at least a retrolingual portion of the patient's airway) to increase airflow therethrough. Also, stimulating the hypoglossal nerve and/or the genioglossus muscle is expected to contract the posterior portion of the tongue. Pharyngeal wall stiffening is another impact that infrahyoid strap muscle contraction has on the upper airway, which can be complementary to caudal traction. Accordingly, on its own, ansa cervicalis modulation can improve or even fully-restore a patient's airflow obstructions.

Combination therapy (e.g., targeting the ansa cervicalis AC and the hypoglossal nerve, and/or one or more of the muscles innervated by these nerves) is expected to provide multiple physiological responses that reduce or prevent obstruction of the patient's airway. For example, the use of combined infrahyoid strap muscle contraction and genioglossus contraction is expected to prevent, or at least partially prevent, multi-site collapse by addressing retropalatal collapse and retrolingual collapse, e.g., simultaneously and/or with complementary physiologic responses. Such infrahyoid strap muscle contraction can be achieved via, e.g., ansa cervicalis AC modulation, infrahyoid strap muscle modulation, and/or motor plate modulation, and such genioglossus contraction can be achieved by hypoglossal nerve modulation, direct genioglossus muscle modulation, and/or motor plate modulation. Combination therapy is therefore expected to improve results for patients who already respond to single target modulation (e.g., ansa cervicalis or hypoglossal nerve) but still have residual breathing obstructions (e.g., after ansa cervicalis modulation, residual retrolingual collapse; after hypoglossal nerve stimulation, retropalatal narrowing/collapse and/or residual snoring/AHI, etc.) For example, embodiments of the present technology are expected to decrease the number and/or the frequency of apnea and/or hypopnea events experienced by the patient during a period of time, such as during and/or after modulation signal delivery. Additionally, or alternatively, multi-site signal delivery is expected to increase the potential patient responder population to include patients who would not otherwise respond to single target modulation alone. This includes patients that are already received hypoglossal nerve stimulation but have a primary retropalatal (e.g., velopharyngeal) collapse, no soft palate coupling, a BMI>32, and/or a complete concentric collapse of the airway.

In some embodiment, the combination of ansa cervicalis AC and hypoglossal nerve modulation is expected to reduce patient arousal, e.g., by reducing or preventing overmodulation of the tongue base (which may be conducted to entrain the soft palate). For example, positioning signal delivery devices to target multiple nerves/muscle groups can provide effective therapy while operating one or more of the devices at an amplitude that is lower than would be required if only one nerve/muscle group was targeted. Additionally, or alternatively, positioning multiple signal delivery devices to target select nerves/muscles can provide effective therapy while only inducing a partial contraction/motor response of one or more of the associated muscles (e.g., stiffening the associated muscles or otherwise improving their tone without, or substantially without, inducing tetany or a full contraction). By reducing the effective therapeutic amplitude and/or motor response at one or more target modulation sites, embodiments of the present technology are expected to generate a lower patient arousal rate without or substantially without jeopardizing an effective physiological response. As a result, this approach can increase patient compliance, overall therapy efficacy, and/or the patient's sleep quality.

Additional details regarding techniques for placing signal delivery devices to deliver modulation signals to the ansa cervicalis nerve are described with reference to FIGS. 2A-9B. Additional details regarding placing signal delivery devices to deliver modulation signals to the hypoglossal nerve are described in U.S. application Ser. No. 18/393,537, filed Dec. 21, 2023, the entirety of which is hereby incorporated by reference herein.

Figure 2A:
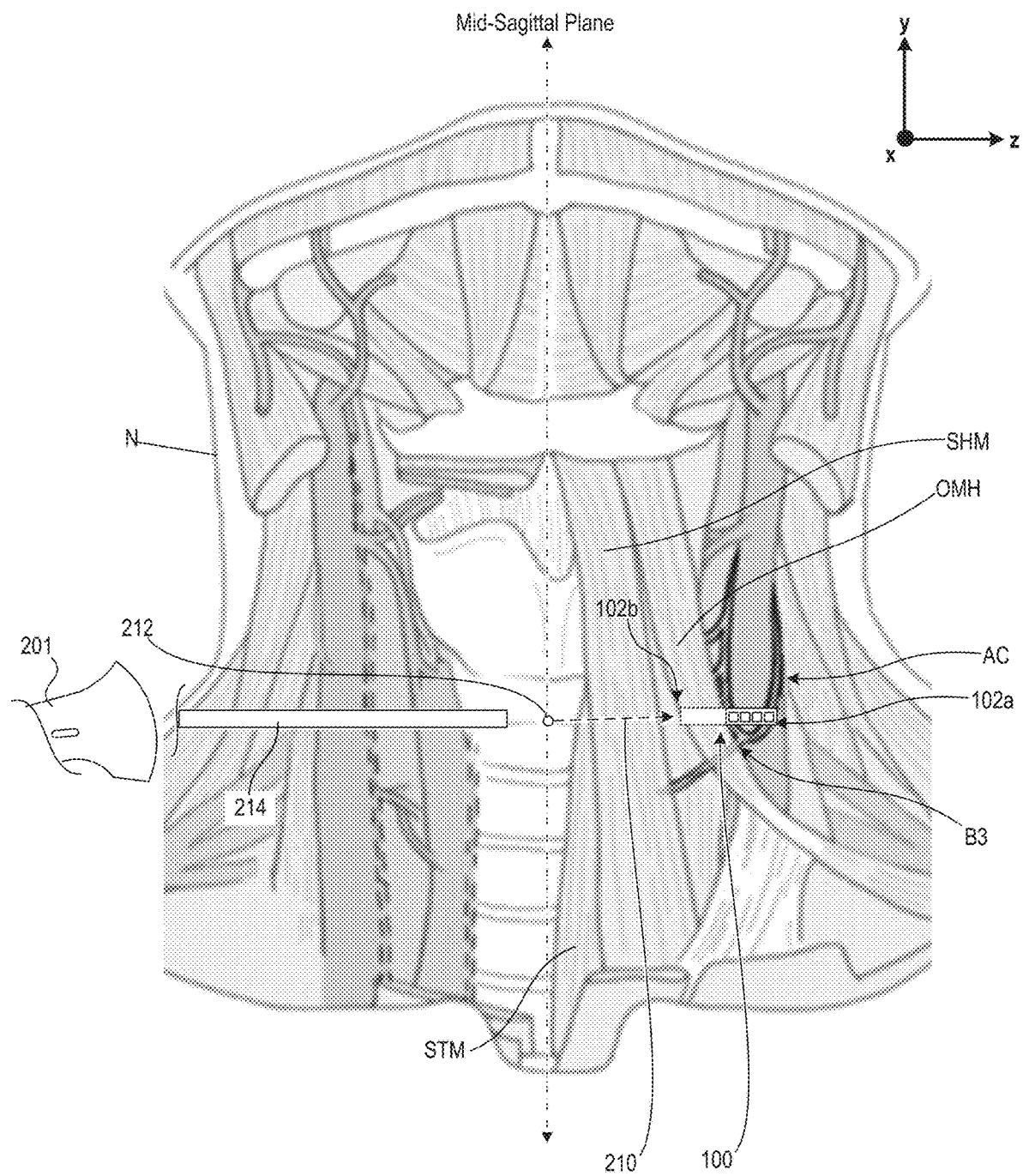
FIG. 2A is a front sectional view of a portion of a patient's neck and lower jaw depicting a signal delivery device insertion path in accordance with embodiments of the present technology.

FIG. 2A is a side sectional view of a portion of a patient's upper airway depicting the signal delivery device 100 at a target location at least proximate to one or more target tissues in accordance with embodiments of the present technology. In the illustrated embodiment, the target location is superior to the third branch B3 of the ansa cervicalis AC. In these and/or other embodiments, the target location can be at least proximate to one or more other portions of the ansa cervicalis AC. When positioned at least proximate to the target tissue, the signal delivery device 100 can be between about 10 mm and about 0.01 mm from the target tissue, such as (i) within up to 9 mm, 8 mm, 7 mm, 6 mm, 5 mm, 4 mm, 3 mm, 2 mm, 1 mm, or 0.1 mm from the target tissue, (ii) in contact with at least a portion of the target tissue, (iii) within any distance therebetween, or (iv) within another suitable distance from the target tissue.

The signal delivery device 100 can be positioned at the target location via an insertion path 210 extending in a medial-to-lateral direction and posteriorly toward the target location, e.g., from at least proximate to a midline or mid-sagittal plane of the patient P. One or more of the electrodes 104 can be positioned to deliver the signal to target tissue at or at least proximate to the ansa cervicalis nerve, and delivering the signal to the target tissue can cause caudal traction and/or otherwise address the patient's OSA.

In the illustrated embodiment, the insertion path 210 is used to position the signal delivery device 100 perpendicular, or at least generally perpendicular, to the mid-sagittal plane, such as parallel or at least generally parallel to a transverse or x-z plane. In other embodiments, the insertion path 210 can be used to position the signal delivery device 100 in an orientation such that at least a component (e.g., a vector component) of the orientation is aligned along an inferior-superior/cranial-caudal axis. In such embodiments, the signal delivery device 100 is not positioned solely parallel to the x-z plane. Instead, a vector component (e.g., a significant vector component) of the orientation of the signal delivery device 100 can be aligned along the y-axis. For example, as described in greater detail below with reference to FIGS. 5A and 5B, the first end portion 102a of the signal delivery device 100 can be positioned superior to the second end portion 102b of the signal delivery device 100, or the second end portion 102b can be positioned superior to the first end portion 102a.

In some embodiments, an insertion point or opening 212 can be formed in the patient's neck N, such as at least proximate to the mid-sagittal plane, and the signal delivery device 100 can be moved through the opening 212 and along the insertion path 210. In the illustrated embodiment, the opening 212 is a percutaneous opening formed using a percutaneous or other minimally invasive insertion tool 214, such as a needle (e.g., a percutaneous injection needle), stylet, introducer, dilator, and/or trocar, without performing a dissection of the submental SM region. Additionally, or alternatively, the percutaneous insertion tool 214 can be used to position the signal delivery device 100 within the patient, for example, by projecting the signal delivery device 100 outwardly from within the percutaneous insertion tool 214 or otherwise releasing the signal delivery device 100 from the percutaneous insertion tool 214 when the signal delivery device 100 is positioned at least proximate to the target location.

At least a portion of the signal delivery device 100 (e.g., the second end portion 102b) can be positioned posterior to one or more of the patient's infrahyoid strap muscles (e.g., the sternohyoid muscle SHM, the sternothyroid muscle STM, and/or the omohyoid muscle OHM). For example, the opening 212 can be formed at or near the mid-sagittal plane, and the insertion path 210 can extend posterior to one or more of the sternohyoid muscles SGM, the sternothyroid muscles STM, and/or the omohyoid muscles OHM, without, or substantially without, penetrating through one or more of the infrahyoid strap muscles. Additionally, or alternatively, the insertion path 210 can extend anterior to one or more of the sternohyoid muscles SHM, the sternothyroid muscles STM, and/or the omohyoid muscles OHM. In these and/or other embodiments, the insertion path 210 can extend between the sternohyoid muscle SHM and the sternothyroid muscle STM, and/or between the sternohyoid muscle and the omohyoid muscle OHM. In some embodiments, all or a portion of the signal delivery device 100 can be positioned between and/or within individual ones of the infrahyoid strap muscles.

FIG. 2A also schematically illustrates a portion of a representative ultrasound probe 201, which can be used to aid in the process identifying where to form the opening 212, identifying the target location, moving the signal delivery device 100 along the insertion path 210, and/or otherwise positioning the signal delivery device 100 at least proximate to the target location. The ultrasound probe 201 can be used to visualize the target location, the signal delivery device 100, and/or the percutaneous insertion tool 214 before, during, and/or after the procedure to position the signal delivery device 100 at least proximate to the target location. In such embodiments, aligning the orientations of the signal delivery device 100 and the ultrasound probe 201 is expected to increase the speed and/or accuracy with which the signal delivery device 100 is positioned. In these and other embodiments, the ultrasound probe 201 can be used to guide the signal delivery device 100 to the target location. The signal delivery device 100 (or, in some embodiments, the insertion tool 214) can deliver a modulation signal during all or a portion of the implantation process so that a practitioner can observe the patient's response to the modulation signal, e.g., to confirm that the signal delivery device 100 is at or near the target location and/or to inform further adjustments to the positioning of the signal delivery device 100. This is described in greater detail in U.S. application Ser. No. 17/666,464 and U.S. Prov. application Ser. No. 18/104,739, the entireties of which are hereby incorporated by reference herein.

Although the insertion path 210 illustrated in FIG. 2A extends in a medial-to-lateral direction, in other embodiments the insertion path 210 can extend in a lateral-to-medial direction, e.g., in a direction opposite the illustrated insertion path 210 and/or toward the patient's mid-sagittal plane. In such embodiments, the opening 212 can be formed at a position spaced laterally from the target location.

Figure 2B:
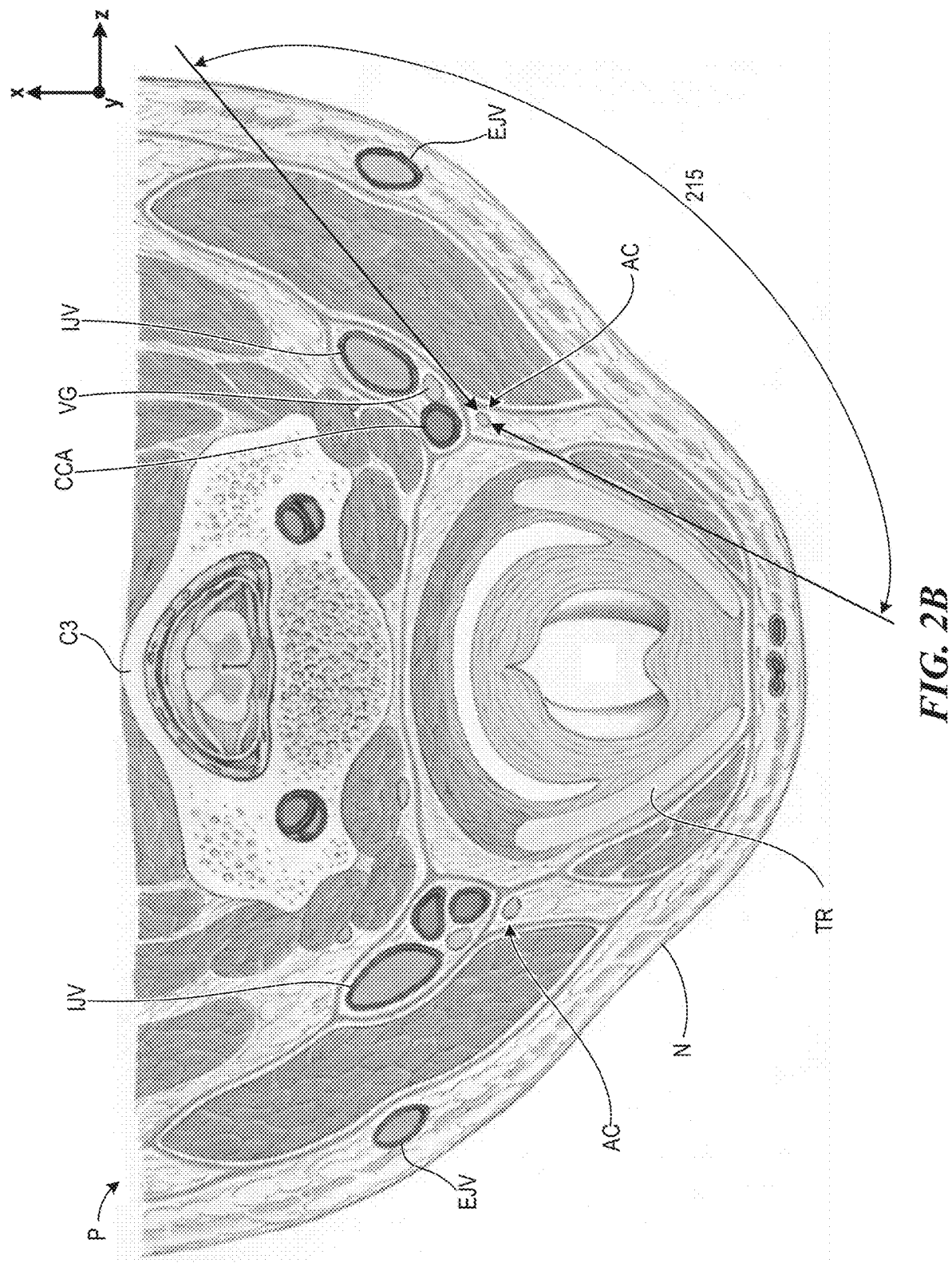
FIG. 2B is a transverse sectional view depicting a range of signal delivery device insertion paths in accordance with embodiments of the present technology.

FIG. 2B is a transverse section view through the patient's neck N at the third cervical vertebra C3, and illustrating one example of an angular insertion range 215 in accordance with embodiments of the present technology. The insertion range 215 can be determined with respect to a sagittal or x-y plane of the patient P, a coronal or y-z plane of the patient P, and/or one or more other suitable anatomical structures and/or reference features of the patient P. For a given target location, such as the ansa cervicalis AC, the patient's trachea TR can at least partially define a medial-most limit to the range of insertion paths 215. In the illustrated embodiment the internal jugular vein IJV defines a lateral-most limit to the range of insertion paths 215, but in other embodiments the external jugular vein EJV, the common carotid artery CCA, and/or the vagus nerve VG can at least partially define the lateral-most limit to the range of insertion paths 215. The insertion range 215 can be greater or less than the illustrated insertion range at different vertebral levels (e.g., C2, C4, C5, C6, C7, TI, etc.). The insertion range 215 can be angle of up to 180 degrees, 170 degrees, 135 degrees, 90 degrees, 45 degrees, 15 degrees, 5 degrees, or any angular range there between. In some embodiments, a preferred insertion path is within 5 degrees, 10 degrees, 20 degrees, 30 degrees, 45 degrees, or 90 degrees of the medial-most or lateral-most limit of the range of insertion paths 215. Although the insertion range 215 is illustrated on a left side of the patient P, those of ordinary skill in the art will understand that an at least generally similar or a same insertion range can be used to position a signal delivery device on a right side of the patient P.

Figure 2C:
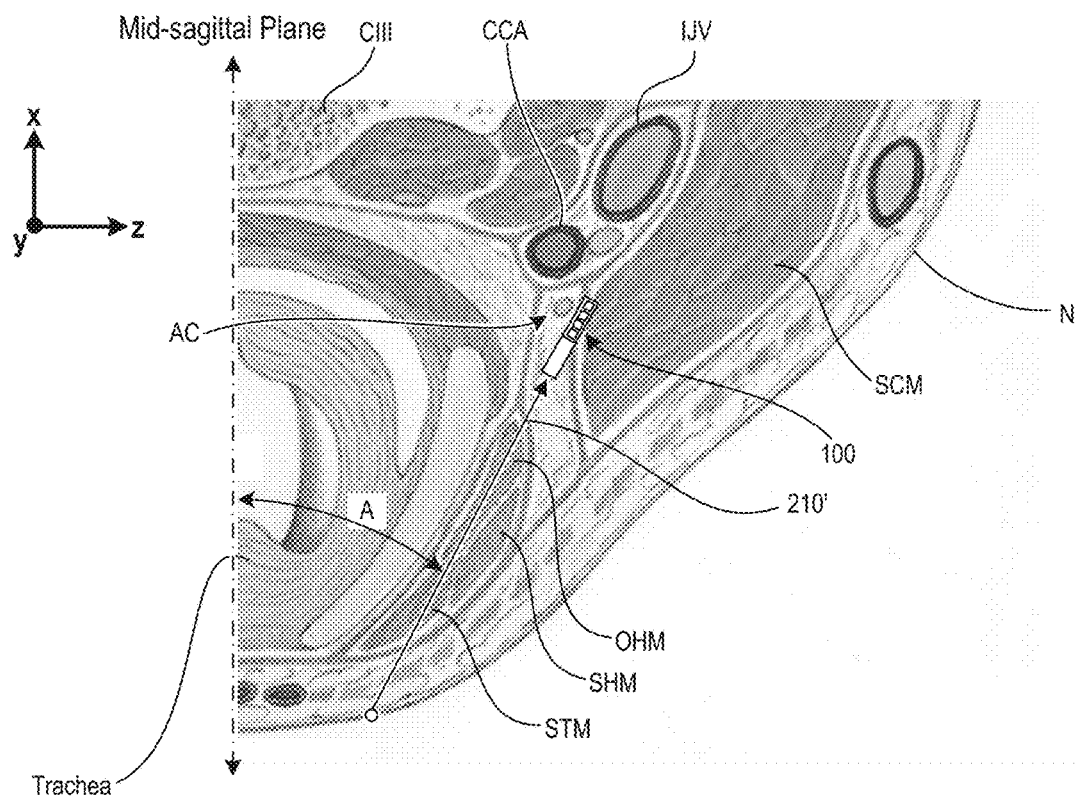
FIGS. 2C-2E are transverse sectional views depicting respective signal delivery device insertion paths in accordance with embodiments of the present technology.

FIG. 2C is a transverse sectional view depicting the insertion path 210' in accordance with embodiments of the present technology. The insertion path 210 can be a linear path, or at least generally linear insertion path, within the angular insertion range 215 of FIG. 2B. For example, the insertion path 210 can be at an angle A (in a transverse or x-z plane and/or relative to the mid-sagittal plane) of between about 0 degrees and about 135 degrees, such as between about 45 degrees and about 80 degrees, between about 60 degrees and about 80 degrees, or other angles that avoid the trachea, the internal jugular vein IJV, the external jugular vein EJV, the common carotid artery CCA, and/or the vagus nerve VG in a specific patient. The insertion path 210 can extend at least partially or fully through one or more of the infrahyoid strap muscles (e.g., the sternohyoid SHM, the sternothyroid STM, and/or the omohyoid OHM) and/or the sternocleidomastoideole, and/or can be used to position the signal delivery device 100 at least partially posterior to and/or within the patient's sternocleidomastoideole SCM. An at least generally linear insertion path 210 is expected to increase the speed and/or precision with which the signal delivery device 100 can be positioned (e.g., by a practitioner) at least proximate to the target location by, e.g., minimizing or eliminating the need to reorient the signal delivery device 100 during insertion. The medial-to-lateral insertion path 210 is expected to increase patient safety by, for example, reducing or preventing injury to the patient's vasculature, such as the internal jugular vein IJV. For example, as shown in FIG. 2C, the internal jugular vein IJV is located posterior to the ansa cervicalis AC, and the insertion path 210 can position the signal delivery device 100 at least proximate to the ansa cervicalis AC before the signal delivery device 100 reaches the depth at which the internal jugular vein IJV is located. Additionally, or alternatively, the angle of the insertion path 210 can be selected to bypass or otherwise avoid positioning the internal jugular vein IJV along the insertion path 210. In some embodiments, inserting and/or implanting the signal delivery device to avoid the patient's internal jugular vein IJV and/or other blood vessels can prevent, or at least partially prevent, delivering modulation signals to the patient's blood vessels that could cause undesired vasodilation and/or vasoconstriction. In some embodiments, inserting and/or implanting the signal delivery device to avoid the patient's internal jugular vein IJV and/or other blood vessels can prevent, or at least partially prevent, placement of the signal delivery device against the patient's blood vessels which, in turn, can reduce or prevent erosion or weakening of blood vessel tissue (e.g., due to contact/friction between the signal delivery and the blood vessel).

Figure 2D:
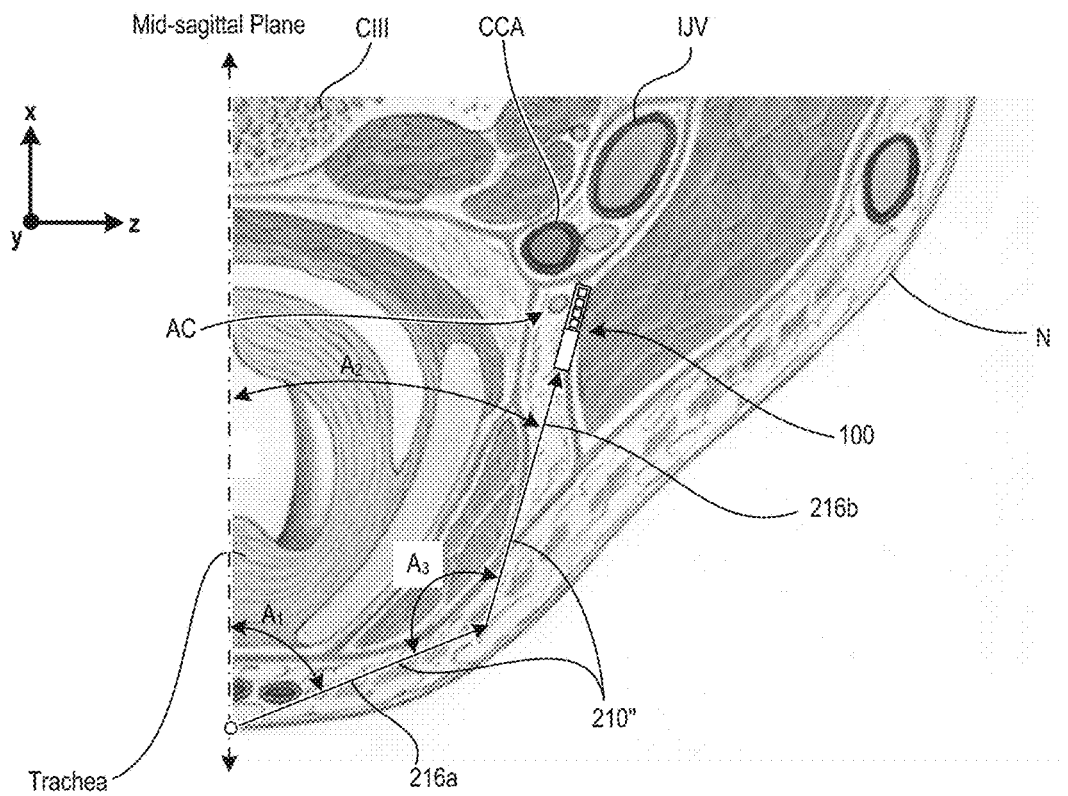

FIG. 2D is a transverse sectional view depicting another insertion path 210" in accordance with embodiments of the present technology. The insertion path 210a can include a plurality of insertion path segments or portions 216a-b that are angled relative to one another. In the illustrated embodiment, for example, the insertion path 210a includes a first or proximal path portion 216a and a second or distal path portion 216b. The first path portion 216a is at a first angle A1 in a transverse or x-z plane relative to the mid-sagittal plane. The second path portion 216b can be at a second angle A2 in a transverse or x-z plane relative to the mid-sagittal plane and/or at a third angle A3 in a transverse or x-z plane relative to the first path portion 216a. The first angle A1, the second angle A2, and/or the third angle A3 can be between about 0 degrees and about 135 degrees, such as between about 45 degrees and about 80 degrees, between about 60 degrees and about 80 degrees, any suitable angle therebetween or another suitable angle. Additionally, or alternatively, the first angle A1 can be less than or greater than the second angle A2 and/or the third angle A3, the second angle A2 can be less than or greater than the first angle A1 and/or the third angle A3, and/or the third angle A3 can be less than or greater than the first angle A1 and/or the second angle A2. Each of the insertion path portions 216a-b can be associated with a change to an orientation of the signal delivery device 100 (e.g., by a practitioner during insertion). In at least some embodiments, each of the insertion path portions 216a-b have one or more vector components that are aligned along the medial-lateral (e.g., z) axis and/or the anterior-posterior (e.g., y) axis, which is expected to (i) reduce or minimize changes to the orientation of the signal delivery device 100 during insertion and (ii) increase the speed and/or precision with which the signal delivery device 100 can be positioned at least proximate to the target location. In other embodiments, one or more of the insertion path portions can have another suitable alignment.

Figure 2E:
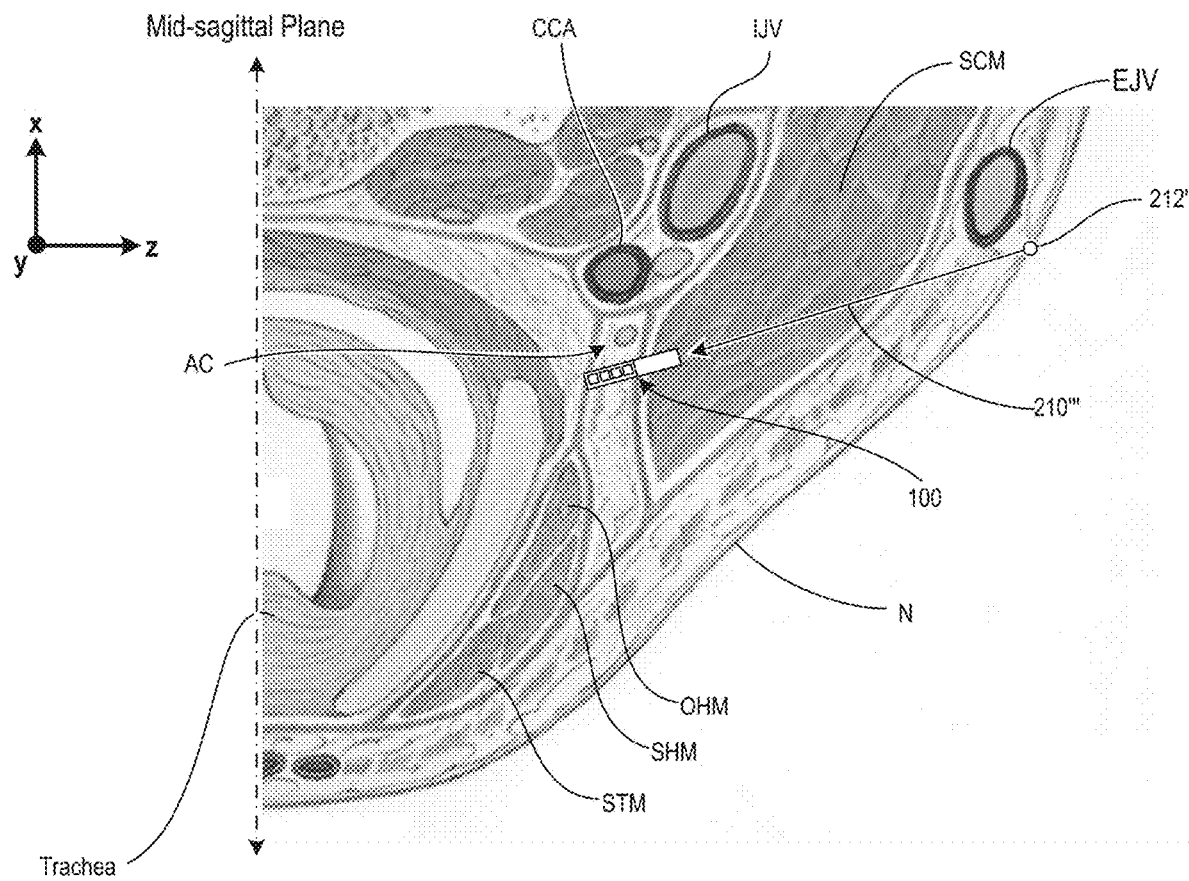

FIG. 2E is a transverse section view depicting yet another insertion path 210''' in accordance with embodiments of the present technology. The insertion path 210" can be a linear path, or at least generally linear insertion path, within the angular insertion range 215 of FIG. 2B. For example, the insertion path 210" can start at an opening 212' formed lateral and/or anterior to the external jugular vein EJV and extend inwardly, in a lateral-to-medial direction, anterior to the external jugular vein EJV and toward the ansa cervicalis AC. The insertion path 210" can extend at least partially or fully through the patient's sternocleidomastoideole SCM. Such a lateral-to-medial insertion path 210' is expected to reduce or prevent injury to the patient's vasculature and/or increase patient safety. For example, using the insertion path 210", a clinician or other use can advance the signal delivery device 100 toward the ansa cervicalis AC without, or substantially without, the insertion path 210" intersecting, or even being oriented toward, one or more of the patient's blood vessels that are proximate the ansa cervicalis AC (e.g., the external jugular vein EJV, the internal jugular vein IJV, etc.). This can simplify the navigation to the ansa cervicalis AC because, compared to insertion paths that are oriented toward patient vasculature, over-inserting the signal delivery device 100 along the insertion path 210" is less likely to pierce the patient's vasculature.

As shown in FIGS. 2C-2E, the signal delivery device 100 is positioned sub-muscularly, e.g., at least partially posteriorly to one or more of the muscles (e.g., the sternocleidomastoideole SCM) in the patient's neck N. It is believed that, with only subcutaneous placement, the signal delivery device 100 may be visible beneath the patient's skin, which patients may not find desirable, and/or the patient may be able to physically manipulate the signal delivery device 100, which may alter the position of the signal delivery device 100 relative to target tissue. However, with at least partially sub-muscular placement, such as shown in FIGS. 2C and 2D, the signal delivery device 100 is not expected to be visible and/or manipulable by the patient.

Figure 3B:
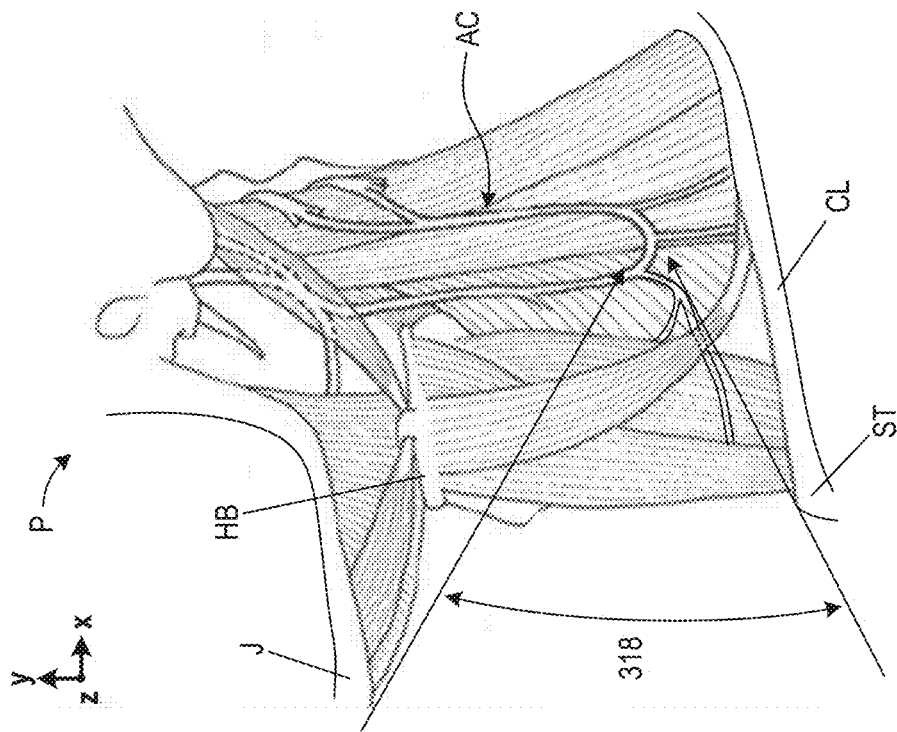
FIGS. 3A and 3B are front and side sectional views, respectively, of a portion of a patient's neck and lower jaw and depicting an angular range of medial-to-lateral signal delivery device insertion paths, each in accordance with embodiments of the present technology.
Figure 3A:
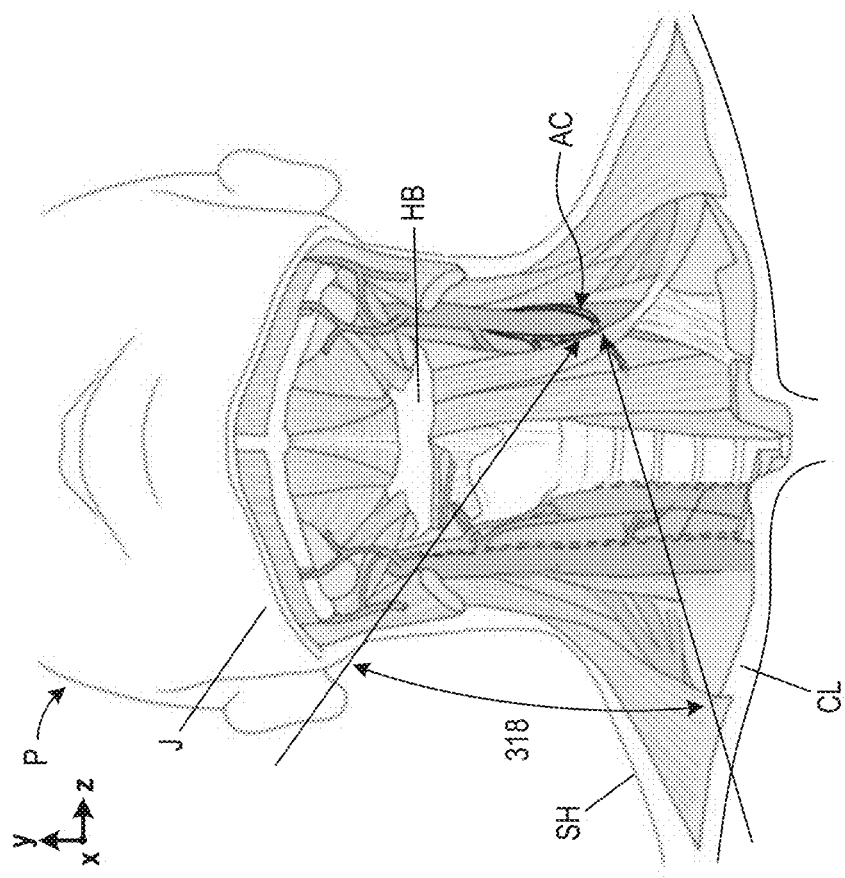

FIGS. 3A and 3B are front and side sectional views, respectively, of a portion of a patient's neck and lower jaw which illustrate an angular range 318 of an inferior-superior component of a medial-to-lateral approach for inserting the signal delivery device 100 in accordance with embodiments of a present technology. The angular range 318 can be determined with respect to, e.g., a transverse or x-z plane of the patient P, and/or one or more other suitable anatomical structures and/or reference features of the patient P. For a given target location, the patient's jaw J and/or hyoid bone HB can at least partially define a superior-most limit to the range of insertion paths 318. The clavicle CL and/or the shoulder SH can at least partially define an inferior-most limit to the range of insertion paths 318. In some embodiments, a preferred insertion path bisects the range of insertion paths 318, or is within plus or minus 20 degrees, 15 degrees, 10 degrees, 5 degrees, or 1 degree, or is at other angles that avoid the trachea TR (FIG. 2B), the internal jugular vein IJV (FIG. 2B), the external jugular vein EJV (FIG. 2B), the common carotid artery CCA (FIG. 2B), and/or the vagus nerve VG (FIG. 2B) in a specific patient. The patient's neck N and/or jaw J can be manipulated to increase the angular range 318. For example, a practitioner can rotate or roll the patient's jaw J rearwardly to increase access to the neck N and/or lower jaw. Additionally, or alternatively, by using a short-length insertion tool or needle, the practitioner can make use of a greater range of insertion paths than the angular range 318 illustrated in FIGS. 3A and 3B, e.g., including vertically aligned insertion paths and/or implantation orientations, as described in detail below with reference to FIGS. 5A and 5B.

Figure 3D:
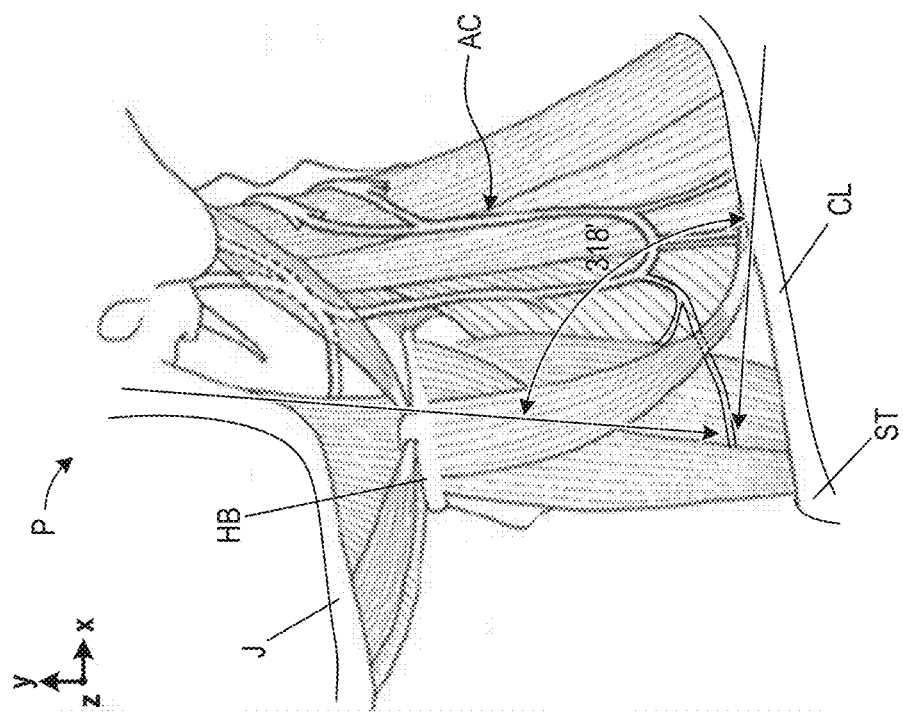
FIGS. 3C and 3D are front and side sectional views, respectively, of a portion of a patient's neck and lower jaw depicting an angular range of lateral-to-medial signal delivery device insertion paths, each in accordance with embodiments of the present technology.
Figure 3C:
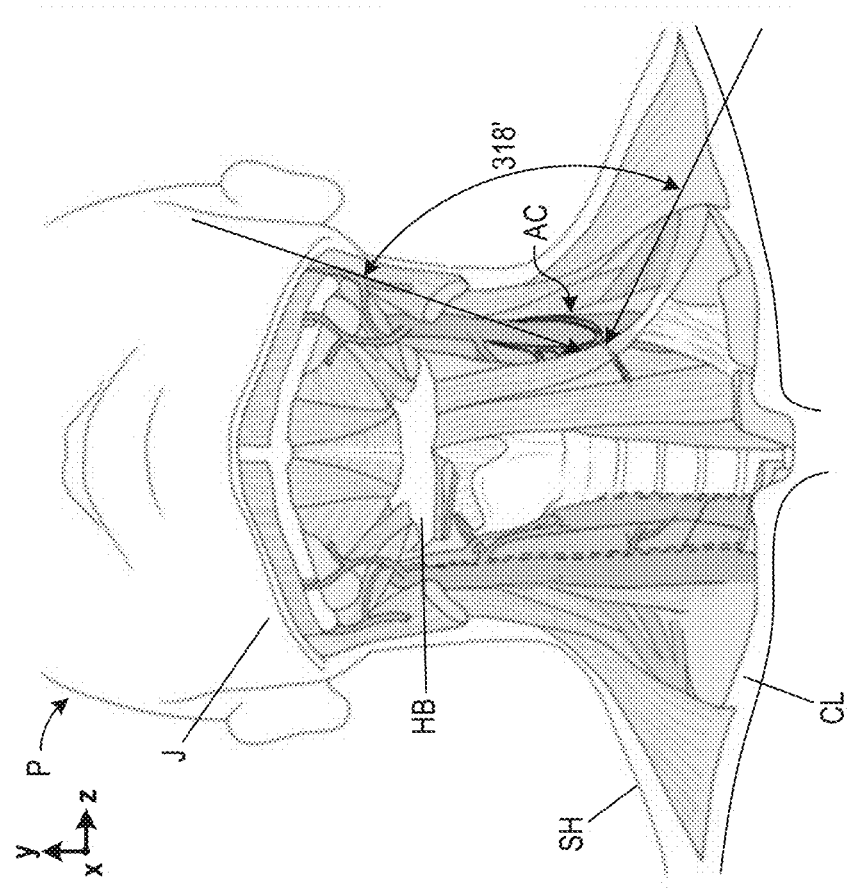

FIGS. 3C and 3D front and side sectional views, respectively, of a portion of a patient's neck and lower jaw which illustrate an angular range 318' of an inferior-superior component of a lateral-to-medial approach for inserting the signal delivery device 100 in accordance with embodiments of a present technology. The inferior-most and/or superior most bounds of the angular range for the lateral-to-medial approach can be define by at least generally similar or the same anatomy as the bounds for the medial-to-lateral approach described above with reference to FIGS. 3A and 3B. For example, for a given target location, the patient's jaw J and/or hyoid bone HB can at least partially define a superior-most limit to the range of insertion paths 318' and the clavicle CL and/or the shoulder SH can at least partially define an inferior-most limit to the range of insertion paths 318'. In some embodiments, a preferred insertion path bisects the range of insertion paths 318', or is within plus or minus 20 degrees, 15 degrees, 10 degrees, 5 degrees, or 1 degree, or is at other angles that avoid the trachea TR (FIG. 2B), the internal jugular vein IJV (FIG. 2B), the external jugular vein EJV (FIG. 2B), the common carotid artery CCA (FIG. 2B), and/or the vagus nerve VG (FIG. 2B) in a specific patient. The patient's neck N and/or jaw J can be manipulated to increase the angular range 318'. For example, a practitioner can rotate or roll the patient's jaw J rearwardly to increase access to the neck N and/or lower jaw. Additionally, or alternatively, by using a short-length insertion tool or needle, the practitioner can make use of a greater range of insertion paths than the angular range 318' illustrated in FIGS. 3C and 3D, e.g., including vertically aligned insertion paths and/or implantation orientations, as described in detail below with reference to FIGS. 5A and 5B.

FIGS. 4A-8 illustrate additional positions at which the signal delivery device 100 can be implanted. Although FIGS. 4A-8 show the signal delivery device 100 in a specific orientation and positioned at least proximate to one or more specific target tissues, those of ordinary skill in the art will understand that the signal delivery device 100 can be positioned in other orientations and/or at other target tissues.

Figure 4B:
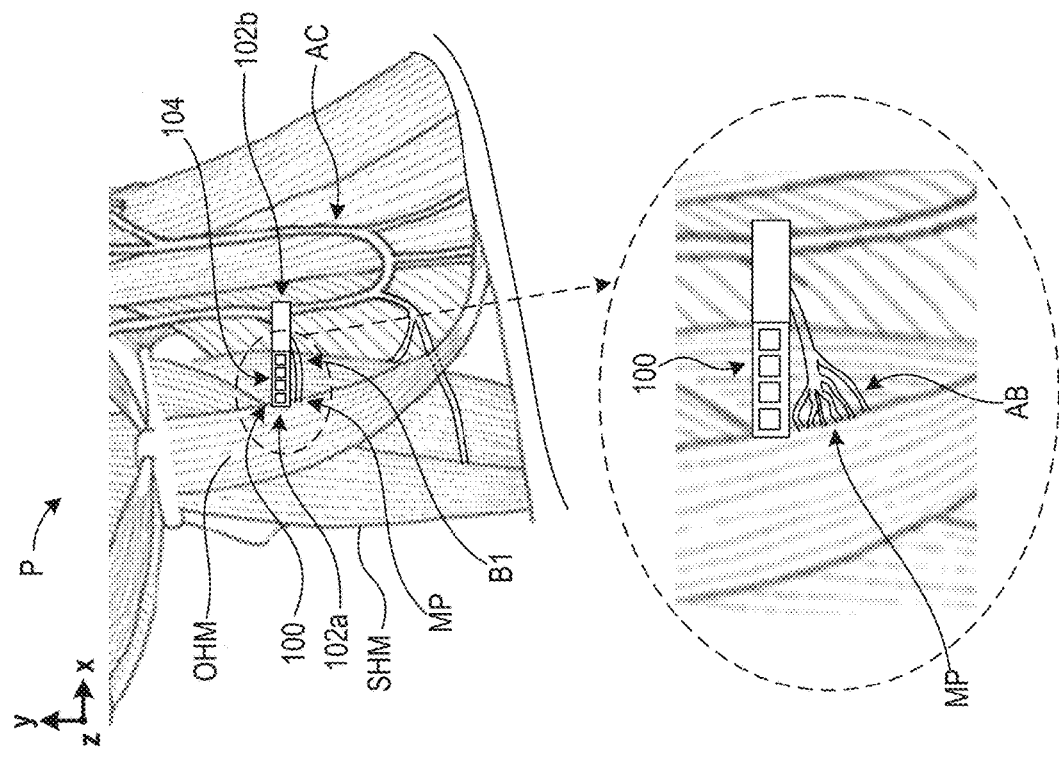
FIGS. 4A and 4B are side sectional views of a portion of a patient's neck and lower jaw and depicting respective signal delivery device implantation positions in accordance with embodiments of the present technology.
Figure 4A:
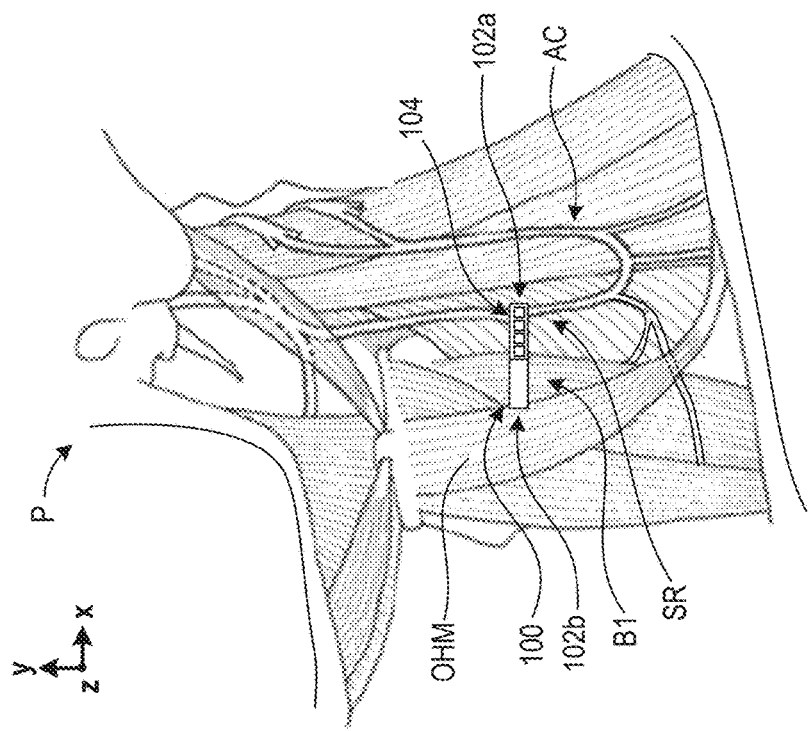

Referring to FIG. 4A, the signal delivery device 100 is in an at a least generally anterior-posterior orientation and positioned at least proximate to the superior root SR of the ansa cervicalis and/or the branch B1 of the ansa cervicalis AC innervating the superior belly of the omohyoid OHM. In this position, the signal delivery device 100 can be configured to deliver the modulation signal to at least one or both of the superior root SR and/or the branch B1 based, at least in part, on which of the electrodes 104 are activated. In the medial-lateral orientation shown in FIG. 4A, the first end portion 102a and the second end portion 102b can have the same, or at least generally similar, inferior-superior positions relative to one another so that, e.g., the orientation of the signal delivery device 100 does not include a vector component that is angled in the inferior-superior direction.

Figure 4C:
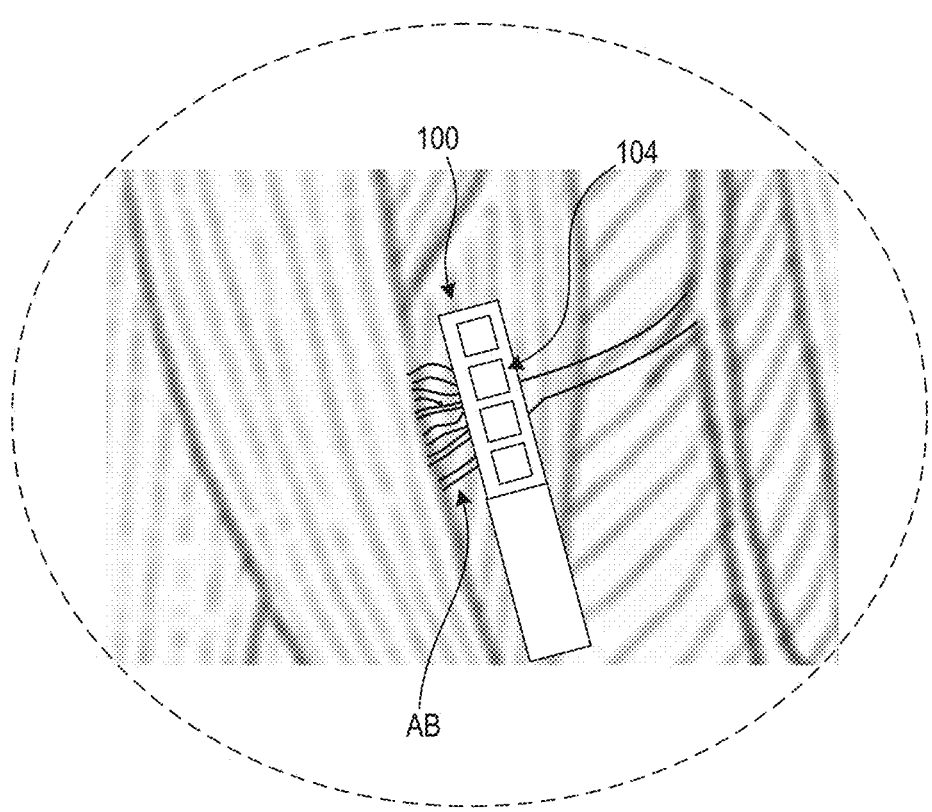
FIG. 4C is a side sectional view depicting a signal delivery device positioned in accordance with embodiments of the present technology.

Referring to FIG. 4B, the signal delivery device 100 is in a position and orientation that is at least generally similar to the position and orientation described previously with reference to FIG. 4A. However, in the anterior-posterior orientation shown in FIG. 4B, the first end portion 102a is positioned anterior to the second end portion 102b so that, e.g., the signal delivery device 100 is positioned to deliver the modulation signal to a motor point MP at which the branch B1 of the ansa cervicalis AC innervates the superior belly of the omohyoid muscle OHMs and a superior portion of the sternohyoid muscle SHM. The motor point MP is the point where the motor nerve/ansa cervicalis AC first pierces the associated muscle belly, and it is the terminal end of the motor nerve fiber which is the most sensitive location of a muscle to electrical modulation. The motor point MP can include one or more anterior branches AB which each innervate individual muscle fibers. One or more of the anterior branches AB can be independently stimulated to cause a motor response of the corresponding muscle fiber. For example, as shown in FIG. 4C, the signal delivery device 100 can be positioned across/transverse to the anterior branches AB so that various combinations of the electrodes 104 can be activated to deliver a modulation signal to individual ones of the anterior branches AB. Although described with reference to the omohyoid muscle OHM, those of ordinary skill in the art will understand that the ansa cervicalis AC has motor points MP and anterior branches AB at locations where the ansa cervicalis AC innervates the other infrahyoid strap muscles. As a result, one or more signal delivery devices can be positioned to deliver modulation signals to one or more of the other motor points.

Referring to FIGS. 4A and 4B together, to implant the signal delivery device 100 in these positions and/or orientations, the signal delivery device 100 can be inserted into the patient in the anterior-to-posterior direction or the posterior-to-anterior direction. In either case, the first end portion 102a can lead the second end portion 102b or the second end portion 120b can lead the first end portion 102a.

Referring to FIG. 5A, the signal delivery device 100 is in an at least generally inferior-superior orientation and positioned at least proximate to the superior root SR and/or the common branch B3 of the ansa cervicalis AC. More specifically, the signal delivery device 100 is aligned with an interior-superior axis so that, e.g., the signal delivery device 100 is positioned over the common branch B3 when viewed normal to a sagittal plane of the patient and at least partially posteriorly of one or both of the sub-branches B3a, B3b innervating the sternothyroid muscle. In this position, the signal delivery device 100 can be configured to deliver the modulation signal to the superior root SR and/or common branch B3 based, at least in part, on which of the electrodes 104 are activated. In the inferior-superior orientation shown in FIG. 5A, the first end portion 102a is positioned superior to the second end portion 102b so that the orientation of the signal delivery device 100 includes a vector component that is aligned with the inferior-superior direction and/or parallel, or at least generally parallel, to the superior root SR.

Referring to FIG. 5B, the signal delivery device 100 is in a position and orientation that is at least generally similar to the position and orientation described previously with reference to FIG. 5A. However, in the inferior-superior orientation shown in FIG. 5B, the first end portion 102a is positioned inferior to the second end portion 102b so that the orientation of the signal delivery device 100 includes a vector component that is aligned with the inferior-superior direction and/or parallel, or at least generally parallel, to the superior root SR. In this position, the signal delivery device 100 can be configured to deliver the modulation signal to one or more of the superior root SR, the common branch B3, and/or one or both of the sub-branches B3a, B3b innervating the sternothyroid muscle STM and the sternohyoid muscle SHM, respectively, based at least in part on which of the electrodes 104 are activated.

Referring to FIGS. 5A and 5B together, to implant the signal delivery device 100 in this position and/or orientation, the signal delivery device 100 can be inserted into the patient in the inferior-to-superior direction or the superior-to-inferior direction, with the first end portion 102a leading the second end portion 102b or the second end portion 120b leading the first end portion 102a. Positioning the signal delivery device 100 in the inferior-superior orientation shown in FIGS. 5A and 5B is expected to have several advantages. For example, because at least a portion of the ansa cervicalis runs at least generally parallel to the patient's internal jugular vein IJV (FIG. 1B), a practitioner can avoid passing through or puncturing the internal jugular vein IJV while also using the internal jugular vein IJV as a navigation landmark to help position the signal delivery device 100 at least proximate to the ansa cervicalis AC. Additionally, or alternatively, because at least a portion of the ansa cervicalis AC extends in a generally inferior-superior direction, the signal delivery device 100 can be positioned in an inferior-superior orientation at least generally parallel to the ansa cervicalis without, or substantially without, changing an orientation of the signal delivery device 100 during delivery (such as described previously herein with reference to, e.g., FIGS. 2C and 2D).

FIGS. 6A-6D illustrate the signal delivery device 100 positioned at least proximate to the third branch B3 of the ansa cervicalis nerve AC in accordance with embodiments of the present technology. Generally, targeting the third branch B3 (and/or one or both of the sub-branches B3a, B3b thereof) is expected to reduce or prevent injury to the patient's internal jugular vein and/or the central carotid artery at least because of the distance between the third branch B3 and the internal jugular vein and central carotid artery. Additionally, or alternatively, targeting the third branch B3 is expected to inhibit, or even prevent, modulation of the vagus nerve at least because of the distance between the third branch B3 and the vagus nerve.

Figure 6A:
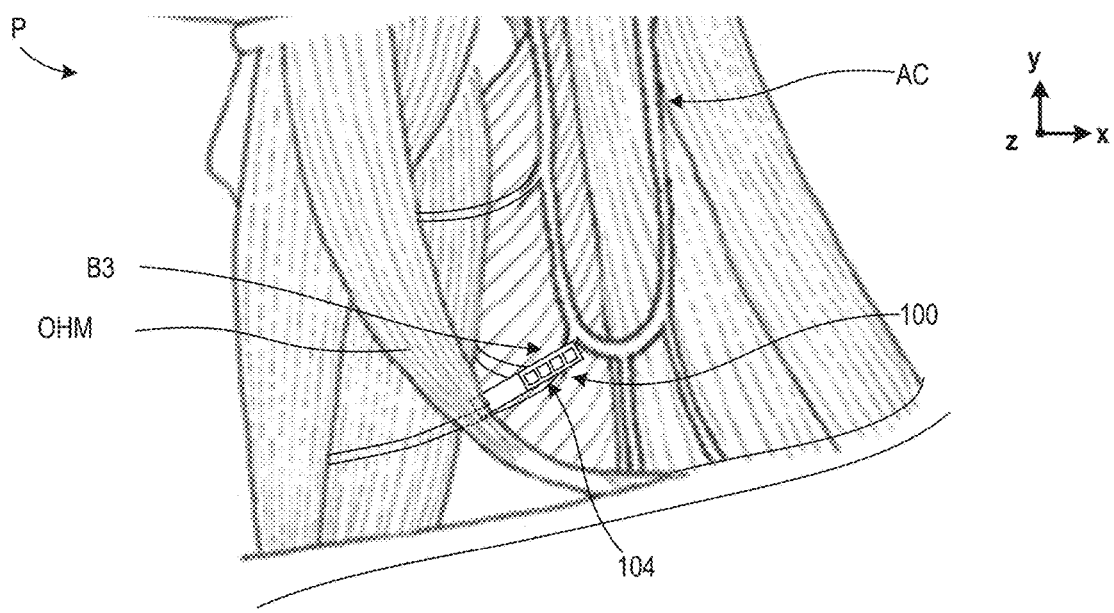
FIGS. 6A-6D are side sectional views of a portion of a patient's neck and lower jaw and depicting a signal delivery device positioned at least proximate to a third branch of an ansa cervicalis nerve of the patient in accordance with embodiments of the present technology.

Referring to FIG. 6A, the signal delivery device 100 is positioned at least generally parallel to the third branch B3, with at least a portion of the signal delivery device 100 positioned medially of the omohyoid muscle OHM. In this position, the electrodes 104 can deliver a modulation signal to the third branch B3 and produce a motor response in both the sternohyoid muscle SHM and the sternothyroid muscle STM.

Figure 6B:
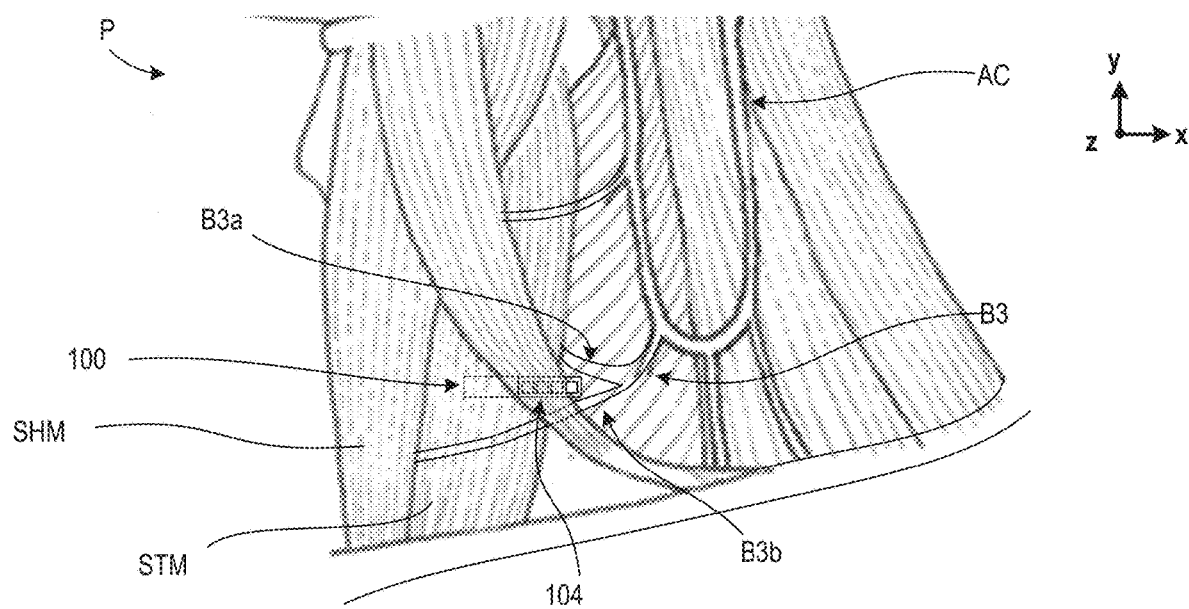

Referring to FIG. 6B, the signal delivery device 100 is positioned with the electrodes 104 at least partially between the first and second sub-branches B3a, B3b of the third branch B3. In this position, the signal delivery device 100 can selectively deliver a modulation signal to one or both of the first and second sub-branches B3a, B3b to selectively produce a motor response in one or both of the sternohyoid muscle SHM and the sternothyroid muscle STM. For example, individual ones of the electrodes 104 can be segmented or masked and configured to deliver the modulation signal upwardly/superiorly (e.g., toward the first sub-branch B3a) or downwardly/inferiorly (e.g., toward the second sub-branch B3b).

Figure 6C:
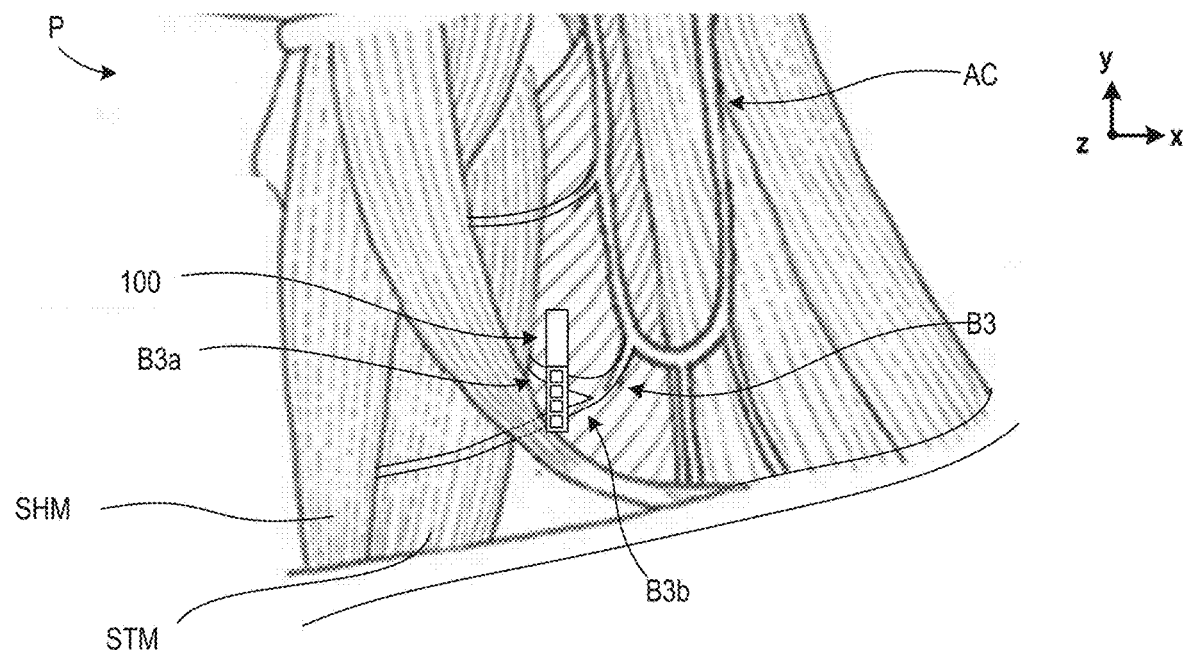

Referring to FIG. 6C, the signal delivery device 100 is positioned across (e.g., transverse to) the first and second sub-branches B3a, B3b. In this position, various combinations of the electrodes 104 can be activated to selectively deliver a modulation signal to one or both of the first and second sub-branches B3a, B3b which can selectively produce a motor response in one or both of the sternohyoid muscle SHM and the sternothyroid muscle STM. In the illustrated embodiment, for example, an electrical field can be generated between the lower two electrodes to deliver the modulation signal to the second sub-branch B3b, and/or an electrical field can be generated between the upper two electrodes to deliver the modulation signal to the first sub-branch B3a.

Figure 6D:
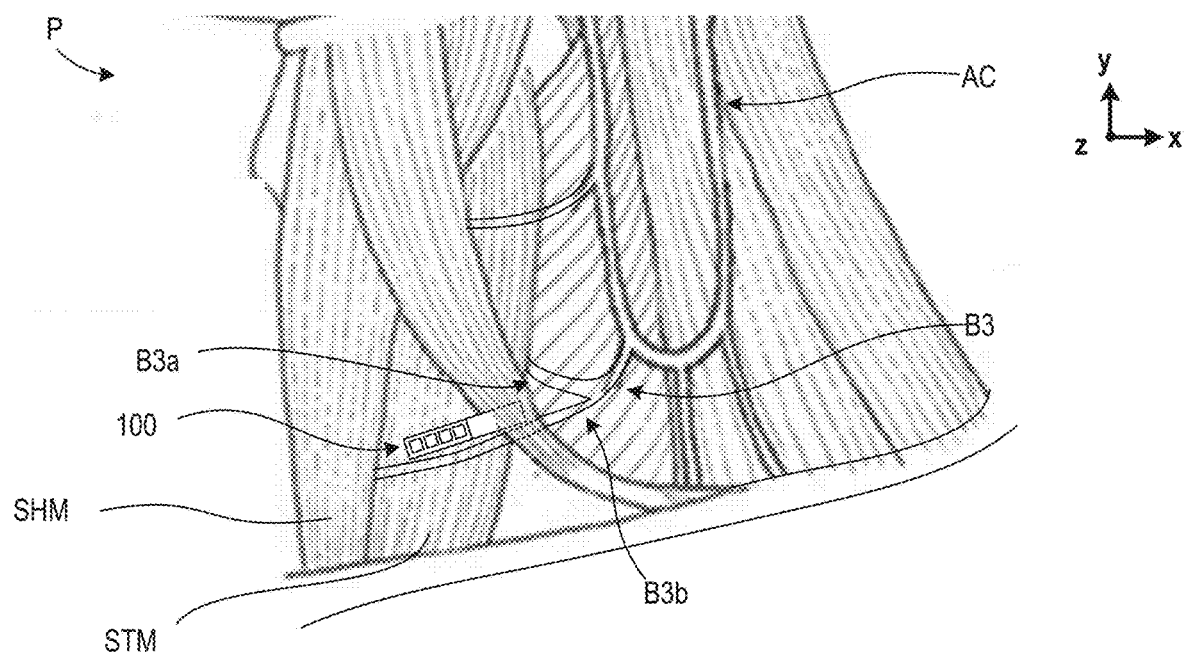

Referring to FIG. 6D, the signal delivery device 100 is positioned along the second sub-branch B3a. In this position, various combinations of the electrodes 104 can be activated to selectively deliver a modulation signal to the second sub-branches B3b, and/or the motor end plate at which the second sub-branch B3b innervates the sternohyoid muscle SHM (e.g., the inferior belly of the sternohyoid muscle SHMi, FIG. 1C), to selectively produce a motor response in the sternohyoid muscle SHM. In other embodiments, the signal delivery device 100 can be positioned to deliver a modulation signal to one or more locations along the length of the ansa cervicalis AC between the starting point of the third branch B3 and the point at which the second sub-branch B3a innervates the sternohyoid muscle SHM.

The positions and orientation of the signal delivery device 100 in FIGS. 2A-6D are generally described with reference to positioning the signal delivery device 100 at least proximate to the ansa cervicalis and/or one or more portions and/or branches thereof. In other embodiments, any of the insertion paths described herein (or at least one or more portions thereof) can be used to position the signal delivery device 100 at least proximate to one or more other target tissues, such as at least proximate to one or more of the patient's infrahyoid strap muscles. For example, additional embodiments associated with the patient's infrahyoid strap muscles are described below with reference to FIGS. 7A-9B.

Generally, modulation signals applied to a nerve, including the ansa cervicalis AC, have a characteristic neuromuscular activation threshold (e.g., a minimum amplitude) associated with causing an evoked motor response in tissue innervated by the nerve. Often, little to no motor response is evoked before the neuromuscular activation threshold is met. After meeting or exceeding the neuromuscular activation threshold, further changes to the modulation signals (e.g., further increases in delivered energy) often produce little or no additional motor response. This makes it difficult to induce the motor response gradually over time. One approach to address this problem is to apply the modulation signal directly to the muscle(s) associated with the motor response of interest. For example, applying modulation signals directly to one or more of the patient's infrahyoid strap muscles (e.g., the sternohyoid muscle SHM, the sternothyroid muscle STM, the omohyoid muscle OHM, and/or the thyrohyoid muscle THM) will activate the same muscles as when the modulation signals are applied to one or more portions/branches of the ansa cervicalis AC nerves. This additionally allows for a more gradual dose-response activation by recruiting individual muscle fibers compared to, e.g., activating the nerves/nerve branches innervating the infrahyoid strap muscles. For example, applying a first modulation signal having one or more first signal delivery parameters (e.g., amplitude, frequency, pulse width, etc.) to an infrahyoid strap muscle at a first point in time can cause a first motor response, and applying a second modulation signal having one or more second signal delivery parameters different than the one or more first signal delivery parameters to the infrahyoid strap muscle at a second point in time can cause a second motor response having a different (e.g., greater or lesser) degree, rate, range, and/or amount of motion than the first motor response. In some embodiments, the first signal delivery parameters can include a first amplitude, and the second signal delivery parameters can include a second amplitude greater than the first amplitude such that delivery of the second modulation signal is expected to produce a greater motor response than delivery of the first modulation signal. Thus, applying the modulation signals directly to the infrahyoid strap muscles is expected to improve the ability to modulate the caudal traction response by increasing control over the evoked patient motor response and/or rate of muscle contraction. The increased control over the evoked patient motor response can improve the ability to reduce and/or prevent airway obstructions and/or improve patient comfort and/or therapy compliance.

Additionally, because the infrahyoid strap muscles are larger than the nerves and/or nerve branches innervating them, the infrahyoid strap muscles are expected to be easier to identify (e.g., using the ultrasound probe 201 of FIG. 2A). Without being bound by theory, it is believed that the response of the infrahyoid strap muscles to directly delivered modulation signals is at least less sensitive to the position of the signal delivery device 100 within the infrahyoid strap muscles. Accordingly, the infrahyoid strap muscles can define a larger area (e.g., compared to a nerve) within which the signal delivery device 100 can be positioned for effective results, which is expected to reduce the time associated with identifying and/or implanting the signal delivery device 100. In these and other embodiments, implanting the signal delivery device 100 to deliver the modulation signal to the infrahyoid strap muscles is expected to increase the speed with which the signal delivery device 100 can be positioned at least proximate to the target location by reducing or eliminating the need to identify specific branching pattern of the patient's ansa cervicalis and then identify the portion(s) or branch(es) of the ansa cervicalis AC that constitute the target location.

Figure 7B:
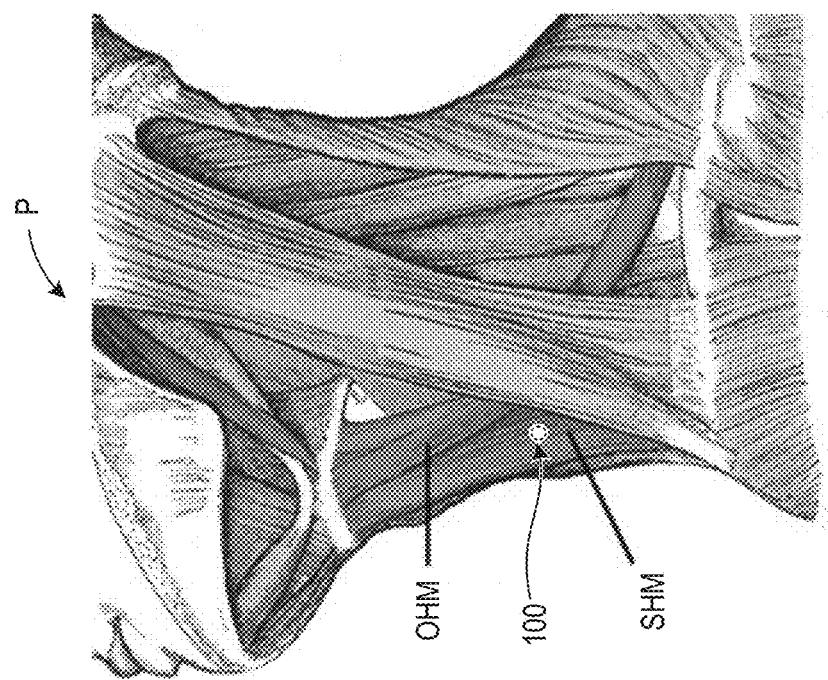
FIG. 7B is a side section view of a portion of the patient's neck and lower jaw, and the signal delivery device of FIG. 7B.
Figure 7A:
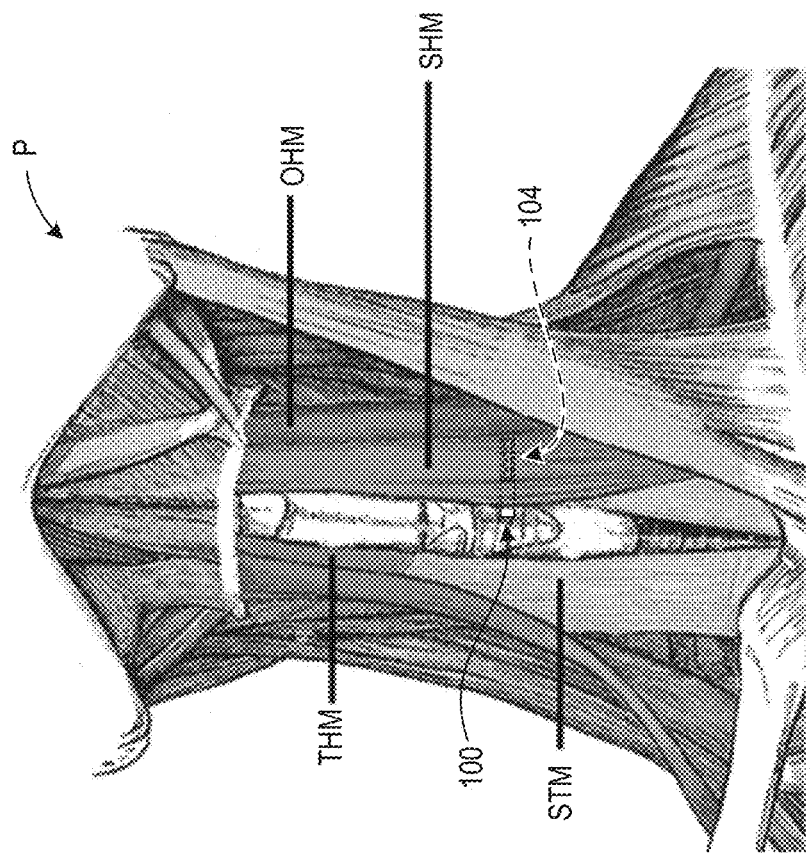
FIG. 7A is a front sectional view of a portion of a patient's neck and lower jaw and a signal delivery device positioned in accordance with embodiments of the present technology.

FIG. 7A is a front sectional view and FIG. 7B is a side sectional view of a portion of a patient's neck and lower jaw with the signal delivery device 100 implanted in a medial-lateral orientation between the sternohyoid muscle SHM and the sternothyroid muscle STM. In this position, the signal delivery device 100 can deliver the modulation signal to one or both of the sternohyoid muscle SHM and the sternothyroid muscle STM. For example, because the sternohyoid muscle SHM and the sternothyroid muscle STM are proximate to each other, the electrodes 104 can generate an electrical field that delivers the modulation signal to both the sternohyoid muscle SHM and the sternothyroid muscle STM at the same time. In other embodiments, the electrodes 104 can be segmented and individual segments carried by the signal delivery device 100 can deliver the modulation signal to one or both of the sternohyoid muscle SHM and the sternothyroid muscle STM.

The signal delivery device 100 can be implanted at this position and orientation using an insertion path at least generally similar or identical to the insertion path 210 described previously with reference to FIGS. 2A-3B. In other embodiments, the signal delivery device 100 can be positioned to deliver the modulation signal to the sternohyoid muscle SHM, the omohyoid muscle OHM, and/or the thyrohyoid muscle THM. In some embodiments, the signal delivery device 100 can have another suitable orientation, such as the inferior-superior orientation described previously with reference to FIGS. 5A and 5B.

Figure 8:
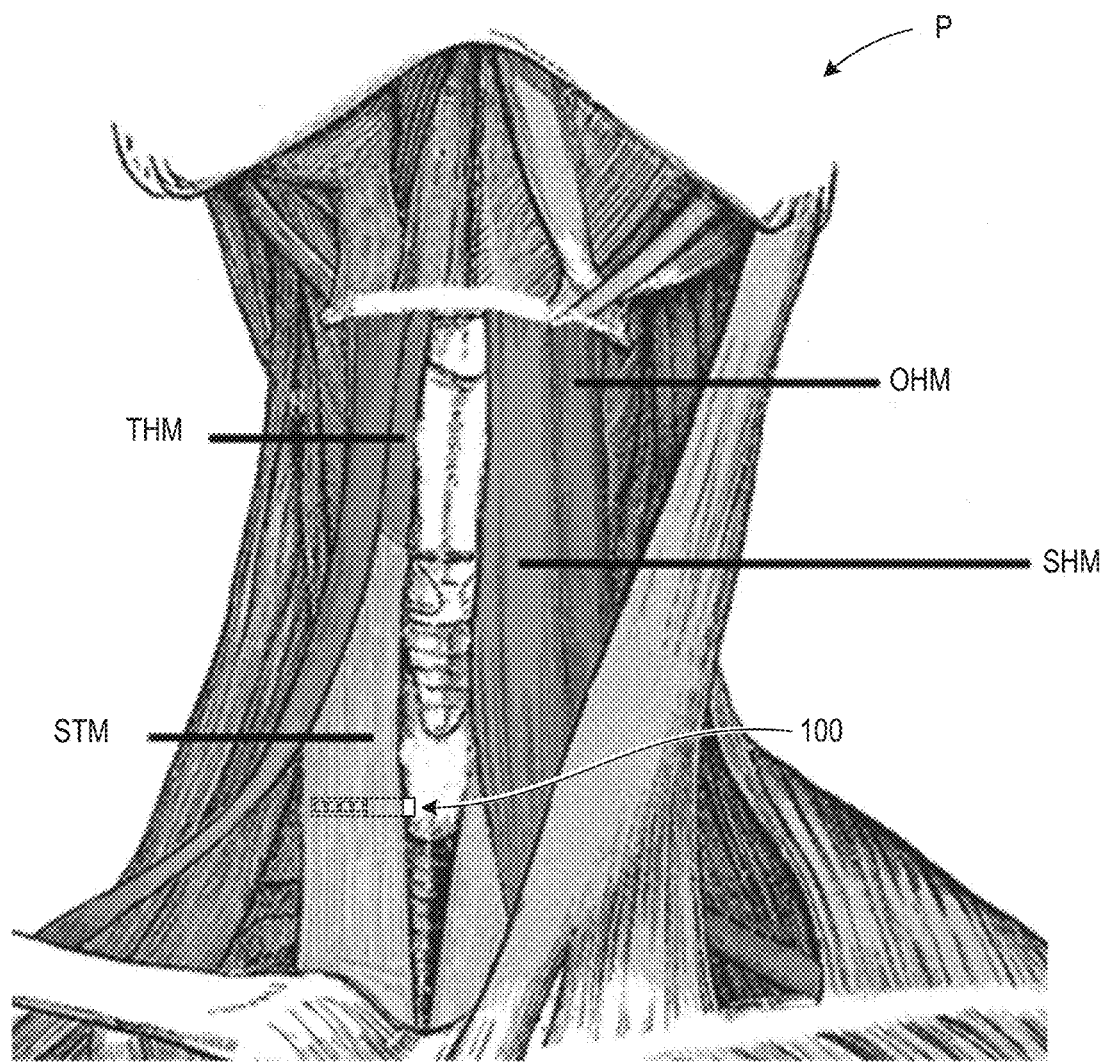
FIG. 8 is a front sectional view of a portion of a patient's neck and lower jaw and the signal delivery device positioned in accordance with embodiments of the present technology.

FIG. 8 is a front sectional view of a portion of a patient's neck and lower jaw with the signal delivery device 100 positioned at least partially within the patient's sternothyroid muscle STM. In this position, the signal delivery device 100 is expected to deliver a modulation signal to (e.g., only to) the sternothyroid muscle STM without or substantially without delivering the modulation signal to other tissues external to the sternothyroid muscle STM. In some embodiments, the signal delivery device 100 can be positioned fully within the sternothyroid muscle STM, and/or the signal delivery device can be positioned at least partially or fully within one or more of the sternohyoid muscle SHM, the omohyoid muscle OHM, the thyrohyoid muscle THM, and/or another muscle in the patient's neck and/or lower jaw.

Figure 9A:
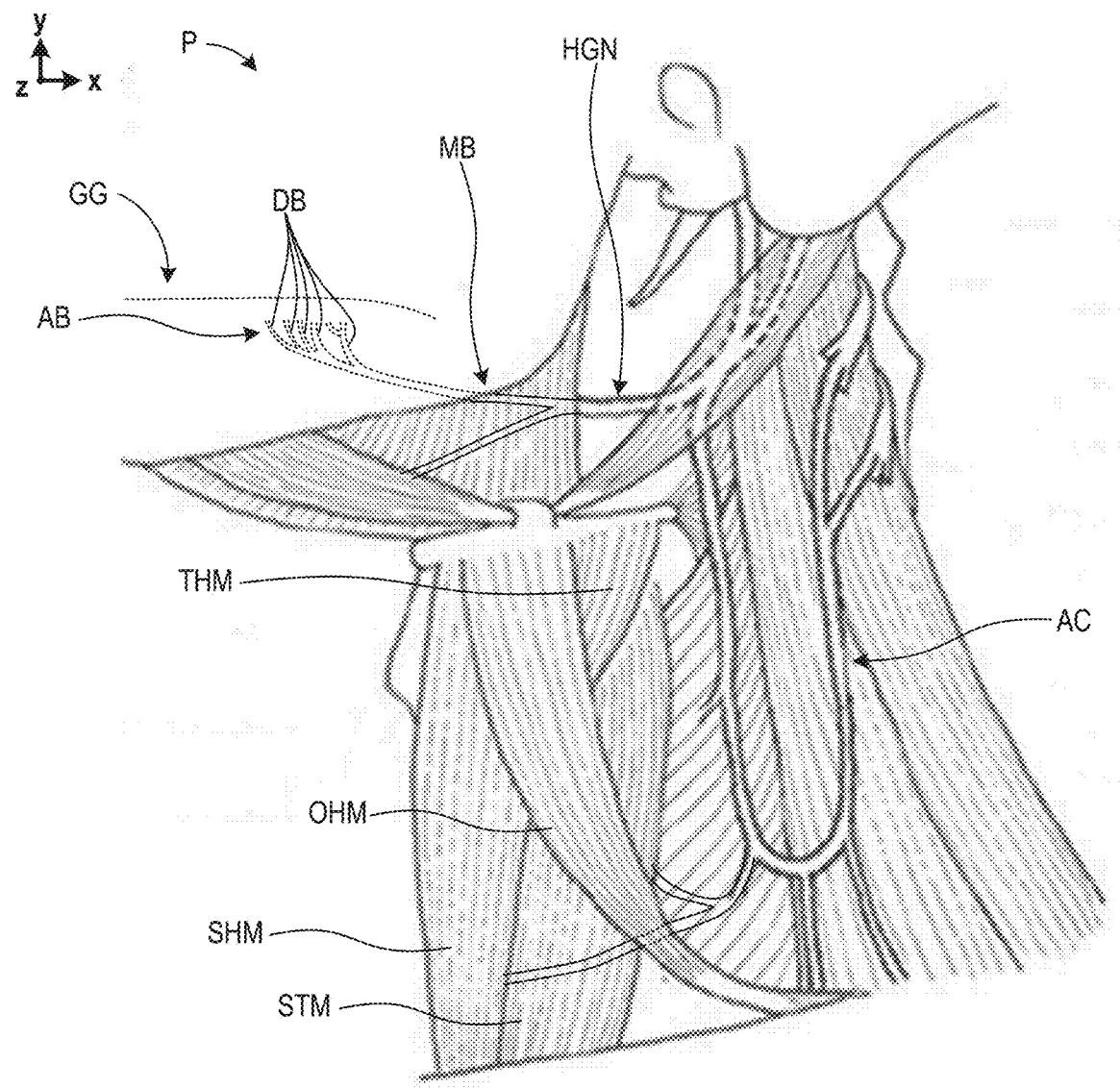
FIG. 9A is a side sectional view of a portion of the patient's neck and lower jaw anatomy.

FIG. 9A is a side section view of a portion of the patient's neck and lower jaw anatomy, including the ansa cervicalis AC, the omohyoid muscle OHM, the sternohyoid muscle SHM, the sternothyroid muscle STM, and the thyrohyoid muscle THM. FIG. 9A additionally illustrates the patient's hypoglossal nerve HGN, including the medial branch MB of the hypoglossal nerve HGN and the anterior branches AB of the hypoglossal nerve HGN. The anterior branches AB may include the distal arborizing portions of the HGN, such as the motor points, motor end plates, and/or neuromuscular junctions of the HGN as it inserts into the genioglossus GG. In some patients, one or more of the anterior branches AB may include a plurality of distal brachiated portions DB that innervate the patient's genioglossus muscle GG. By positioning and activating minimally invasive electrodes positioned proximate to the foregoing neural structures and/or associated musculature, embodiments of the present technology can control, reduce, and/or eliminate the effects of OSA. Additional details regarding the anterior branches AB can be found in U.S. application Ser. No. 18/393,537, filed Dec. 21, 2023, the entirety of which is hereby incorporated by reference herein.

Figure 9B:
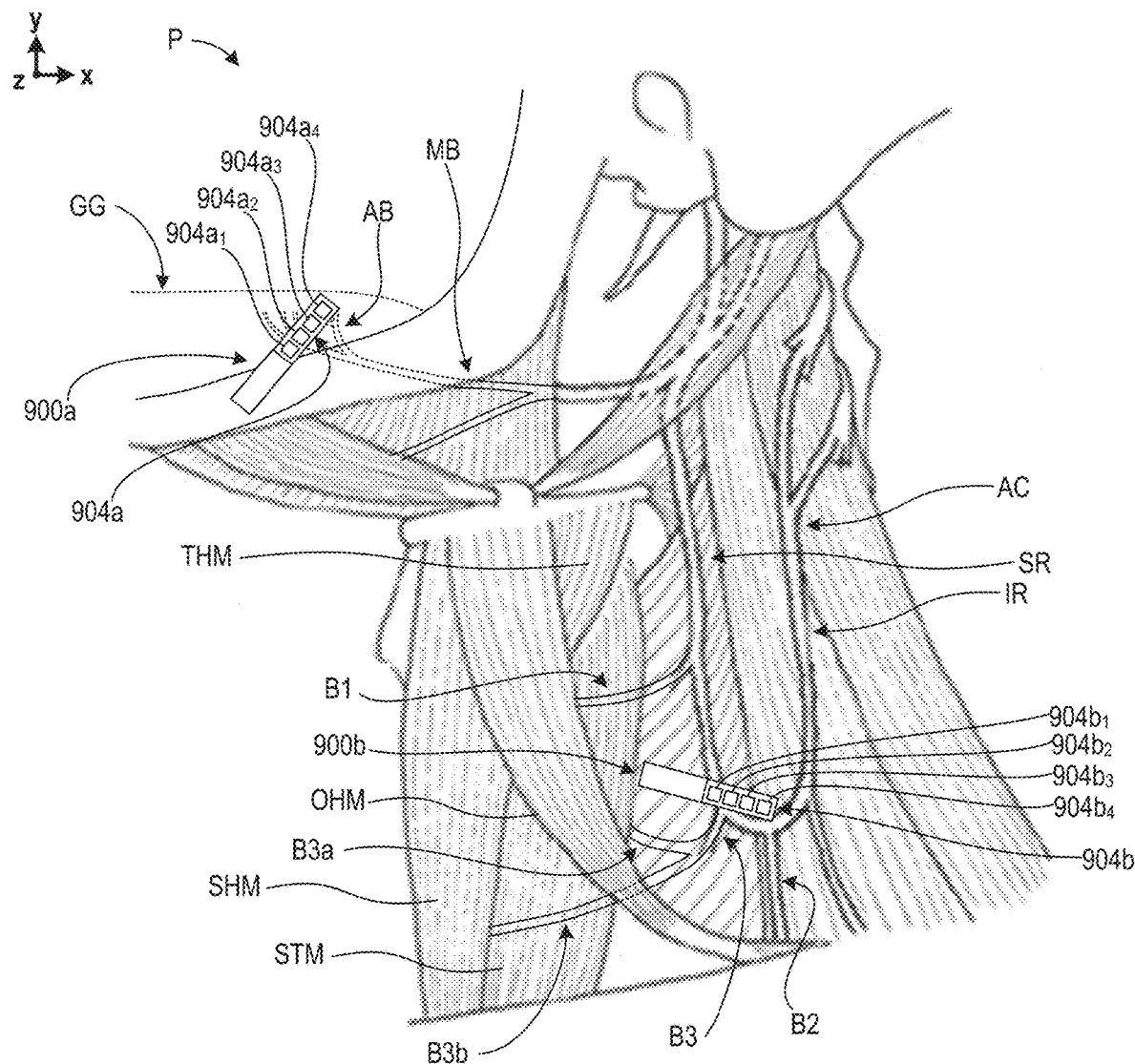
FIG. 9B is a side sectional view of a portion of the patient's neck and lower jaw anatomy including first and second signal delivery devices positioned in accordance with embodiments of the present technology.

FIG. 9B is a side section view of a portion of the patient's neck and lower jaw anatomy including first and second signal delivery devices 900a, 900b positioned in accordance with embodiments of the present technology. Each of the first and second signal delivery devices 900a, 900b can be at least generally similar or identical in structure and/or function to the signal delivery device 100 described previously with reference to FIG. 1D. The first and second signal delivery devices 900a, 900b can be implanted as part of a same procedure, or one of the first and second signal delivery devices 900a, 900b can be implanted sometime after the other of the first and second signal delivery devices 900a, 900b has been implanted.

The first signal delivery device 900a can be positioned to deliver modulation signals to a first target tissue and the second signal delivery device 900b can be positioned to deliver modulation signals to a second target tissue, different than the first target tissue. For example, in the illustrated embodiment, the first signal delivery device 900a is positioned to deliver one or more first modulation signal to the anterior branches AB of the patient's hypoglossal nerve HGN and the second signal delivery device 900b is positioned to deliver one or more second modulation signals to the third branch B3 of the ansa cervicalis AC. In some embodiments, the first signal delivery device 900a is implanted after the second signal delivery device 900b based at least in part on a determination that ansa cervicalis AC modulation alone is insufficient to address the patient's breathing obstructions. In other embodiments, the second signal delivery device 900b is implanted after the first signal delivery device 900a based at least in part on a determination that hypoglossal nerve HGN modulation alone is insufficient to address the patient's breathing obstructions.

The first signal delivery device 900a and/or the second signal delivery device 900b can have other suitable positions. For example, the first signal delivery device 900a can be positioned to deliver the first modulation signals to any one or more of: the medial branch MB of the hypoglossal nerve HGN, the genioglossus muscle GG directly, the inferior root IR of the ansa cervicalis AC, the superior root SR of the ansa cervicalis AC, one or more of the branches of the ansa cervicalis AC, one or more of the motor points of the ansa cervicalis AC, the omohyoid muscle OHM, the sternohyoid muscle SHM, the sternothyroid muscle STM, the thyrohyoid muscle THM, or another target location described herein to address the patient's OSA. Additionally, or alternatively, the second signal delivery device 900b can be positioned to deliver the second electricals signals to any one or more of: the medial branch MB of the hypoglossal nerve HGN, one or more of the anterior branches AB of the hypoglossal nerve HGN, the genioglossus muscle GG directly, the inferior root IR of the ansa cervicalis AC, the superior root SR of the ansa cervicalis AC, one or more of the branches of the ansa cervicalis AC, one or more of the motor points of the ansa cervicalis AC, the omohyoid muscle OHM, the sternohyoid muscle SHM, the sternothyroid muscle STM, and/or the thyrohyoid muscle THM, or another target location described herein to address the patient's OSA. In these and/or other embodiments, the first and second signal delivery devices 900a, 900b can be positioned to bilaterally stimulate respective tissues on the left and right side of the patient, e.g., the left hypoglossal nerve and the right ansa cervicalis nerve, the left thyrohyoid muscle and the right genioglossus muscle, etc.

The first and second signal delivery devices 900a, 900b can be configured to deliver modulation signals having the same or one or more different signal delivery parameters (e.g. amplitude, frequency, pulse width) to, e.g., optimize the patient's airflow response or efficacy for each respective target location. For example, individual ones of the signal delivery parameters can be determined based, at least in part, on the patient's measured airway flow response or another physiologic input from an external wearable or another device configured to detect the patients airway flow response. Additionally, or alternatively, one or more signal delivery parameters of the modulation signals delivered by the first and second signal delivery devices 900a, 900b can vary based, at least in part, on the respective locations and/or target tissues of the first and second signal delivery devices 900a, 900b. For example, with the first and second single delivery devices 900a, 900b positioned as shown in FIG. 9B, the first and second single delivery devices 900a, 900b can be programmed to deliver respective modulation signals with different pulse widths, e.g., the first signal delivery device 900a with a pulse width of about 100 μs and the second signal delivery device 900b a pulse width of about 50 μs.

In some embodiments, one or more of the signal delivery parameters of the modulation signal delivery by the first signal delivery device 900a and/or the second signal delivery device 900b can be adjusted or modulated during delivery in, e.g., a closed loop or an open loop manner. For example, the adjustments/modulations to the signal delivery parameters can compensate for movement of one or both of the signal delivery devices 900a, 900b relative to their respective target locations after implantation, which can be caused by movement of the patient and/or one or more changes in a patient's body position. Additionally, the adjustments/modulations to the signal delivery parameters can compensate for one or more changes in the patient's sleep stage, data associated with an efficacy of the modulation therapy (e.g., air flow, respiratory effort), etc.

In some embodiments, the first and second signal delivery devices 900a, 900b can be activated independently, such that one of the first and second signal delivery devices 900a, 900b can be active while the other of the first and second signal delivery devices 900a, 900b is inactive. Each of the first and second signal delivery devices can alternate between active/on and inactive/off states independently for selected periods, such as very short durations (e.g., 100 msec) or longer durations (e.g., 10 seconds). For example, in some embodiments, an ON-OFF modulation pattern can be programmed to regularly alternate between the first signal delivery device 900a and the second signal delivery device 900b. For example, the first signal delivery device 900a can be ON (e.g., receiving power and/or delivering modulation signals) for a first time period (e.g., at least 1 second, 2 seconds, 3 seconds, 4 seconds, 5 seconds, etc.), followed by the second signal delivery device 900b being ON for a second time period (e.g., at least 1 second, 2 seconds, 3 seconds, 4 seconds, 5 seconds, etc.). In some embodiments, the first time period and/or the second time period can be randomly selected. In some embodiments, the first signal delivery device 900a can be OFF (e.g., not receiving power and/or not delivering modulation signals) when the second signal delivery device 900b is ON and/or vice versa, and/or delivery of the modulation signals can be concurrent for a portion of the modulation pattern. In other embodiments, both the first and second signal delivery devices 900a, 900b can be ON and OFF at the same, or at least generally the same, times. In further embodiments, the times during which a given signal delivery device 900a, 900b is ON or OFF can be randomized. In some embodiments, after at least one of first signal delivery device 900a and the second signal delivery device 900b have completed an ON interval, the first signal delivery device 900a and/or the second signal delivery device 900b can remain OFF for an OFF interval. The OFF interval can be up to 1 minute, 2 minutes, 3 minutes, 4 minutes, 5 minutes, 10 minutes, etc. The OFF interval can also vary over time, can be randomly selected, and/or include one or more other suitable durations of time.

In some embodiments, individual electrodes carried by the first and second signal delivery devices 900a, 900b can be activated or deactivated to direct delivery of the modulation signal toward the respective target location and/or to adjust the electrical field generated to deliver the modulation signal (e.g., narrow or widen the electrical field). In the illustrated embodiment, for example, the first and second signal delivery devices 900a, 900b include quadripolar electrodes arrays 904a, 904b, each having four electrodes $904a_{1-4}$, $904b_{1-4}$. Using the second and third electrodes $904a_{2,3}$, $904b_{2,3}$ can create a field that is narrower than, e.g., using the first and fourth electrodes $904a_{1,4}$, $904b_{1,4}$. In some embodiments, the second and third electrodes $904a_{2,3}$ of the first signal delivery device 900a can be activated and the first and fourth electrodes $904b_{1,4}$ of the second signal delivery device 900b can be activated so that the first signal delivery device 900a generates a relatively narrow field and the second signal delivery device 900b generates a relatively wide field. In other embodiments, any other combinations of the electrodes $904a_{1-4}$, $904b_{1-4}$ can be activated.

In some embodiments, a cyclic modulation pattern can be programmed to regularly alternate one or more parameters of the signals delivered by the first and second signal delivery devices 900a, 900b. The amplitude, pulse width, and/or frequency can be programmed to be changed regularly at programmed time intervals, in response to sensed data, randomly, irregularly, etc. For example, the first signal delivery device 900a could be set to 1.0 mA for 1 second, then 2.0 mA for 1 second, and then 1.0 mA for 1 second for a duration of 3 seconds of modulation. The second signal delivery device 900b could be set to 0.5 mA for 1 second, then 1.0 mA for 1 second, and then 0.5 mA for 1 second for a duration of 3 seconds of modulation. In some embodiments, the amplitudes of these patterns could be inverted relative to one other. The first and second signal delivery devices 900a, 900b can deliver their respective modulation signals at the same or different times, and/or the modulation signals can be delivered concurrently for a portion of the modulation pattern.

In some embodiments, an if-then modulation pattern can be programmed to respond to one or more specific physiologic measurements (e.g., air flow) detected or determined by, e.g., one or more sensors of the signal delivery device, one or more sensors implanted within the patient, and/or a wearable or other external sensing device. For example, one of the first and second signal delivery devices 900a, 900b can be turned ON by the wearable. If the patient's physiologic response is insufficient, as determined based at least in part on the one or more physiological measurements, the other of the first and second signal delivery devices 900a, 900b can then be turned ON so that both the first and second signal delivery devices 900a, 900b are operating simultaneously. Additionally, or alternatively, one or more parameters of the respective signals delivered by the first and second signal delivery devices 900a, 900b, can be adjusted (e.g., as described herein) in response one or more of the physiological measurements.

In some embodiments, the first and second signal delivery devices 900a, 900b can be programmed with phase manipulation patterns. For example, the amplitude of the modulation signal delivered by the first signal delivery device 900a can ramp up and down during a modulation interval in a sine wave shape. The modulation signal delivered by the second signal delivery device 900b can have a similar amplitude shape, and can have a phasing pattern in phase or 180 degrees out of phase with the first signal delivery device's modulation signal. In at least some embodiments, the first and/or second signal delivery devices 900a, 900b can be programmed to create a phase inversion via delivery of their respective modulation signals. In some embodiments, the modulation signal can be a square wave and can be ramped in a stepwise fashion, e.g., from a first pulse to a second pulse.

4. Representative Experimental Data

Figure 10A:
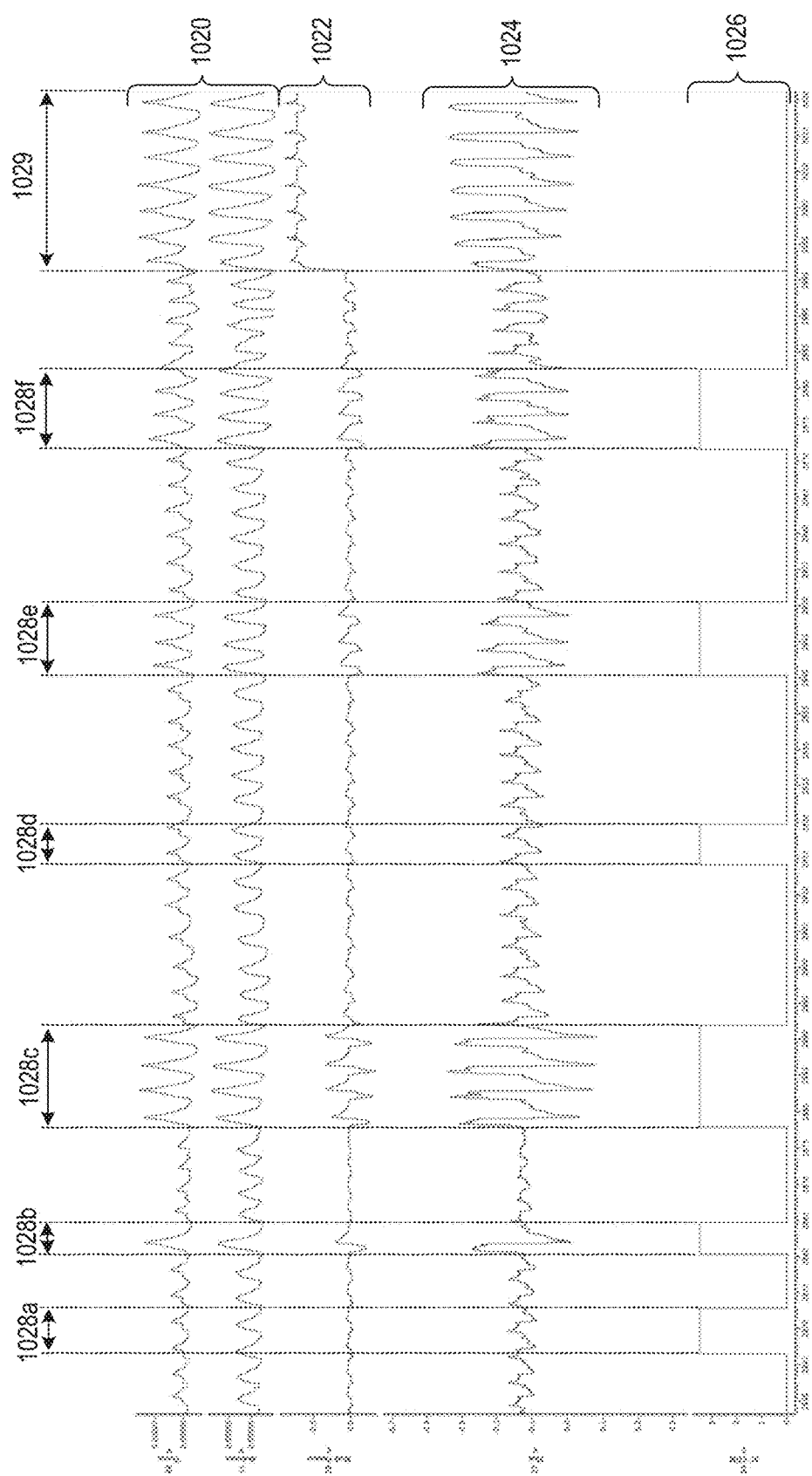
FIG. 10A illustrates plots of patient data obtained by directing a modulation signal to a patient's ansa cervicalis nerve in accordance with embodiments of the present technology.

FIG. 10A illustrates plots of patient data obtained by directing a modulation signal to a patient's ansa cervicalis nerve in accordance with several embodiments of the present technology. Specifically, FIG. 10A includes plots of respiratory impedance plethysmography ("RIP") 1020, CPAP mask pressure 1022, airflow 1024, and ansa cervicalis modulation 1026 signals during multiple signal delivery periods 1028 (individually identified as a first signal delivery period 1028a, a second signal delivery period 1028b, and a third signal delivery period 1028c) and a post-signal delivery period 1029.

To obtain these data, a patient was instrumented with an electroencephalogram, an electrooculogram, a submental chin electromyogram, an epiglottic pressure sensor, and a sealed nasal mask and pneumotach to quantify airflow. Following propofol sedation, the patient's ansa cervicalis nerve were identified using ultrasound to guide placement of a percutaneous electrode array as described previously herein in a position and/or orientation that is at least generally similar to the embodiment shown in FIG. 6D. The electrode array used during this test included four electrical contacts arranged in series (referred to hereinafter as electrode #1, electrode #2, electrode #3, and electrode #4). An endoscope was inserted via the patient's nose to visualize changes to the patient's airway size and shape during periods in which modulation signals were delivered to the distal branches via the electrode array. A modified CPAP device was used to deliver therapeutic CPAP and transient pressure reductions to induce airflow limitation/closure in a manner that simulates breathing obstructions experienced by patients with sleep disordered breathing.

During the post-signal delivery period 1029, the pressure within the patient's airway was returned to normal levels, as shown by the changes to the RIP and CPAP mask pressure plots 1020, 1022, and the electrode array was inactive (i.e., no modulation signals were delivered to the patient's ansa cervicalis). Outside of the signal delivery periods 1028, reductions in the RIP plot 1020, the CPAP mask pressure plot 1022, and the airflow plot 1024 relative to the post-signal delivery period 1029 illustrate that the patient's breathing was obstructed.

During each of the signal delivery periods 1028, a modulation signal was directed to the ansa cervicalis nerve from an electrode array positioned in accordance with embodiments of the present technology. Specifically, during the first signal delivery period 1028a, a 1 mA bipolar modulation signal was delivered to the ansa cervicalis with electrode #1 acting as the cathode and electrode #3 acting as the anode. The 1 mA modulation signal did not substantially increase or otherwise improve the patient's airflow, as shown by the patient's airflow plot 1024 before, during, and after the first signal delivery period 1028a. This is further supported by the RIP plot 1020 and the CPAP mask pressure plot 1022, which remained substantially unchanged during the first signal delivery period 1028a.

During the second signal delivery period 1028b, a 1.5 mA bipolar modulation signal was delivered to the ansa cervicalis with electrode #1 acting as the cathode and electrode #3 acting as the anode. The 1.5 mA modulation signal increased the patient's airflow, as shown by the corresponding change in the airflow plot 1024 during the second signal delivery period 1028b, but this change did not fully-restore the patient's airflow. Put differently, the 1.5 mA signal produced a beneficial yet sub-maximal flow response. This change to the patient's airflow is further demonstrated by the corresponding changes to the RIP and CPAP mask pressure plots 1020, 1022 during the second signal delivery period 1028b.

During the third signal delivery period 1028c, a 2 mA modulation signal was delivered to the ansa cervicalis with electrode #1 acting as the cathode and electrode #3 acting as the anode. The 2 mA modulation signal increased the patient's airflow, as shown by the corresponding change in the airflow plot 1024 during the third signal delivery period 1028c. Compared to the 1.5 mA modulation signal delivered during the second signal delivery period 1028b, the 2 mA modulation signal produced a greater increase to the patient's airflow, fully restoring the patient's airflow to normal or otherwise pre-obstructed levels. This change to the patient's airflow is further demonstrated by the corresponding changes to the RIP and CPAP mask pressure plots 1020, 1022 during the third signal delivery period 1028c.

During the fourth signal delivery 1028d, a 0.5 mA modulation signal was delivered to the ansa cervicalis with electrode #2 acting as the cathode and electrode #4 acting as the anode. The 0.5 mA modulation signal did not substantially increase or otherwise improve the patient's airflow, as shown by the patient's airflow plot 1024 before, during, and after the fourth signal delivery period 1028d. This is further supported by the RIP plot 1020 and the CPAP mask pressure plot 1022, which remained substantially unchanged during the fourth signal delivery period 1028d.

During the fifth signal delivery period 1028e, a 1.5 mA bipolar modulation signal was delivered to the ansa cervicalis with electrode #2 acting as the cathode and electrode #4 acting as the anode. The 1.5 mA modulation signal increased the patient's airflow, as shown by the corresponding change in the airflow plot 1024 during the fifth signal delivery period 1028c, but this change did not fully-restore the patient's airflow. Put differently, the 1.5 mA signal produced a beneficial yet sub-maximal flow response. This change to the patient's airflow is further demonstrated by the corresponding changes to the RIP and CPAP mask pressure plots 1020, 1022 during the fifth signal delivery period 1028e. However, the airflow increase during the fifth signal delivery period 1028c was approximately equal to the airflow increase elicited during the second signal delivery period 1028b in response another 1.5 mA modulation signal.

During the sixth signal delivery period 1028f, a 2 mA bipolar modulation signal was delivered to the ansa cervicalis with electrode #2 acting as the cathode and electrode #4 acting as the anode. Whereas the 2 mA modulation signal delivered via electrodes #1 and #3 during the third signal delivery period 1028c fully restored the patient's airflow, the 2 mA modulation signal delivered via electrodes #2 and #4 during the sixth signal delivery period 1028f increased the patient's airflow to a level below full airflow restoration (see the corresponding change in the airflow plot 1024 during the sixth signal delivery period 1028f). Put differently, the 2 mA signal delivered via electrodes #2 and #4 during the sixth signal delivery period 1028f produced a beneficial yet sub-maximal flow response. This change to the patient's airflow is further demonstrated by the corresponding changes to the RIP and CPAP mask pressure plots 1020, 1022 during the sixth signal delivery period 1028f. Accordingly, given a particular position of the electrode array relative to the ansa cervicalis, selecting one or more combinations of bi-polar electrode arrangements may produce superior results (e.g., in this particular position of the electrode array using electrode #1 as the cathode and electrode #3 as the anode may be a better lead configuration than using electrode #2 as the cathode and electrode #4 as the anode).

During the post-signal delivery period 1029, the pressure within the patient's airway was returned to normal levels, as shown by the changes to the RIP and CPAP mask pressure plots 1020, 1022, and the electrode array was inactive (i.e., no modulation signals were delivered to the patient's ansa cervicalis). Accordingly, the airflow plot 1024 during the post-signal delivery period 1029 represents the patient's normal breathing behavior. Comparing the airflow plot 1024 during the third signal delivery period 1028c and the post-signal delivery period 1029 further illustrates that the 2 mA modulation signal delivered during the third signal delivery period 1028c fully-restored the patient's airflow.

These data demonstrate that delivering modulation signals to the ansa cervicalis nerve from an electrode array positioned in accordance with embodiments of the present technology caused a patient motor response (e.g., caudal traction) to restore airflow. Additionally, although the patient was sedated during this test, the inventors observed data indicating that, if modulation signals such as those delivered during the signal deliver periods 1028 were delivered to the patient while the patient was asleep, it is unlikely that the patient would have been roused from sleep. Several of the amplitudes used during the signal delivery periods 1028 were lower than amplitudes (e.g., about 2 mA to about 4 mA) used to stimulate the hypoglossal nerve and produce corresponding increases to patient airflow, such as described with reference to at least FIGS. 12-15 of U.S. application Ser. No. 18/393,537, the entirety of which is incorporated by reference herein. Accordingly, without being bound by theory, it is believed that the relatively lower amplitude of the signals delivered to the ansa cervicalis are expected to reduce, or prevent entirely, patient arousal rates while also addressing breathing obstructions by at least increasing, or even fully restoring, the patient's airflow. In some embodiments, the lower amplitudes associated with ansa cervicalis modulation are expected to reduce the amount of power transmitted to one or more implanted devices positioned to deliver modulation signals to the ansa cervicalis nerve compared to the power transmission requirements for one or more implanted devices positioned to deliver modulation signals to the hypoglossal nerve. In these and/or other embodiments, however, the use of hypoglossal nerve modulation as a secondary modulation location and/or in addition to the ansa cervicalis nerve is expected to improve (e.g., further improve) the patient's airflow.

FIG. 10B is a table including data obtained by positioning and activating a signal delivery device in accordance with embodiments of the present technology. Signal delivery devices were positioned to stimulate the ansa cervicalis nerves of Subjects 1, 4, and 5 using a medial-to-lateral approach, as described previously herein with reference to FIG. 2A. Signal delivery devices were positioned to stimulate the ansa cervicalis nerves of Subjects 2, 3, 5, 6, and 7 using a lateral-to-medial approach, as described previously herein with reference to FIG. 2A. As shown by the VOTE ("Velum Oropharynx Tongue Epiglottis") scores in this table, before and after modulation, subjects 1-7 had documented tissue collapse at varying locations (e.g., velum/retropalatal, oropharynx, tongue base/retrolingual, and/or epiglottis/retroepiglottic) and of various types (e.g., anteroposterior (A/P), concentric, and/or lateralateral (L/L)). Despite the differences in how these subjects' breathing obstructions presented physiologically, delivering modulation signals of various amplitudes (e.g., in an amplitude range between about 0.5 mA and about 5 mA) produced an at least 80% increase in peak airflow amplitude, and most of the subjects experienced more than a 100% increase in peak airflow amplitude. Additionally, Subjects 2-4 experienced collapse of the tongue base, which is traditionally addressed by stimulating the hypoglossal nerve. However, modulating the ansa cervicalis nerve of Subjects 2-4 in accordance with embodiments of the present technology significantly increased these Subject's airflow. It is believed that modulating the ansa cervicalis nerve in the matter performed with Subjects 2-4 surprisingly caused the base of their tongue to move inferiorly and thereby reduce the tongue base collapse while also stiffening the airway via caudal traction. This resulted in surprisingly large increases in airflow for Subjects 2-4. This was even more surprising because, as described previously herein with reference to FIG. 1A, the inventors observed that lowering the hyoid bone by modulating the ansa cervicalis nerve to produce caudal traction produced a corresponding movement of the base of the tongue that, in at least some instances, can reduce or even eliminate tongue base collapse.

Figure 10C:
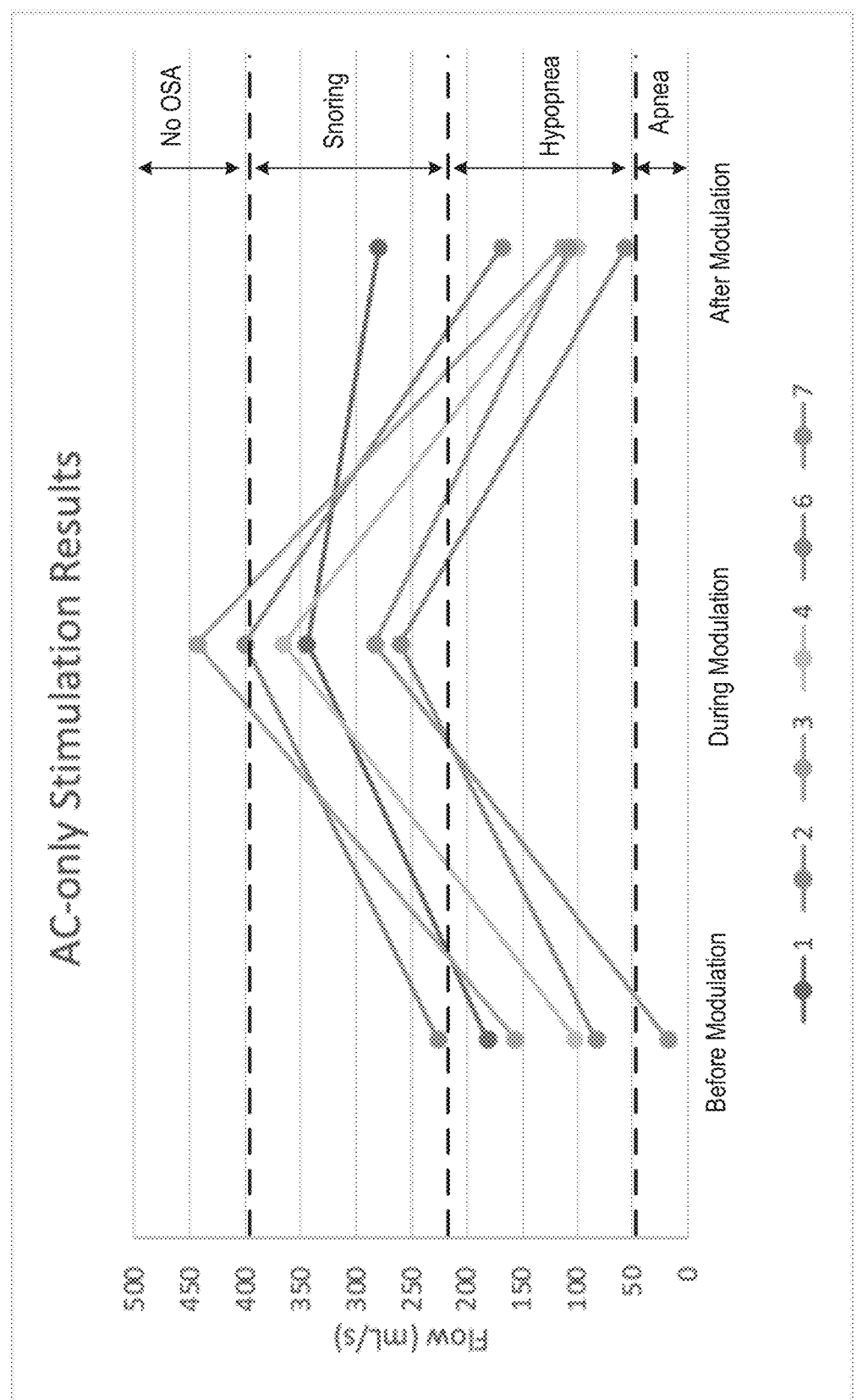
FIG. 10C is a plot showing airflow restoration for the patients listed in the table of FIG. 10B.

FIG. 10C is a plot showing airflow restoration for all of the subjects listed in the table of FIG. 10B except for subject 5. As shown, the various modulation signals described above significantly improved the subjects' airflow. Most subjects exhibited airflow at levels associated with hypopnea before and after modulation, but during modulation their airflow levels increased to a range associated with snoring. Subjects 2 and 3 experienced increases in airflow levels to those associated with no breathing obstructions whatsoever. Subject 7's airflow increased from a level associated with complete apnea (e.g., little to no airflow) before modulation to a level associated with snoring during modulation. The inventors did not expect that delivering modulation to the ansa cervicalis alone would produce airflow increases of this magnitude.

The data in FIGS. 10A-10C demonstrate that delivering modulation signals to the ansa cervicalis nerve from an electrode array positioned in accordance with embodiments of the present technology caused a patient motor response (e.g., caudal traction) to restore airflow. Additionally, no signs of patient arousal were observed during the signal delivery periods 1028. Several of the amplitudes used during the signal delivery periods 1028 were lower than amplitudes (e.g., about 2 mA to about 4 mA) used to stimulate the hypoglossal nerve and produce corresponding increases to patient airflow, such as described with reference to at least FIGS. 12-15 of U.S. application Ser. No. 18/393,537, the entirety of which is incorporated by reference herein. Accordingly, without being bound by theory, it is believed that the relatively lower amplitude of the signals delivered to the ansa cervicalis are expected to reduce, or prevent entirely, patient arousal rates while also addressing breathing obstructions by at least increasing, or even fully restoring, the patient's airflow. In some embodiments, the lower amplitudes associated with ansa cervicalis modulation are expected to reduce the amount of power transmitted to one or more implanted devices positioned to deliver modulation signals to the ansa cervicalis nerve compared to the power transmission requirements for one or more implanted devices positioned to deliver modulation signals to the hypoglossal nerve. In these and/or other embodiments, however, the use of hypoglossal nerve modulation as a modulation location secondary and/or in addition to the ansa cervicalis nerve is expected to improve (e.g., further improve) the patient's airflow.

Although certain modulation amplitudes are described above with reference to FIGS. 10A and 10B, in other embodiments additional and/or other modulation amplitudes can be delivered to the ansa cervicalis, the hypoglossal nerve, and/or one or more other target tissued described herein. In some embodiments, the modulation amplitudes can be based at least in part on one or more modulation thresholds associated with the corresponding target tissue. Generally, for a given nerve, a modulation threshold is the level of modulation (e.g., amplitude) at which further increases to the level of modulation do not produce an increase in the patient's airflow response. This is because modulation at the modulation threshold produces a full muscle response (e.g., a full contraction and/or tetanic response of one or more muscles innervated by the ansa cervicalis) and, therefore, modulation at levels higher than the modulation threshold cannot produce a further muscle response beyond the already full muscle response.

As shown in FIG. 10A, increasing the amplitude of the modulation signal from 1.5 mA during the second signal delivery period 1028b to 2 mA during the second signal delivery period 1028c produced a corresponding increase in the patient's airflow. Accordingly, because increasing the amplitude beyond 1.5 mA produced an increase in the patient's airflow, the ansa cervicalis is expected to have a modulation threshold greater than 1.5 mA. Put differently, a 1.5 mA modulation signal is a sub-threshold signal less than the modulation threshold. The modulation threshold for this patient and/or other patients may vary based, at least in part, on the proximity of the electrode array to the ansa cervicalis nerve and/or the location of the electrode array along the ansa cervicale's nerve. Delivering one or more modulation signals to the ansa cervicalis at amplitudes in the sub-threshold range is not expected to produce a full muscle response (e.g., a full contraction and/or tetanic response of one or more muscles innervated by the ansa cervicalis). Instead, delivering modulation signals to the ansa cervicalis at sub-threshold amplitudes is expected to stiffen or tighten one or more of the muscles innervated by the ansa cervicalis nerve and improve airflow, which makes these tissues less likely to obstruct the patient's breathing and/or at least less likely to further obstruct the patient's breathing without inducing a full muscular contraction or tetanic response.

In some aspects of the present technology, sub-threshold amplitudes can restore one or more tissues of the patient's airway to a more natural condition (e.g., a muscular tone (stiffness) that more closely resembles health patient tissue) and/or allows the patient to breath in a more natural fashion compared to threshold or suprathreshold modulation amplitudes. For example, as noted above, threshold or suprathreshold modulation amplitudes are expected to fully-contract the muscles innervated by the ansa cervicalis nerve. The resulting sensation experience by the patient is often uncomfortable and much different than natural breathing, and it may lead to arousal. Moreover, full muscular contraction may not be necessary to adequately improve the patient's airflow or otherwise adequately address their breathing obstruction. The one or more muscles that contract in response to modulation can also be selected to allow the patient to breath in a more natural fashion during modulation. For example, many patients are accustomed to the experience of their sternohyoid muscles SHM and/or sternothyroid muscles STM being maximally contracted during inspiratory periods (e.g., during a yawn). However, many patients are not accustomed to the experience of their genioglossus muscle GG being maximally contract, as this does not regularly occur during inspiratory periods. Accordingly, it is expected that delivering modulation signals that cause the sternohyoid muscles SHM and/or sternothyroid muscles STM to contract will be less likely to rouse the patient from sleep, and/or otherwise cause the patient discomfort, than modulation signals that cause the genioglossus muscle to contract.

Stiffening tissues defining the patient's airway, without producing a full muscular contraction, can improve the patient's breathing without, or substantially without, causing discomfort (e.g., arousal). For example, as shown in FIG. 10A, the sub-threshold 1.5 mA modulation signal delivered during the second signal delivery period 1028b improved the patient's airflow. Although this 1.5 mA modulation signal did not fully-restore the patient's airflow, there are advantages to delivering modulation signals at sub-threshold amplitudes. For example, at least some sub-threshold amplitudes are below the patient's perception threshold and/or arousal threshold. The perception threshold is the modulation level (e.g., amplitude) at which the patient can perceive or sense (e.g., while awake or conscious) that they are receiving a modulation signal. This is often because the patient can perceive or sense the muscular or motor response induced by the modulation signal. The arousal threshold is the modulation level (e.g., amplitude) that causes the patient to rouse or wake from sleep. This means that sub-threshold amplitudes are less likely to cause the patient discomfort or rouse the patient from sleep, which makes these amplitudes more comfortable than threshold or suprathreshold amplitudes.

Modulation response data, such as the data represented in FIGS. 10A and 1B, can be used to customize therapy for a given patient. For example, at least some embodiments of the present technology include determining a patient's perception threshold and/or arousal threshold, and delivering one or more modulation signals at one or more levels (e.g., amplitudes) less than the perception threshold and/or the arousal threshold. Determining a patient's perception threshold can involve delivering modulation signals at multiple (e.g., progressively increasing) amplitudes and asking the patient which of the modulation signals they could perceive. Determining the patient's arousal threshold can involve delivering modulation signals at multiple (e.g., progressively increasing) amplitudes while the patient is asleep to determine which amplitudes wake the patient. Many patients tolerate higher levels of modulation while asleep (and often do not consciously perceive this modulation because they are asleep). Accordingly, many patients have (or are expected to have) a higher arousal threshold than their perception threshold. In some embodiments, determining the patient's perception threshold and/or arousal threshold can include determining or quantifying the patient's response to a delivered modulation signal. For example, determining the patients' response can include calculating the patient's AHI and/or generating a dose-response curve that plots AHI against modulation amplitude. The patient's determined response to a plurality of modulation signals can be used to identify which modulation signal level provides an adequate or optimal patient response. For example, the patient's determined response to the modulation signals can be used to determine which modulation signal provides adequate improvements to airflow or other breathing activity while reducing or minimizing patient discomfort. In at least some embodiments, the delivered sub-threshold modulation signal can have an amplitude that is up to 1%, 5%, 10%, 15%, 20%, 25%, 30%, 40%, 50%, 60%, 70%, 75%, 80%, 90%, or 99% of the perception and/or arousal threshold. Delivering the one or more modulation signals at sub-threshold levels can stiffen and/or move one or more tissues defining the patient's airway and improve the patient's breathing without producing a full muscular contraction and without, or substantially without, causing discomfort (e.g., arousal), as described previously herein. In some embodiments, delivering the one or more modulation signals at the sub-threshold levels includes delivering one or more modulation signals determined using the dose-response curve described above.

In some embodiments, the present technology includes selecting an electrode pair to deliver one or more modulation signals based, at least in part, on a patient's modulation response data. Selecting the electrode pair can include delivering one or more modulation signals via different combinations of electrodes and determining the electrode pair that produces the best or optimal result. For example, as illustrated in FIG. 10A, the patient responded better to the first 2 mA modulation signal delivered during the third signal delivery period 1028c via the #1 and #3 electrodes than to the second 2 mA modulation signal delivered during the sixth signal delivery period 1028f via the #2 and #4 electrodes. Accordingly, the #1 and #3 electrodes can be selected for use during further trials and/or chronic use.

Although the sub-threshold modulation concepts are described above with reference to amplitudes, in these and/or other embodiments other modulation parameters can be adjusted to provide sub-threshold modulation. In at least some embodiments, for example, the pulse width of the modulation delivered to a patient can be adjusted to provide sub-threshold modulation, in addition to or in lieu of adjusting the amplitude. If a modulation signal delivered to a patient equals or exceeds a modulation and/or perception threshold for that patient, the pulse width of the modulation signal can be increased and/or the amplitude of the modulation signal can be decreased until, e.g., the modulation signal is below the modulation and/or perception threshold. The amplitude, pulse width, and/or one or more other modulation parameters (e.g., frequency, duty cycle, interpulse spacing, etc.) can be adjust manually (by, e.g., a user) or automatically.

5. Additional Devices, Systems, and Methods

Figure 11:
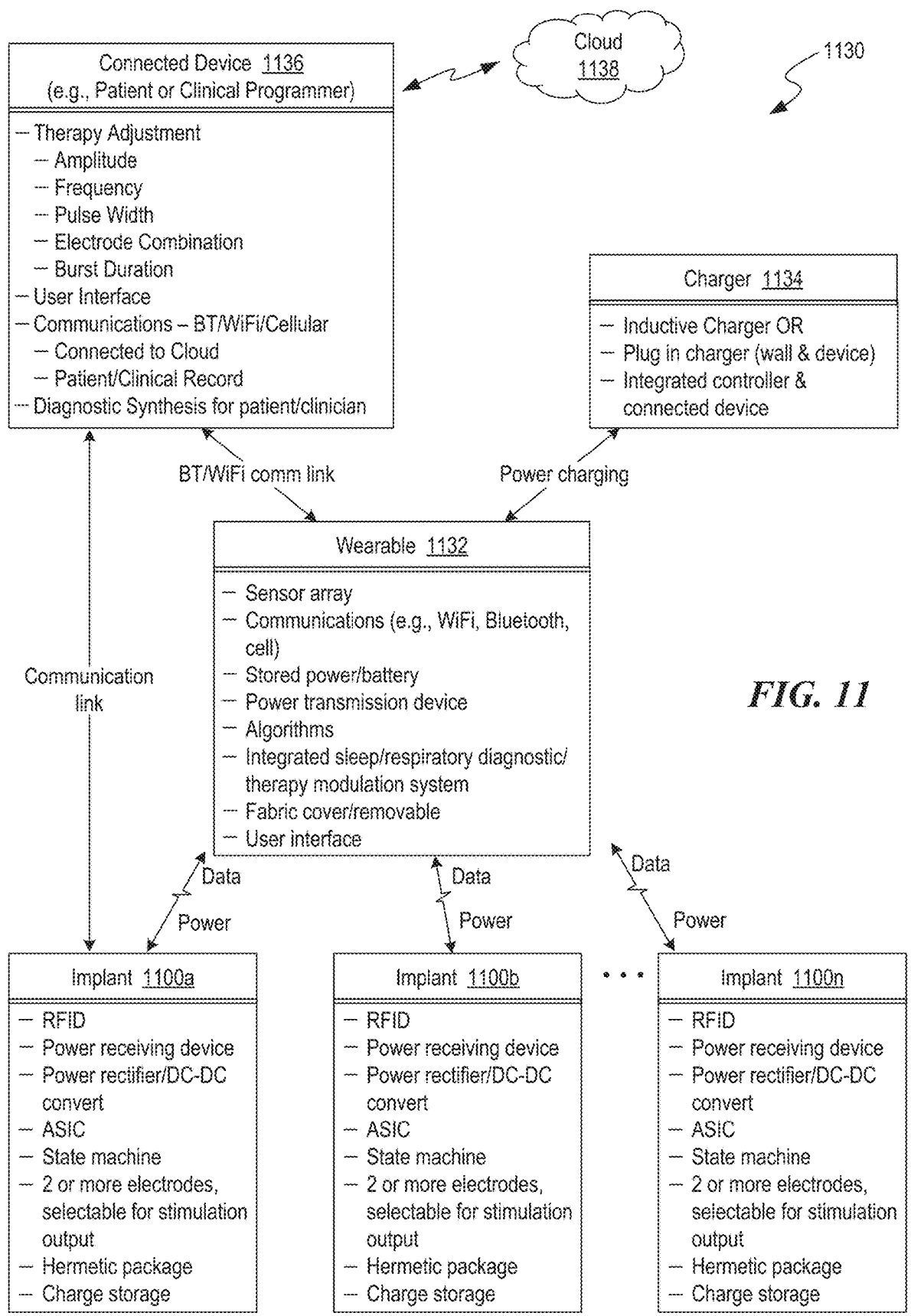
FIG. 11 is a block diagram illustrating elements of a system for treating sleep disorders in accordance with embodiments of the present technology.

FIG. 11 is a block diagram illustrating elements of a system 1130 for treating sleep disorders in accordance with embodiments of the present technology. The system 1130 can include a wearable device 1132, a charger 1134, one or more implants or signal delivery devices (e.g., a first signal delivery device 1100a, a second signal delivery device 1100b . . . an nth signal delivery device 1200n; referred to collectively as "signal delivery devices 1100") and a connected device or programmer 1136. In general, the programmer 1136 can transmit instructions for generating a modulation signal (e.g., signal delivery or waveform parameters) to the wearable device 1132, the wearable device 1132 can transmit the instructions and power to the signal delivery device(s) 1100, and individual signal delivery devices 1100 can generate the modulation signal according to the transmitted instructions and apply the modulation signal to a patient via electrodes carried by the signal delivery device(s) 1100. One or more of the signal delivery devices 1100 can be at least generally similar or identical in structure and/or function to the signal delivery device 100 of FIG. 1D. Additionally, one or more of the signal delivery devices 1100 can be implanted in a patient using one or more of the insertion paths described previously with reference to FIGS. 2A-9B, in one or more of the positions and/or orientations described previously with reference to FIGS. 2A-9B, and/or to deliver a modulation signal to one or more portions of the ansa cervicalis, one or more of the infrahyoid strap muscles, and/or one or more other target tissues described previously with reference to FIGS. 2A-9B.

The programmer 1136 can include a patient-operated programmer and/or a clinician-operated programmer and can be configured to control one or more characteristics of the modulation signal delivered to the patient. In a representative embodiment, the programmer 1136 can include a therapy adjustment module configured to select one or more of the electrodes carried by the signal delivery device(s) 1100 and adjust an amplitude, frequency, pulse width, burst duration, whether the electrode is active or inactive, and/or any other suitable signal delivery parameter. Additionally, the programmer 1136 can synthesize information (e.g., diagnostic and/or feedback information) received from a user, the wearable 1132, and/or one or more of the signal delivery devices 1100 and can adjust one or more of the signal delivery parameters based at least partially on the synthesized information. For example, the programmer 1136 can be configured to receive one or more inputs corresponding to a patient's perception threshold and/or arousal threshold, and adjust an amplitude of a modulation signal delivered to the patient based, at least in part, on the patient's perception threshold and/or arousal threshold. Additionally, or alternatively, the programmer 1126 can generate a dose-response curve that plots AHI against modulation amplitude, as described previously herein, and use the dose-response curve to adjust or recommend adjustments to the amplitude of the modulation signal delivered to the patient.

The programmer 1136 can transmit the signal delivery parameters to the signal delivery device(s) 1100 directly and/or via the wearable device 1132. For example, the programmer 1136 can be connected to individual ones of the signal delivery devices 1100 and/or the wearable device 1132 via a wired or wireless communication link, such as WiFi, Bluetooth ("BT"), cellular connectivity, and/or any other suitable communication link. In these and other embodiments, the programmer 1136 can be connected to a cloud 1138 and/or other computer service, e.g., to upload data received from the wearable device's 1132 sensors and/or to download information to the wearable device 1132 and/or the signal delivery device(s) 1100. In these and other embodiments, the programmer 1136 can include a display and/or a user interface. A user (e.g., the patient, the clinician, and/or other suitable user) can interact with and/or otherwise control one or more aspects of the programmer 1136 via the user interface, e.g., to manually adjust one or more of the signal delivery parameters, to read data received from the wearable device 1132 sensors, provide one or more inputs corresponding to a tissue collapse pattern, and/or carry out other tasks.

The wearable device 1132 can include a collar, chinstrap, mouthpiece, pillow, and/or can have other suitable form factors. The wearable device 1132 can include one or more sensors (e.g., a single sensor, an array of sensors, and/or other suitable sensor arrangements) configured to collect data associated with a patient. Representative data received from the patient can include respiratory rate, sleep state, wake state, heart rate, audio signals (corresponding to audible snoring, hypopnea events, and/or apnea events), body temperature, head orientation/position, saturated blood oxygen levels, air flow levels, thyroid movement, trachea movement, and/or tongue movement, photoplethysmography (PPG) data, among others, each of which can be received by a corresponding type of sensor (e.g., heart rate data from a heart rate sensor, head orientation/position data from an accelerometer, etc.). These data can be received via one or more corresponding sensors (e.g., body temperature from a temperature sensor, audio signals from a microphone or other audio sensor, etc.), and can correspond to a measure of the patient's respiratory performance, sleep state, wake state, and/or other suitable metrics, for example, metrics that are used to rate the patient on the Apnea-Hypopnea Index (AHI). Additionally, or alternatively, the wearable device 1132 can receive data from the individual signal delivery devices 1100, e.g., using backscatter, pulse width modulation, frequency modulation, and/or one or more other suitable techniques. For example the signal delivery devices 1100 can transmit a receipt to indicate that power has been received, and what magnitude the power is. This information can be used to autoregulate (up or down) the output of the signal delivery device's pulse generator, e.g., the transmitted signal and phase.

The wearable device 1132 can further include a power source (e.g., a stored power device such as battery), one or more power transmission devices configured to transmit power and/or signal delivery parameters to the signal delivery device(s) 1100, and one or more algorithms configured to control one or more aspects of the operation of the wearable device 1132. Individual ones of the sensors can collect data associated with the patient, such as a patient's sleep state and/or respiratory performance. The one or more algorithms can be configured to adjust at least one of the signal delivery parameters based at least partially on the data collected by the sensors. In a representative embodiment, the wearable 1132 can include an integrated sleep, respiratory diagnostics, and/or therapy modulation system configured to adjust or otherwise control one or more delivery parameters of the modulation signal delivered to the patient based on the collected sleep state and/or respiratory performance data, e.g., via one of more algorithms.

In some embodiments, the wearable device 1132 can further include a cover or housing, at least a portion of which may be removeable, e.g., to expose an interior or interior portion of the wearable device 1132. In these and other embodiments, the wearable device 1132 cover can include fabric, or any other suitable material. Optionally, the wearable device 1132 can include a reduced-scope and/or simplified user interface configured to allow a user to interact with and/or otherwise control one or more of the elements of the wearable device 1132, e.g., without using the programmer 1136. For example the wearable device user interface may allow the user to check a charging status of the power source, power on and/or off the wearable device 1132, adjust one or more of the signal delivery parameters, configured and/or verify therapy delivery, select one or more therapy presets, confirm and/or verify placement of the wearable device, etc.

The charger 1134 for the wearable device 1132 can be configured to supply power to the wearable device's 1132 power source. The charger 1134 can include a wireless (e.g., inductive) charger, a wired charger (e.g., wall-plug, charging cable, etc.), and/or any other suitable charger or charging device. Optionally, the charger 1134 can include an integrated controller and/or a connected device, e.g., to control the charging of the wearable device 1132 and/or to upload/download data to the wearable device 1132 while the wearable device 1132 is charging.

The one or more signal delivery devices 1100 can include an RFID component (e.g., a unique RFID tag that can be used to identify and/or locate the associated signal delivery device 1100*a-n*), a power receiving device (e.g., one or more RF power antennas, one or more inductive coils, etc.), a power rectifier/DC-DC converter, circuitry (e.g., one or more application-specific integrated circuits (ASICs), a state machine, etc.), a signal generator, and two or more electrodes that are each individually selectable to deliver a modulation signal to a patient. The power receiving device can receive power from the power transmission component (e.g., one or more RF power antennas, one or more inductive coils, etc.) of the wearable device. The power rectifier/DC-DC converter can be operably coupled to the electrode receiver antenna and can be configured to transmit the received power to the signal generator. Additionally, each of the signal delivery devices 1100 can receive, via the power receiving device and/or one or more other communication components, information regarding one or more of the delivery parameters of the modulation signal to be generated by the signal generator and/or delivered to the patient via at least one of the electrodes of the signal delivery device(s) 1100. The circuitry can include machine-readable instructions associated with the operation of the signal delivery device(s) 1100. For example, the circuitry can include instructions that, when executed, can cause the signal generator to generate the modulation signal having the signal delivery parameter(s) received via the electrode receiver antenna. In these and other embodiments, the power receiving device and/or the one or more other communication components can be used to transmit information associated with the signal delivery device 1100 to the wearable device 1132. For example, the signal delivery device 1100 can transmit information to the wearable device 1132 associated with one or more of the signal delivery parameters of the modulation signal being applied to the patient. In these and other embodiments, one or more of the signal delivery devices 1100 can include a hermetic package or housing configured such that the signal delivery device(s) 1100 can be implanted within a patient.

In some embodiments, one or more of the signal delivery devices 1100 are passive devices that do not include an onboard pulse generator configured to generate modulation signals. Instead, the passive signal delivery device can wirelessly receive a power signal from the wearable device 1132 and transmit the received power signal to the wearer via the electrodes. The passible signal delivery device may condition or otherwise process the received power signal, but does not use the received power signal to power an onboard pulse generator.

Figure 12:
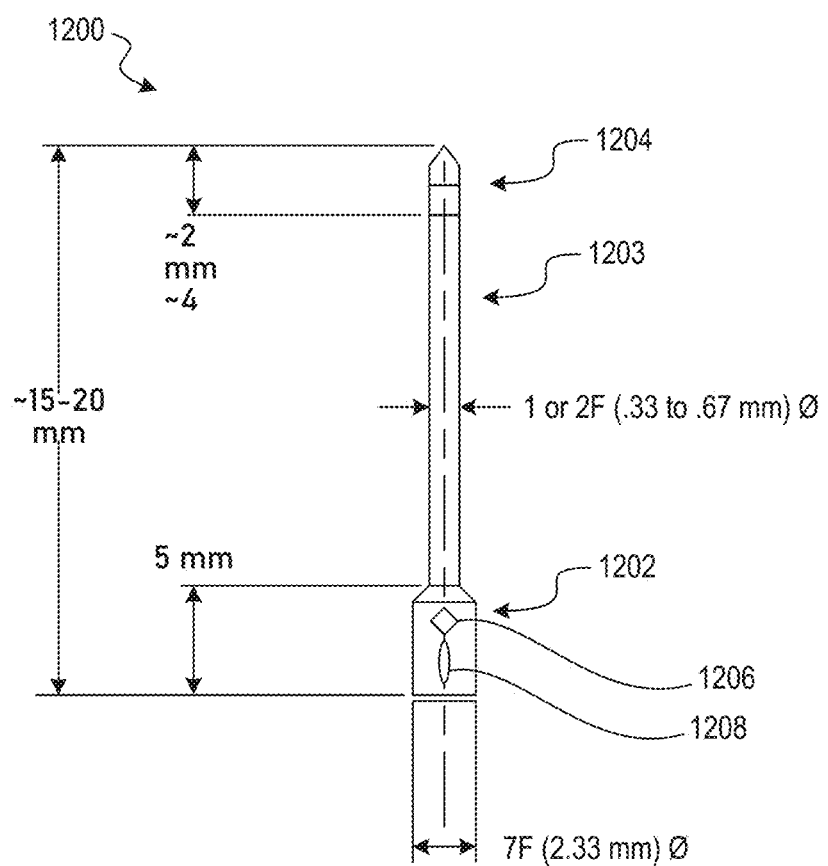
FIG. 12 is a partially schematic side view illustrating another signal delivery device configured in accordance with embodiments of the present technology.

FIG. 12 is a partially schematic side view illustrating another signal delivery device 1200 configured in accordance with embodiments of the present technology. The dimensions shown in FIG. 12 are for illustration purposes only and, in at least some embodiments, all or one or more portions of the signal delivery device 1200 can have dimensions other than those shown in FIG. 12. In at least some embodiments, the signal delivery device 1200 can be at least generally similar or identical in structure and/or function to the signal delivery device 100 of FIG. 1D. For example, the illustrated signal delivery device 1200 includes a housing 1202, an electrode array 1204 coupled to the housing 1202, a signal generator 1206, and an antenna 1208. The electrode array 1204 can include a monopolar electrode array or a bipolar (or other multi-polar) electrode array. In some embodiments, the electrode array 1204 can include electrodes formed from Pt and/or Ir, such as Pt90/Ir10, and/or one or more other suitable materials. The housing 1202 can be configured to hermetically contain one or more circuit components of the signal delivery device 1200, including the signal generator 1206 and/or the antenna 1208. All or a portion of the housing 1202 can be formed from Pt, PtIr, Ti6AL4V, epoxy, a TPE, one or more ceramics, and/or one or more other suitable materials. For example, a portion of the housing 1202 surrounding the antenna 1208 can be formed from epoxy, ceramic, TPE, and/or one or more other materials configured to prevent, or at least partially prevent, interference with power transmission to the antenna 1208. Optionally, at least a portion of the housing 1202 can be electrically activatable and configured to serve as an electrode, e.g., when the electrode array 1204 is monopolar.

Additionally, the signal delivery device 1200 includes a lead portion 1203 coupled to the housing 1202 and carrying the electrode array 1204. The lead portion 1203 can be at least generally flexible and/or otherwise configured to undergo elastic deformation. In some embodiments, the lead portion 1203 is separable from the housing 1202 and configured to be coupled to and/or docked with the housing 1202, e.g., in vivo. In some embodiments, the lead portion 1203 can be formed from one or more thermoplastic polyurethanes (TPUs), such as Tecothane™, and/or one or more other suitable materials. The lead portion 1203 can contain one or more wires and/or other conductive elements that electrically couple the electrode array 1204 to the signal generator 1206. The wires/conductive elements can be formed from MP35N and/or one or more other suitable conductive materials.

Accordingly, in some aspects of the present technology, one or more signal delivery devices can be implanted in a patient to deliver one or more modulation signals to a patient's ansa cervicalis nerve and/or one or more of the muscles innervated by the ansa cervicalis nerve. Delivering modulation signals to the ansa cervicalis nerve can induce caudal traction, or at least stiffen one or more tissues defining the patient's airway, to improve the patient's airflow and/or otherwise address breathing obstructions. Ansa cervicalis modulation, on its own, is expected to address breathing obstructions in many patients. Modulating the ansa cervicalis to improve a patient's airflow can be accomplished at lower amplitudes compared to other target tissues (e.g., the hypoglossal nerve, one or more of the infrahyoid strap muscles, etc.) and is accordingly expected to address breathing obstructions with lower rates of patient arousal and/or reduced power transmission requirements. Patients for whom ansa cervicalis modulation is insufficient to adequately improve airflow can receive another signal delivery device, for example, implanted to deliver modulation signals to the patients' hypoglossal nerve, such that these patient's hypoglossal nerves can be modulated as needed to improve the patients' airflow. Similarly, patients for whom hypoglossal nerve modulation is insufficient to adequately improve airflow can receive another signal delivery device, for example, implanted to deliver modulation signals to the patients' ansa cervicalis, such that these patients' ansa cervicalis nerves can be modulated as needed to improve the patients' airflow.

6. Examples

The following examples provide further embodiments of the present technology:

1. A method for addressing sleep apnea in a patient, the method comprising:
   percutaneously inserting an implantable signal delivery device at an insertion point on the patient's neck;
   moving the signal delivery device in a medial-to-lateral direction toward an ansa cervicalis nerve of the patient; and
   implanting the signal delivery device at a target location at least proximate to the ansa cervicalis nerve, wherein the signal delivery device includes at least one electrode positioned to deliver a modulation signal to tissue at least proximate to the target location.
2. The method of example 1 wherein moving the signal delivery device in the medial-to-lateral direction includes moving the signal delivery device away from a mid-sagittal plane of the patient at an angle relative to the mid-sagittal plane of between about between about 20 degrees and about 80 degrees.
3. The method of example 2 wherein the angle is between about 45 degrees and about 80 degrees.
4. The method of example 3 wherein the angle is about 60 degrees and about 80 degrees.
5. The method of examples 1-4 wherein implanting the signal delivery device includes implanting the signal delivery device at least proximate to a superior branch of the ansa cervicalis nerve of the patient.
6. The method of examples 1-4 wherein implanting the signal delivery device includes implanting the signal delivery device at least proximate to an inferior branch of the ansa cervicalis nerve of the patient.
7. The method of examples 1-4 wherein implanting the signal delivery device includes implanting the signal delivery device at least proximate to a branch of the ansa cervicalis nerve innervating an omohyoid muscle of the patient.
8. The method of examples 1-4 wherein implanting the signal delivery device includes implanting the signal delivery device at least proximate to a branch of the ansa cervicalis nerve innervating a sternohyoid muscle of the patient.
9. The method of examples 1-4 wherein implanting the signal delivery device includes implanting the signal delivery device at least proximate to a branch of the ansa cervicalis nerve innervating a sternothyroid muscle of the patient.
10. The method of examples 1-4 wherein implanting the signal delivery device includes implanting the signal delivery device at least proximate to a branch of the ansa cervicalis nerve innervating both a sternohyoid muscle of the patient and a sternothyroid muscle of the patient.
11. The method of examples 1-4 wherein implanting the signal delivery device includes implanting the signal delivery device at least proximate to a distal end of a branch of the ansa cervicalis nerve to deliver the modulation signal to a motor point of the branch innervating one of a sternohyoid muscle of the patient, a sternothyroid muscle of the patient, or an omohyoid muscle of the patient.
12. The method of examples 1-4 wherein implanting the signal delivery device at least proximate to the target location includes implanting the signal delivery device at least proximate to a strap muscle of the patient.
13. The method of example 12 wherein implanting the signal delivery device at least proximate to the strap muscle includes implanting the signal delivery device at least proximate to a sternothyroid muscle, a sternohyoid muscle, an omohyoid muscle, and/or a thyrohyoid muscle of the patient.
14. The method of examples 1-13, further comprising delivering the signal to the target tissue to increase the stability of at least a portion of an airway of the patient, which includes one or more of (i) increasing a stiffness of at least a portion of a pharyngeal wall of the airway of the patient, (ii) increasing a dimension of a retropalatal airway of the patient, and (iii) decreasing a resistance to airflow through at least the portion of the airway.
15. The method of examples 1-14, further comprising delivering the signal to the target tissue to induce caudal traction by lowering one or both of a hyoid bone of the patient and/or thyroid cartilage of the patient.
16. The method of examples 1-15 wherein percutaneously inserting the signal delivery device includes moving the signal delivery device in an anterior-to-posterior direction.

17. The method of examples 1-16 wherein percutaneously inserting the signal delivery device includes moving the signal delivery device in an inferior-to-superior direction.
18. The method of examples 1-16 wherein percutaneously inserting the signal delivery device includes moving the signal delivery device in a superior-to-inferior direction.
19. The method of examples 1-18 wherein percutaneously inserting the signal delivery device into the neck includes percutaneously inserting the signal delivery device along an insertion path angled relative to the mid-sagittal plane.
20. The method of example 19 wherein the insertion path includes a first path portion at a first angle relative to the mid-sagittal plane and a second path portion at a second angle relative to the mid-sagittal plane, the second angle different than the first angle.
21. The method of example 20 wherein the first path portion is proximal to the insertion point, and wherein percutaneously inserting the signal delivery device along the second path portion includes percutaneously inserting the signal delivery device along the second path portion at a second angle greater than the first angle.
22. The method of examples 1-21, further comprising delivering the modulation signal via the signal delivery device, wherein delivering the modulation signal includes inducing caudal traction to at least partially address the patient's sleep apnea.
23. The method of examples 1-22, further comprising delivering the modulation signal via the signal delivery device, wherein delivering the modulation signal includes at least partially preventing collapse of the patient's airway.
24. The method of examples 1-23, further comprising delivering the modulation signal via the signal delivery device, wherein delivering the modulation signal includes at least partially preventing collapse of at least a portion of the patient's retropalatal tissues.
25. The method of example 24 wherein at least partially preventing collapse of at least the portion of the patient's retropalatal tissues includes preventing collapse of at least a portion of the patient's velopharyngeal and/or oropharyngeal tissues.
26. The method of examples 1-25, further comprising delivering the modulation signal via the signal delivery device, wherein delivering the modulation signal includes reducing a number a frequency, and/or a severity of one or more apneic events experienced by the patient over a predetermined time period.
27. The method of examples 1-26, further comprising delivering the modulation signal via the signal delivery device, wherein delivering the modulation signal includes reducing a number a frequency, and/or a severity of one or more hypopneic events experienced by the patient over a predetermined time period.
28. The method of example 26 or example 27 wherein the predetermined time period includes during delivery of the modulation signal.
29. The method of examples 26-28 wherein the predetermined time period includes a period of time after delivery of the modulation signal.
30. The method of any of examples 1-29, further comprising:
generating, via one or more sensors of the signal delivery device, physiological data; and
delivering the modulation signal to the target tissue based, at least in part, on the generated physiological data.
31. The method of example 30 wherein delivering the modulation signal includes adjusting one or more parameters of the modulation signal based, at least in part, on the generated physiological data.
32. The method of any of examples 1-31, further comprising receiving power wirelessly via an antenna of the signal delivery device.
33. The method of example 32 wherein receiving power wirelessly includes receiving RF power.
34. The method of example 32 wherein receiving power wirelessly includes receiving power inductively.
35. The method of any of examples 32-34, further comprising storing at least a portion of the received power in a charge storage device.
36. The method of example 35 wherein the charge storage device has a total charge storage capacity of no more than 1 second, 5 seconds, 10 seconds, 15 second, 20 seconds, 25 seconds, 30 seconds, 1 minute, 2 minutes, or 5 minutes.
37. A method for addressing sleep apnea in a patient, the method comprising:
programming a first signal delivery device to deliver a first modulation signal to a first target tissue of the patient from a position at least proximate to an ansa cervicalis nerve of the patient; and
programming a second signal delivery device to deliver a second modulation signal to a second target tissue of the patient, different than the first target tissue, and at least proximate to one or more anterior branches of a hypoglossal nerve of the patient.
38. The method of example 37 wherein—
programming the first signal delivery device includes programming the first signal delivery device to deliver the first modulation signal with a first signal delivery parameter, and
programming the second signal delivery device includes programming the second signal delivery device to deliver the second modulation signal with a second signal delivery parameter different than the first signal delivery parameter.
39. The method of examples 37 or 38 wherein—
programming the first signal delivery device includes programming the first signal delivery device to deliver the first modulation signal with a first amplitude, and
programming the second signal delivery device includes programming the second signal delivery device to deliver the second modulation signal with a second amplitude different than the first amplitude.
40. The method of examples 37-39 wherein—
programming the first signal delivery device includes programming the first signal delivery device to deliver the first modulation signal with a first frequency, and
programming the second signal delivery device includes programming the second signal delivery device to deliver the second modulation signal with a second frequency different than the first frequency.
41. The method of examples 37-40 wherein—
programming the first signal delivery device includes programming the first signal delivery device to deliver the first modulation signal with a first pulse width, and
programming the second signal delivery device includes programming the second signal delivery device to deliver the second modulation signal with a second pulse width different than the first pulse width.

42. The method of examples 37-41 wherein—
programming the first signal delivery device includes programming the first signal delivery device to change an amplitude of the first electrical during delivery, and
programming the second signal delivery device includes programming the second signal delivery device to change an amplitude of the second electrical during delivery.
43. The method of example 42 wherein changing the amplitude of one or both of the first modulation signal and the second modulation signal includes ramping the amplitude from a first value to a second value greater than the first value.
44. The method of examples 37-43 wherein—
programming the first signal delivery device includes programming the first signal delivery device to deliver the first modulation signal during a time period, and
programming the second signal delivery device includes programming the second signal delivery device to deliver the second modulation signal during the time period.
45. The method of examples 37-44 wherein—
programming the first signal delivery device includes programming the first signal delivery device to deliver the first modulation signal during a first time period, and
programming the second signal delivery device includes programming the second signal delivery device to deliver the second modulation signal during a second time period at least partially different than the first time period.
46. The method of example 45 wherein the second time period is after the first time period.
47. The method of example 45 wherein the second time period is concurrent with a portion of the first time period.
48. The method of any of examples 37-47 wherein—
programming the first signal delivery device to deliver the first modulation signal includes programming the first signal delivery device to deliver the first modulation signal based, at least in part, on data received via a sensor; and/or
programming the second signal delivery device to deliver the second modulation signal includes programming the second signal delivery device to deliver the second modulation signal based, at least in part, on data received via the sensor.
49. The method of example 48 wherein—
programming the first signal delivery device to deliver the first modulation signal based, at least in part, on data received via the sensor includes programming the first signal delivery device to vary at least one first signal delivery parameter of the first modulation signal based, at least in part, on the data or a change in the data; and/or
programming the second signal delivery device to deliver the second modulation signal based, at least in part, on data received via the sensor includes programming the second signal delivery device to vary at least one second signal delivery parameter of the second modulation signal based, at least in part, on the data or the change in the data.
50. A method for addressing sleep apnea in a patient, the method comprising:
activating a first signal delivery device to deliver a first modulation signal to a first target tissue of the patient from a position at least proximate to an ansa cervicalis nerve of the patient; and
activating a second signal delivery device to deliver a second modulation signal to a second target tissue of the patient, different than the first target tissue, and at least proximate to one or more anterior branches of a hypoglossal nerve of the patient.
51. A method for addressing sleep apnea in a patient, the method comprising:
percutaneously inserting an implantable signal delivery device at an insertion point on the patient's neck;
moving the signal delivery device in a medial-to-lateral direction toward a branch of an ansa cervicalis nerve of the patient that innervates a sternohyoid muscle of the patient and a sternothyroid muscle of the patient; and
implanting the signal delivery device at a target location at least proximate to a motor point of the branch at which the branch innervates the sternohyoid muscle or the sternothyroid muscle, wherein the signal delivery device includes at least one electrode positioned to deliver a modulation signal to tissue at least proximate to the target location, and
delivering a modulation signal to at least a portion of the branch to induce a motor response in one or both of the sternohyoid muscle and the sternothyroid muscle to address the patient's sleep apnea.
52. The method of example 51 wherein the branch includes a first sub-branch innervating the sternohyoid muscle and a second sub-branch innervating the sternothyroid muscle, and wherein implanting the signal delivery device at the target location includes implanting the signal delivery device at least partially between the first sub-branch and the second sub-branch.
53. The method of example 51 wherein the branch includes a first sub-branch innervating the sternohyoid muscle and a second sub-branch innervating the sternothyroid muscle, and wherein implanting the signal delivery device at the target location includes implanting the signal delivery device across the first sub-branch and the second sub-branch.
54. The method of example 51 wherein the branch includes a first sub-branch innervating the sternohyoid muscle and a second sub-branch innervating the sternothyroid muscle, and wherein implanting the signal delivery device at the target location includes implanting the signal delivery device transverse to the first sub-branch and the second sub-branch.
54. The method of example 51 wherein the motor point of the branch includes a plurality of anterior branches, and wherein implanting the signal delivery device at the target location includes implanting the signal delivery device to deliver the modulation signal to individual ones of the plurality of anterior branches.
55. The method of example 54 wherein implanting the signal delivery device to deliver the modulation signal to individual ones of the plurality of anterior branches includes implanting the signal delivery device with an electrode array of the signal delivery device at least generally transverse to at least a subset of the plurality of anterior branches.
56. A system for addressing a breathing obstruction in a patient, the system comprising:
an implantable signal delivery device configured to be positioned to deliver a modulation signal to the patient's ansa cervicalis nerve, and a controller communicatively coupled to the implantable signal delivery device and configured to—
  receive an input corresponding to modulation threshold of the patient,
  determine a modulation parameter based, at least in part, on the input, and
  instruct the signal delivery device to generate the modulation signal based, at least in part, on the modulation parameter.

57. The system of example 56 wherein the modulation threshold includes an arousal threshold at which the modulation signal causes the patient to rouse from sleep.

58. The system of example 56 or example 57 wherein the modulation threshold includes a perception threshold at which the patient consciously perceives the delivery of the modulation signal.

59. The system of any of examples 56-58 wherein the modulation parameter includes an amplitude of the modulation signal.

60. The system of any of examples 56-59 wherein the controller is configured to determine the modulation parameter by reducing the modulation signal by a predetermined amount.

61. The system of any of examples 56-60 wherein the modulation threshold is associated with a first value of the modulation parameter, and wherein the controller is configured to determine a second value of the modulation parameter different than the first value.

62. The system of any of examples 56-61 wherein the modulation threshold is associated with a first value of the modulation parameter, and wherein the controller is configured to determine a second value of the modulation parameter less than the first value.

63. The system of any of examples 56-62 wherein the implantable signal delivery device is a first implantable signal delivery device, wherein the modulation signal is a first modulation signal, and wherein the system further comprises a second implantable signal delivery device configured to be positioned to deliver a second modulation signal to the patient's hypoglossal nerve.

64. A method of addressing a breathing obstruction in a patient, the method comprising:
delivering a first modulation signal to a patient's ansa cervicalis nerve;
determining a first value of a modulation parameter associated with a modulation threshold of the patient's ansa cervicalis nerve; and
delivering a second modulation signal to the patient's ansa cervicalis nerve at a second value of the modulation parameter different than the modulation threshold.

65. The method of example 64 wherein the modulation threshold includes an arousal threshold at which the modulation signal causes the patient to rouse from sleep.

66. The method of example 64 or example 65 wherein the modulation threshold includes a perception threshold at which the patient consciously perceives the delivery of the modulation signal.

67. The method of any of examples 64-66 wherein the modulation parameter includes an amplitude of the modulation signal.

68. The method of any of examples 64-67 wherein delivering the second modulation signal includes reducing the first value of the modulation parameter by a predetermined amount to determine the second value of the modulation parameter.

69. The method of any of examples 64-68 wherein the second value of the modulation parameter is less than the first value.

70. A system for addressing a breathing obstruction in a patient, the system comprising:
an implantable signal delivery device configured to be positioned to deliver a modulation signal to an ansa cervicalis nerve of the patient, and
a controller communicatively coupled to the implantable signal delivery device and configured to—
  receive an input corresponding to a modulation threshold of the patient's ansa cervicalis nerve,
  determine a modulation parameter value different than the modulation threshold based at least in part on the input, and
  instruct the implantable signal delivery device to generate the modulation signal based at least in part on the modulation parameter value.

71. The system of claim 70 wherein the modulation parameter value is less than the modulation threshold by a predetermined amount.

72. The system of claim 70 wherein the modulation threshold is a first value of a modulation parameter, and wherein the modulation parameter value is a second value of the modulation parameter less than the first value.

73. The system of claim 72 wherein the modulation parameter includes a modulation amplitude.

74. The system of claim 70 wherein the modulation threshold includes an arousal threshold at which the modulation signal causes the patient to rouse from sleep.

75. The system of claim 70 wherein the modulation threshold includes a perception threshold at which the patient consciously perceives the delivery of the modulation signal.

76. The system of claim 70 wherein the modulation parameter includes a modulation pulse width.

77. The system of claim 70 wherein the modulation parameter includes a modulation pulse width, wherein the modulation threshold includes a first pulse width value, and wherein the modulation parameter value includes a second pulse width value greater than the first pulse width value.

78. A method of addressing a breathing obstruction in a patient, the method comprising:
causing a first modulation signal to be delivered to an ansa cervicalis nerve of the patient to produce a first response in a muscle of the patient innervated by the ansa cervicalis nerve;
obtaining a first value of a modulation parameter associated with a modulation threshold of the patient's ansa cervicalis nerve; and
causing a second modulation signal to be delivered to the patient's ansa cervicalis nerve at a second value of the modulation parameter different than the modulation threshold to produce a second response in the muscle different than the first response.

79. The method of example 78 wherein the first response includes a full muscular response and wherein the second response is less than the full muscular response.

80. The method of example 78 or 79 wherein the muscle includes a sternothyroid muscle of the patient and/or a sternohyoid muscle of the patient.

81. The method of any of examples 78-80 wherein obtaining the first value of the modulation parameter associated with the modulation threshold includes obtaining a first value of the modulation parameter associated with an arousal threshold at which modulation of the ansa cervicalis nerve causes the patient to rouse from sleep.
82. The method of any of examples 78-81 wherein obtaining the first value of the modulation parameter associated with the modulation threshold includes obtaining a first value of the modulation parameter associated with a perception threshold at which the patient consciously perceives modulation of the ansa cervicalis nerve.
83. The method of any of examples 78-82 wherein—
obtaining the first value of the modulation parameter includes obtaining a first modulation amplitude associated with the modulation threshold of the patient's ansa cervicalis nerve, and
causing the second modulation signal to be delivered includes causing the second modulation signal to be delivered at a second modulation amplitude less than the first modulation amplitude.
84. The method of any of examples 78-83 wherein delivering the second modulation signal includes reducing the first value of the modulation parameter by a predetermined amount.
85. The method of any of examples 78-84 wherein the second value of the modulation parameter is less than the first value and the modulation threshold.
86. A method for addressing sleep apnea in a patient, the method comprising:
percutaneously inserting an implantable signal delivery device at an insertion point on the patient's neck;
moving the signal delivery device in a lateral-to-medial direction toward an ansa cervicalis nerve of the patient; and
implanting the signal delivery device at a target location at least proximate to the ansa cervicalis nerve, wherein the signal delivery device includes at least one electrode positioned to deliver a modulation signal to tissue at least proximate to the target location.
87. The method of example 86 wherein moving the signal delivery device includes moving the signal delivery device toward from a mid-sagittal plane of the patient at an angle relative to the mid-sagittal plane of between about between about 20 degrees and about 80 degrees.
88. The method of example 86 or 87 wherein moving the signal delivery device includes moving the signal delivery device toward from a mid-sagittal plane of the patient at an angle relative to the mid-sagittal plane of between about 45 degrees and about 80 degrees.
89. The method of any of examples 86-88, further comprising, before percutaneously inserting the implantable signal delivery device, rotating the patient's head posteriorly to expose the insertion point.
90. The method of any of examples 86-89 wherein implanting the signal delivery device includes implanting the signal delivery device at least proximate to an inferior branch of the ansa cervicalis nerve of the patient.
91. The method of any of examples 86-90 wherein implanting the signal delivery device includes implanting the signal delivery device at least proximate to a branch of the ansa cervicalis nerve innervating a sternohyoid muscle, a sternothyroid muscle, or an omohyoid muscle of the patient.
92. The method of any of examples 86-91 wherein implanting the signal delivery device includes implanting the signal delivery device at least proximate to a branch of the ansa cervicalis nerve innervating both a sternohyoid muscle of the patient and a sternothyroid muscle of the patient.
93. The method of any of examples 86-92 wherein implanting the signal delivery device includes implanting the signal delivery device at least proximate to a distal end of a branch of the ansa cervicalis nerve to deliver the modulation signal to a motor point of the branch innervating one of a sternohyoid muscle of the patient, a sternothyroid muscle of the patient, or an omohyoid muscle of the patient.
94. The method of any of examples 86-93 wherein implanting the signal delivery device at least proximate to the target location includes implanting the signal delivery device at least proximate to a sternothyroid muscle, a sternohyoid muscle, an omohyoid muscle, and/or a thyrohyoid muscle of the patient.
95. The method of any of examples 86-94, further comprising delivering the modulation signal to the target tissue to increase the stability of at least a portion of an airway of the patient, which includes one or more of (i) increasing a stiffness of at least a portion of a pharyngeal wall of the airway of the patient, (ii) increasing a dimension of a retropalatal airway of the patient, and (iii) decreasing a resistance to airflow through at least the portion of the airway.
96. The method of any of examples 86-95, further comprising delivering the modulation signal to the target tissue to induce caudal traction by lowering one or both of a hyoid bone of the patient and/or thyroid cartilage of the patient.
97. The method of any of examples 86-96 wherein percutaneously inserting the signal delivery device includes moving the signal delivery device in an anterior-to-posterior direction.
98. The method of any of examples 86-97 wherein percutaneously inserting the signal delivery device includes moving the signal delivery device in an inferior-to-superior direction.
99. The method of any of examples 86-97 wherein percutaneously inserting the signal delivery device includes moving the signal delivery device in a superior-to-inferior direction.

From the foregoing, it is believed that positioning a signal delivery device to deliver a modulation signal to the ansa cervicalis nerve AC will reduce or prevent airway collapse in the retropalatal (e.g., velopharyngeal and oropharyngeal) region of the patient's airway, without or generally without impacting tongue base collapse and/or interfering with the ability of other modulation (e.g., hypoglossal nerve modulation) to reduce or prevent tongue base collapse. Additionally, the combination of ansa cervicalis AC modulation and hypoglossal nerve modulation is expected to provide a therapeutic solution for a wider range of collapse sites in the upper airway, resulting in (1) more effective therapy for patients whose collapse pattern (e.g., velopharyngeal collapse pattern) would not be completely targeted by hypoglossal nerve modulation alone, and (2) a broadened potential population for whom neuromodulation can be an effective therapy by targeting an additional collapse site. For example, and as described previously herein, multi-site signal delivery is expected to increase the potential patient responder population to include, e.g., patients who would not otherwise respond to hypoglossal nerve modulation alone (e.g., patients with primary velopharyngeal collapse, no soft palate coupling, BMI>32, and/or complete concentric collapse of the airway). In these and other embodiments, the positions/orientations described herein are expected to reduce or minimize changes to the position/orientation of the signal delivery device during insertion and/or after implantation, and/or increase the speed and/or precision with which the signal delivery device can be positioned at least proximate to the target location.

It will be appreciated that specific embodiments of the disclosed technology have been described herein for purposes of illustration, but that various modifications may be made without deviating from the technology. For example, the signal delivery device can include a lead, and one or more of the electrodes of the signal delivery device can be carried by the lead. Certain aspects of the technology described in the context of particular embodiments may be combined or eliminated in other embodiments. For example, two signal delivery devices can be implanted to bilaterally target the patient's tissues (e.g., left and right ansa cervicalis nerves) and/or to target different tissues on left and right sides of the patient (e.g., a left ansa cervicalis nerve and a right infrahyoid strap muscle of the patient). Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

As used herein, the phrase "and/or," as in "A" and/or "B" refers to A alone, B alone and both A and B. Unless otherwise stated, the terms "generally," "about," and "approximately" refer to values within 10% of a stated value. For example, the use of the term "about 100" refers to a range of 90 to 110, inclusive. In instances where relative terminology is used in reference to something that does not include a numerical value, the terms are given their ordinary meaning to one skilled in the art.

To the extent any materials incorporated herein by reference conflict with the present disclosure, the present disclosure controls.

We claim:

1. A method for addressing sleep apnea in a patient, the method comprising:
    percutaneously inserting an implantable signal delivery device at an insertion point on the patient's neck;
    moving the signal delivery device in a lateral-to-medial direction toward a branch of an ansa cervicalis nerve of the patient that bifurcates to innervate both an inferior belly of a sternohyoid muscle of the patient and a sternothyroid muscle of the patient; and
    implanting the signal delivery device at a target location at least proximate to the branch of the ansa cervicalis nerve, wherein the signal delivery device includes at least one electrode positioned to deliver a modulation signal to tissue at least proximate to the target location and thereby cause a motor response in the sternohyoid muscle and the sternothyroid muscle to address the patient's sleep apnea.

2. The method of claim 1 wherein moving the signal delivery device includes moving the signal delivery device toward a mid-sagittal plane of the patient at an angle relative to the mid-sagittal plane of between about 20 degrees and about 80 degrees.

3. The method of claim 1 wherein moving the signal delivery device includes moving the signal delivery device toward a mid-sagittal plane of the patient at an angle relative to the mid-sagittal plane of between about 45 degrees and about 80 degrees.

4. The method of claim 1, further comprising, before percutaneously inserting the implantable signal delivery device, rotating the patient's head posteriorly to expose the insertion point.

5. The method of claim 1 wherein implanting the signal delivery device includes implanting the signal delivery device at least proximate to an inferior branch of the ansa cervicalis nerve of the patient.

6. The method of claim 1 wherein implanting the signal delivery device includes implanting the signal delivery device at least proximate to a distal end of the branch of the ansa cervicalis nerve to deliver the modulation signal to a motor point of the branch.

7. The method of claim 1 wherein implanting the signal delivery device at least proximate to the target location includes implanting the signal delivery device at least proximate to a sternothyroid muscle, a sternohyoid muscle, an omohyoid muscle, and/or a thyrohyoid muscle of the patient.

8. The method of claim 1, further comprising delivering the modulation signal to the target tissue to increase the stability of at least a portion of an airway of the patient, which includes one or more of (i) increasing a stiffness of at least a portion of a pharyngeal wall of the airway of the patient, (ii) increasing a dimension of a retropalatal airway of the patient, and (iii) decreasing a resistance to airflow through at least the portion of the airway.

9. The method of claim 1, further comprising delivering the modulation signal to the target tissue to induce caudal traction by lowering one or both of a hyoid bone of the patient and/or thyroid cartilage of the patient.

10. The method of claim 1 wherein percutaneously inserting the signal delivery device includes moving the signal delivery device in an anterior-to-posterior direction.

11. The method of claim 1 wherein percutaneously inserting the signal delivery device includes moving the signal delivery device in an inferior-to-superior direction.

12. The method of claim 1 wherein percutaneously inserting the signal delivery device includes moving the signal delivery device in a superior-to-inferior direction.

13. The method of claim 1 wherein implanting the signal delivery device at the target location includes implanting the signal delivery device at least partially between the sternohyoid muscle and the sternothyroid muscle.

14. The method of claim 1 wherein the branch bifurcates into a first sub-branch that innervates the inferior belly of the sternohyoid muscle and a second sub-branch that innervates the sternothyroid muscle, and wherein implanting the signal delivery device at the target location includes implanting the signal delivery device at least partially between the first sub-branch and the second sub-branch.

15. The method of claim 1 wherein the branch bifurcates into a first sub-branch that innervates the inferior belly of the sternohyoid muscle at one or more first motor points and a second sub-branch that innervates the sternothyroid muscle at one or more second motor points, and wherein implanting the signal delivery device at the target location includes implanting the signal delivery device to deliver the modulation signal to the one or more first motor points and/or the one or more second motor points.

16. The method of claim 1 wherein moving the signal delivery device in the lateral-to-medial direction includes positioning at least a portion of the signal delivery device between the sternohyoid muscle and the sternothyroid muscle.

17. The method of claim 1 wherein moving the signal delivery device in the lateral-to-medial direction includes advancing the signal delivery device along a trajectory that is anterior to a common carotid artery of the patient and an internal jugular vein of the patient.

\* \* \* \* \*